(12) United States Patent
Resnick et al.

(10) Patent No.: US 7,264,960 B2
(45) Date of Patent: Sep. 4, 2007

(54) ENZYMATIC RESOLUTION OF PROPYLENE GLYCOL ALKYL (OR ARYL) ETHERS AND ETHER ACETATES

(75) Inventors: Sol M. Resnick, Encinitas, CA (US); Felipe A. Donate, Midland, MI (US); Timothy C. Frank, Midland, MI (US); Thomas C. Thyne, Midland, MI (US); Paul Foley, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/502,692

(22) PCT Filed: Mar. 21, 2003

(86) PCT No.: PCT/US03/08941

§ 371 (c)(1),
(2), (4) Date: Jul. 27, 2004

(87) PCT Pub. No.: WO03/083126

PCT Pub. Date: Oct. 9, 2003

(65) Prior Publication Data

US 2005/0026260 A1   Feb. 3, 2005

(51) Int. Cl.
   *C12P 41/00* (2006.01)
(52) U.S. Cl. .................................... 435/280
(58) Field of Classification Search ............ None
   See application file for complete search history.

(56) References Cited

U.S. PATENT DOCUMENTS 5,541,080 A  7/1996 Sih
6,239,316 B1 5/2001 Mine et al.

OTHER PUBLICATIONS

Baumann et al., "Rapid screening of hydrolases for the enantioselective conversion of 'difficult-to-resolve' substrates", Tetrahedon: Asymmetry 11 : 4781-4790 (2000).*
Boland et al., "Esterolytic and Lipolytic Enzymes in Organic Synthesis", Synthesis 12 : 1049-1072 (1991).*
Anthonsen, H. W., et al., "A Simple Method For Calculating Enantiomer Ratio and Equilibrium Constants In Biocatalytic Resolutions", Tetrahedron: Asymmetry, 1995, vol. 6, pp. 3015-3022.
Goergens, U., et al., "A Facile Chemoenzymatic Route To Enantiomerically Pure Oxiranes: Building Blocks For Biologically Active Compounds", J. Chem. Soc., Chem. Commun., 1991, pp. 1064-1066.
Hoff, B. H., et al., "The Enantiomer Ratio Strongly Depends On The Alkyl Part Of The Acyl Donor In Transesterification With Lipase B From *Candida antarctica*", Tetrahedron: Asymmetry, 1996, vol. 7, pp. 3187-3192.
Huerta, F. F., et al., "Dynamic Kinetic Resolution Of α-Hydroxy Acid Esters", Organic Letters, 2000, vol. 2, pp. 1037-1040.
Kim, K.-W., et al., "Biocatalysis In Ionic Liquids : Markedly Enhanced Enantioselectivity Of Lipase", Organic Letters, 2001, vol. 3, pp. 1507-1509.
Kim, M.-J., et al., "Lipase/Ruthenium-Catalyzed Dynamic Kinetic Resolution Of Hydroxy Acids, Diols, And Hydroxy Aldehydes Protected With A Bulky Group", J. Org. Chem., 2001, vol. 66, pp. 4736-4738.
Larsson, A. L. E., et al., "Enzymatic Resolution Of Alcohols Coupled With Ruthenium-Catalyzed Racemization Of The Substrate Alcohol", 1997, Angew. Chem. Int Ed. Engl., vol. 36, pp. 1211-1212.
Lau, R. M., et al., "Lipase-Catalyzed Reactions In Ionic Liquids", Organic Letters, 2000, vol. 2, pp. 4189-4191.
Patkar, S. A., et al., "Purification Of Two Lipases From *Candida antarctica* And Their Inhibition By Various Inhibitors", Indian Journal of Chemistry, 1993, vol. 32B, pp. 76-80.
Persson, B. A., et al., "Dynamic Kinetic Resolution Of Secondary Diols Via Coupled Ruthenium And Enzyme Catalysis", J. Org. Chem., 1999, vol. 64, pp. 5237-5240.
Persson, B. A., et al., "Ruthenium- And Enzyme-Catalyzed Dynamic Kinetic Resolution Of Secondary Alcohols", J. Am. Chem. Soc., 1999, vol. 121, pp. 1645-1650.
Derwent Abstract Accession No. 1993-058679, WO Patent 9302034A1, Boehringer Mannheim GmbH, "New enantiomerically pure 1- (thio)alkoxy-2-hydroxyalkane derives.—prepd. by selective enzymatic esterification or hydrolysis of corresp. racemate, useful as intermediates for pharmaceuticals etc.", Feb. 4, 1993.
Derwent Abstract Accession No. 1993-171840, Japanese Patent 05103691A, Mitsubishi Kasei Corp., "Prepn. of optically active (R) -1-aryl oxy-2A-alkanol—by reacting racemic acetate ester with specified microbe or its lipase etc.", Apr. 27, 1993.
Derwent Abstract Accession No. 1993-171841, Japanese Patent 05103692A, Mitsubishi Kasei Corp., "Prepn. of an optically active ester for use in e.g. pharmaceuticals—by reacting a microbe, e.g. Hansenula, with a racemic mixt. of aryloxy-alkyl acetate to convert the R isomer to an alcohol which is then removed", Apr. 27, 1993.
Derwent Abstract Accession No. 1993-171842, Japanese Patent 05103693A, Mitsubishi Kasei Corp., "Prepn, of optically active alcohol—by reacting mixt. of R and S isomers of aryloxy-alkyl acetate with Nocardia or Rhodococcus microbe", Apr. 27, 1993.
Carrea, G. Ottolina, G., Riva, S., "Role of Solvents in the Control of Enzyme Selectivity in Organic Media", Trends in Biotechnology, vol. 13, Feb. 1955, pp. 63-70.
Kilbarov, A.M., "Improving Enzymes by Using Them in Organic Solvents", Nature vol. 409:Jan. 11, 2001, pp. 241-246.
Bovara, R., Carrea, G., Ferrara, L., Riva, S., "Resolution of (±)-trans-Sobrerol by Lipase PS-Catalyzed Transesterification and Effects of Organic solvents on Enantioselectivity", Tetrahedron Asymmetry, vol. 2, No. 9, (1991), pp. 931-938.

* cited by examiner

*Primary Examiner*—Sandra E. Saucier

(57) ABSTRACT

Glycol ether acetates, and in particular propylene glycol alkyl (or aryl) ether acetates, can be resolved enzymatically by enantioselective hydrolysis with a hydrolase at high concentrations of substrates; in some embodiments, the hydrolase is a lipase. Glycol ethers, and in particular propylene glycol alkyl (or aryl) ethers, can be resolved enzymatically by enantioselective transesterification with a hydrolase, in the presence of an acyl donor, at high concentrations of substrates; in some embodiments, the hydrolase is a lipase.

30 Claims, 8 Drawing Sheets

ENZYMATIC RESOLUTION OF PROPYLENE GLYCOL ALKYL (OR ARYL) ETHERS AND ETHER ACETATES

FIELD OF THE INVENTION

This invention is in the field of biocatalysis. The present invention relates to processes for the enzymatic resolution of glycol ethers and of glycol ether acetates, and in particular to enzymatic resolution of propylene glycol alkyl (or aryl) ethers and of propylene glycol alkyl (or aryl) ether acetates.

BACKGROUND

Enantiomers are asymmetric molecules that can exist in two different isomeric forms which have different configurations in space. Because they do not have a plane of symmetry, enantiomers are not identical with their mirror images; molecules which exist in two enantiomeric forms are chiral, which means that they can be regarded as occurring in "left" and "right" handed forms. The most common cause of chirality in organic molecules is the presence of a tetrahedral carbon bonded to four different substituents or groups. Such a carbon is referred to as a chiral center, or stereogenic center. A method for indicating the three-dimensional arrangement of atoms (or the configuration) at a stereogenic center is to refer to the arrangement of the priority of the groups when the lowest priority group is oriented away from a hypothetical observer: If the arrangement of the remaining three groups from the higher to the lower priority is clockwise, the stereogenic center has an "R" (or "D") configuration; if the arrangement is counterclockwise, the stereogenic center has an "S" (or "L") configuration.

Enantiomers have the same empirical chemical formula, and are generally chemically identical in their reactions. However, enantiomers show different chemical reactivity toward other asymmetric compounds, and respond differently toward asymmetric physical disturbances. The most common asymmetric disturbance is polarized light.

An enantiomer can rotate plane-polarized light; thus, the enantiomer is optically active. Two different enantiomers of the same compound will rotate plane-polarized light in the opposite direction; thus, the light can be rotated to the left or counterclockwise for a hypothetical observer (this is levarotatory or "l", or minus or "−") or it can be rotated to the right or clockwise (this is dextrorotatory or "d" or plus or "+"). The sign of optical rotation (+) or (−), is not related to the R,S designation) A mixture of equal amounts of two chiral enantiomers is called a racemic mixture, or racemate, and is denoted either by the symbol (+/−) or by the prefix "d,l" to indicate a mixture of dextrorotatory and levorotatory forms. Racemic mixtures show zero optical rotation because equal amounts of the (+) and (−) forms are present. But generally the presence of a single enantiomer rotates the light in only one direction; thus, a single enantiomer is referred to as optically pure.

Optically pure compounds are of interest as chiral synthons. One reason is that asymmetric molecules in living organisms are usually present in only one of their possible chiral forms. In contrast, when a chiral organic compound is synthesized in the laboratory, the synthetic reactions (in the absence of asymmetric catalysts) generally produce both chiral forms at an equal rate, leading to an equimolar, or racemic, mixture of the product isomers. The separation of a racemic mixture into its two constituent enantiomers is called resolution, but it is very difficult to separate a racemic mixture (one way is by reaction of a racemate with a standard asymmetric compound, and separating the resulting products (diastereomers) which have different physical properties, and then removing the standard asymmetric compound). However, the three-dimensional shape, or stereochemistry, of biomolecules is extremely important to their biological function. Moreover, enantiomers of the same structure may have very different biological effects. As an example, the drug thalidomide was synthesized and administered as a racemate; only one enantiomer was an effective anti-nausea drug, whereas the other enantiomer was an effective teratogen, which was tragically discovered after administration of the racemate to pregnant women.

Therefore, the synthesis of molecules for a biological function (such as a drug) preferably occurs from a single enantiomer which will result in the desired biologically active product. For example, chiral 1,2-propanediols are useful in the preparation of cardiovascular drugs, anti viral drugs, and enantiomerically pure crown ethers (Hoff et al. (1996) Tetrahedron: Asymmetry 7:3181-3186). These and related chiral compounds may also serve as synthons for chiral polymers, chromatography matrices, or as derivatization reagents for stereochemical analysis of chiral acids by LC or NMR. In addition to pharmaceutical and agricultural applications, optically active secondary alcohols, particularly those with asymmetric carbon containing fluoroalkyl groups (e.g., trifluormethyl-), are a material of interest in ferroelectric and anti-ferroelectric liquid crystals (U.S. Pat. No. 6,239,316 B1; EPO Application No. 99115154.9).

Optically pure compounds can be synthesized chemically, but asymmetric chemical synthesis often requires catalysts which are expensive and/or which may be environmentally deleterious; moreover, such syntheses are typically multistep, and often limited to substrates containing the structural requirements for a given chemistry. Mixtures of isomers or enantiomers, resulting from typical chemical syntheses, can be resolved (or separated into pure enantiomers) either chemically or enzymatically. Chemical resolution of racemates has been described above. Enzymatic resolution of racemates relies upon a preference or selectivity of an enzyme for one isomer of a racemate as a substrate; the result is the formation of a product from predominantly the preferred substrate, while leaving the non-preferred substrate predominantly as the original isomer. The preference of an enzyme toward one isomer of a racemate is known as enantioselectivity. The use of esterases, lipases, and proteases to perform kinetic resolutions of mixtures of enantiomers is well known. However, enantioselective resolution of a mixture of enantiomers is highly dependent upon not only the choice of enzyme, but also upon the chemical structure of the enzyme substrates. The optimal choice of an enzyme to resolve a given substrate or a series of related substrates is therefore not easily predicted, but requires careful screening of a variety of enzymes while varying the chemical structure of potential substrates.

Some examples of enzyme catalyzed resolution of a few propylene glycol ethers and related derivatives have been described in the scientific and patent literature. A screening for enantioselective hydrolysis of difficult-to-resolve substrates, including the acetate and butyrate esters of (±)-1-methoxy-2-propanol, has been described recently (Baumann et al. (2000) Tetrahedron: Asymmetry 11:4781-4790). The authors reported that a lipase fraction B from *Candida antarctica* (CAL-B) catalyzed enantioselective hydrolysis of (R)-1-methoxy-2-propanol acetate yielding the corresponding (S)-acetate and (R)-alcohol of greater than 99% ee and in maximum yield (50%). Preparative scale reactions were apparently conducted at 50 ml scale with 5.28% (w/v) 1-methoxy-2-propanol acetate (calculated based on 20 mmol substrate, 50 mg enzyme at 1.0 mg/ml). Enantioselective acylation of 2.7% (w/v) (±)-1-methoxy-2-propanol in hexane with vinyl acetate as acyl donor was reported to give (R)-1-methoxy-2-propanol acetate in 98% ee and 20% yield substrate conversion (Baumann et al. (2000) Tetrahedron: Asymmetry 11:4781-4790).

Another example of an optical resolution using the CAL-B lipase (Novozyme 435) is the catalysis by enantioselective transesterification of 4-isopropyloxybutan-2-ol with vinyl propionate to yield (R)-(+)-4-isopropyloxybutane-2-propionate (U.S. Pat. No. 6,239,316 B1; EPO Application No.99115154.9). Chemical hydrolysis of the ester provided the corresponding (R)-alcohol in greater than 95% ee.

Individual propylene glycol ethers (for example, propylene glycol phenyl ether or 1-phenoxy-2-propanol) and their corresponding acetates (for example, propylene glycol phenyl ether acetate or 1-phenoxy-2-propyl acetate) have been the focus of biocatalytic resolution by a number of groups. Three Japanese patents have described the manufacture of both (R)- and (S)-1-aryloxy-2-alkanols by treatment of racemic acetates with whole cells, their preparations, or lipase from them (Japanese Patent Application Nos. JP 1991-262377, JP 1991-262378, and JP 1991-262379); much of the work described in the patents was later published (Yanase et al. (1993) Biosci. Biotech. Biochem. 57:1334-1337). In addition, hydrolytic resolution of the butanoic ester of 1-phenoxy-2-propanol has been studied with CAL-B and other lipases (Hoff et al. (1996) Tetrahedron: Asymmetry 7:3181-3186). Transesterification of 1-phenoxy-2-propanol with 2-chloroethylbutanoate and other acyl donors has been used in the development of a computer program for calculating enantiomer ratio and equilibrium constants in biocatalytic resolutions (Anthonsen et al. (1995) Tetrahedron: Asymmetry 6:3015-3022; Hoff et al. (1996) Tetrahedron: Asymmetry 7:3187-3192). The transesterification of 1-phenoxy-2-propanol (approx 3% w/v) has also been demonstrated with polymer activated forms of pig liver esterase (PLE) using vinyl propionate as acyl donor (Gais et al. (2001) J. Org. Chem. 66:3384-3396).

However, enantioselective resolution via enzymatic hydrolysis or acylation has not been reported for racemates of related propylene glycol alkyl (or aryl) ethers and their corresponding acetates; exemplary members of these related glycol ethers include but are not limited to propylene glycol ethyl ether, propylene glycol n-propyl ether, propylene glycol isopropyl ether, propylene glycol n-butyl ether, propylene glycol t-butyl ether, and their corresponding acetates. Nor have reaction conditions been described for either hydrolysis or acylation of propylene glycol methyl ether or propylene glycol phenyl ether or their corresponding acetates at high substrate concentrations which result in the formation of products in high enantiopurity and in high yields.

Glycol ethers and their corresponding acetates, and in particular, propylene glycol alkyl (or aryl) ethers and their corresponding acetates, have been particularly difficult to resolve in a commercially feasible manner. Therefore, it would be useful to develop processes for resolving racemic mixtures of propylene glycol alkyl (or aryl) ethers and their corresponding acetates, where the processes are enzymatic, result in a high degree of separation at a high yield, and are fast and economical.

Definitions and Abbreviations

To facilitate an understanding of the present invention, a number of abbreviations, terms and phrases as used herein are defined below.

"*Candida antarctica* lipase fraction B" is abbreviated as CALB or CAL-B.

"Enzyme activity units" are abbreviated as U.

"Enantiomeric excess" is abbreviated as ee.

"Enantioselectivity" is abbreviated as E.

"Propylene glycol methyl ether" (also 1-methoxy-2-propanol) is abbreviated as PM.

"Propylene glycol methyl ether acetate" (also 1-methoxy-2-propanol acetate) is abbreviated as PMA.

"Propylene glycol ethyl ether" (1-ethoxy-2-propanol) is abbreviated as PE.

"Propylene glycol ethyl ether acetate" (1-ethoxy-2-propanol acetate) is abbreviated as PEA.

"Propylene glycol n-propyl ether" (1-n-propyloxy-2-propanol) is abbreviated as PnP.

"Propylene glycol n-propyl ether acetate" (1-n-propyloxy-2-propanol acetate) is abbreviated as PnPA.

"Propylene glycol isopropyl ether" (1-isopropyloxy-2-propanol) is abbreviated as PiP.

"Propylene glycol isopropyl ether acetate" (1-isopropyloxy-2-propanol acetate) is abbreviated as PiPA.

"Propylene glycol n-butyl ether" (1-n-butyloxy-2-propanol) is abbreviated as PnB.

"Propylene glycol n-butyl ether acetate" (1-n-butyloxy-2-propanol acetate) is abbreviated as PnBA.

"Propylene glycol tert-butyl ether" (1-tert-butyloxy-2-propanol) is abbreviated as PtB.

"Propylene glycol tert-butyl ether acetate" (1-tert-butyloxy-2-propanol acetate) is abbreviated as PtBA.

"Propylene glycol phenyl ether" (1-phenoxy-2-propanol) is abbreviated as PPh.

"Propylene glycol phenyl ether acetate" (1-phenoxy-2-propanol acetate) is abbreviated as PPhA.

"Propylene series glycol ethers" or "P-series glycol ethers" or "P-series substrates" refers to propylene glycol alkyl (or aryl) ether, and includes but is not limited to the compounds listed above, PM, PE, PnP, PiP, PnB, PtB, and PPh. This class of compounds includes generally any glycol ether prepared by reacting propylene oxide under basic conditions with a compound containing an alcohol functionality.

"Propylene series glycol ether acetates" or "P-series glycol ether acetates" or "P-series acetate substrates" refers to propylene glycol alkyl (or aryl) ether acetates, and includes but is not limited to the compounds listed above, PMA, PEA, PnPA, PiPA, PnBA, PtBA, and PPhA. This class of compounds includes generally acetate derivatives mainly at the C-2 hydroxyl position of "1-substituted ethers of 2-propanol" compounds defined above.

"Propylene glycol alkyl (or aryl) ether" is abbreviated PGAE.

"Propylene glycol alkyl (or aryl) ether acetate" is abbreviated PGAEA.

An "acylated propylene glycol alkyl (or aryl) ether" is abbreviated acyl-PGAE, and it includes PGAEA.

"Butyl acetate" is abbreviated BA.

"4-Ethylphenyl acetate" is abbreviated EPA.

"Ethyl acetate" is abbreviated EtA.

"Ethyl trichloroacetate" is abbreviated EtCA.

"Ethyl trifluoroacetate" is abbreviated EtFA.

"Isopropenyl acetate" is abbreviated IPA.

"Vinyl acetate" is abbreviated VA.

"Ethyl methoxyacetate" is abbreviated EMA.

"2,2,2-trifluoroethyl butyrate" is abbreviated TfEB.

"Diketene" is abbreviated DK.

"Vinyl propionate" is abbreviated VP.

"Lactide" is 3,6-Dimethyl-1,4-dioxane-2.5-dione

Ratio "v/v" refers to volume/volume.

The term "isomer" refers to compounds having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane-polarized light in different directions). Enantiomers generally have identical physical properties, such as melting points and boiling points, and also have identical spectroscopic properties. Enantiomers can differ from each other with respect to their interaction with plane-polarized light and with respect to biological activity.

The designations "R and S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses.

The designations or prefixes "(+) and (−)" are employed to designate the sign of rotation of plane-polarized light by the compound, with (−) meaning that the compound is levorotatory (rotates to the left). A compound prefixed with (+) is dextrorotatory (rotates to the right).

The term "racemic mixture," "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction $F_{(+)}$ and $F_{(-)}$ (where the sum of $F_{(+)}$ and $F_{(-)}=1$). The enantiomeric excess is defined as $*F_{(+)}-F_{(-)}*$ and the percent enantiomeric excess by $100\times*F_{(+)}-F_{(-)}*$. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer," "substantially resolved enantiomer" "substantially purified enantiomer preparation" are meant to indicate a preparation (e.g. derived from non optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer," "resolved enantiomer" and "purified enantiomer preparation" are meant to indicate a preparation (e.g. derived from non optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereopreferred procedure, followed by separation steps, or a purified enantiomer may be derived from a racemic mixture.

The term "enantioselectivity," also called the enantiomeric ratio indicated by the symbol "E," refers to the selective capacity of an enzyme to generate from a racemic substrate one enantiomer relative to the other in a product racemic mixture; in other words, it is a measure of the ability of the enzyme to distinguish between enantiomers. A non-selective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

The calculation of E is based upon the measurement of two of three variables: enantiometric purity of the starting material ($ee_s$), enantiometric purity of the product ($ee_p$), and extent of conversion (c), then one of the following three equations can be used (from Hydrolases in Organic Synthesis, Bornscheuer, U T and Kazlauskas, R J (1999) Wiley-VCH, New York), section 3.1.1; and Chen et al., J. Am. Chem. Soc. 104:7294-7299 (1982):

$$E = \ln[1-c(1+ee_p)]/\ln[1-c(1-ee_p)]$$

$$E = \ln[(1-c)(1-ee_s)]/\ln[(1-c)(1+ee_s)]$$

$$E = \ln\{(1-ee_s)/[1+(ee_s/ee_p)]\}/\ln\{(1+ee_s)/[1+(ee_s/ee_p)]\}$$

The term "acyl donor" refers to a suitably reacting compound leading to the formation of an ester in the presence of an enzymatic catalyst and a substrate. In the present invention, the substrate is a glycol ether, and in particular a propylene glycol alkyl (or aryl) ether, and the enzymatic catalyst is a hydrolase, and preferably a lipase, and even more preferably CAL-B. Acyl donors include non-activated or activated acyl donors. Non-limiting examples of non-activated acyl donors include propylene glycol methyl ether acetate (PMA), propylene glycol ethyl ether acetate (PEA), propylene glycol n-propyl ether acetate (PnPA), ethyl acetate (EA), butyl acetate (BA) and ethyl phenyl acetate (EPA). Non-limiting examples of activated acyl donor are activated esters (including but not limited to trifluoroethyl butyrate, S-ethyl thio-octanoate, and biacetyl mono-oxine acetate,) enol esters (but not limited to vinyl acetate, isopropenyl acetate, and 1-ethoxyvinyl acetates, and diketene), and anhydrides (acetic acid anhydride, lactide, and succinic acid anhydride). Non-limting examples of acyl donors include butyl acetate (BA), ethyl phenyl acetate (EPA), ethyl acetate (EtA), ethyl trichloroacetate (EtCA), ethyl trifluoroacetate (EtFA), isopropenyl acetate (IPA), vinyl acetate (VA), ethyl methoxy acetate (EMA), 2,2,2-trifluoroethyl butyrate (TfEB), diketene (DK), vinyl propionate (VP), PMA and PnPA.

The term "yield" when used to describe the production of a product in an enzyme catalyzed reaction refers to the amount of substrate converted to product in the reaction. Yield is based upon the amount of substrate originally present in a reaction mixture, and the percent (%) of substrate converted to product. The term "yield" is also used to describe the amount of remaining unconverted substrate in an enzyme catalyzed reaction.

The term "conversion" when used to describe the production of a product in an enzyme catalyzed reaction refers to the proportion or percent of substrate converted to product in the reaction.

The term "reaction mixture" refers to a combination of enzyme catalyst and substrate in which the enzyme catalyzes a reaction converting the substrate to a product; more than one substrate (such as a PGAE and an acyl donor) or more than one product (such as a PGAEA and PGAE) may be present. Additional components may also be present in a reaction mixture.

The term "reaction matrix" refers to a reaction mixture without the presence of an enzyme catalyst; thus, the matrix can be a reaction mixture from which the enzyme catalyst has been removed, or it can be a combination of the reaction mixture components except for an enzyme catalyst.

The term "reaction medium" refers to a solution in which an enzyme catalyst and at least one substrate are combined (such as dissolving or suspending or mixing). The medium may be aqueous, which is preferably buffered, or it may contain solvents in addition to or essentially instead of water. The solvents may be soluble or insoluble in water. The solvent may be a single compound or a combination of several compounds. The amount of solvent in the reaction medium may be from none to about 100% of the medium.

The term "biphasic reaction medium" refers to a reaction medium comprising an aqueous phase and a solvent which is immiscible in the aqueous phase and which is present in addition to the substrates (which are themselves solvents); thus, a biphasic reaction medium comprises two immiscible solvents, which separate into two phases. Typically, such a reaction medium comprises an aqueous phase (generally buffered) and an organic solvent which is of limited solubility in the aqueous phase. The aqueous phase can be very small (may comprise only slightly more than about 3% of the total reaction mixture volume).

The terms "aprotic" or "non-aqueous" when used in reference to a reaction medium refer to a reaction mixture which has substantially no aqueous phase (such that the aqueous phase is about equal to or less than about 3% of the total reaction mixture volume), and which comprises at least one solvent which is preferably non-polar; preferably such solvents are organic.

The term "co-solvent" when used in reference to a reaction medium refers to non substrate and non-product solvents, where the substrate and products are themselves solvents.

The term "enzyme catalyst" refers to an enzyme capable of converting a substrate to a product. Preferably, the substrate is enantioselectively converted to a product The term "effective amount" when used in reference to an enzyme refers to an amount of enzyme present in a reaction mixture which catalyzes a reaction such that the substrate is converted to the product at a reasonable level within a reasonable time period. A reasonable level of enantioselective substrate conversion to product for a racemic mixture will depend upon both the desired yield and the desired purity of either the product or the remaining product; typically, the yield is in the range of about 30% to 50% of desired product (even when reaction conversions approach 80% of substrate), with purity in the range of about 75% ee to greater than 99% ee. A reasonable time is commercially determined; for an enantioselective substrate conversion to product for a racemic mixture, the time is typically from about an hour to about 80 hours, the time being either batch reaction time for a batch process, or liquid residence time given by liquid-filled reactor volume divided by volumetric liquid flow rate, for a continuous process.

The term "recycling" when used in reference to an enzyme catalyst means the recovery and reuse of the enzyme catalyst in more than one batch of reaction mixture or to increase the volumetric productivity through reuse in a continuous reaction process. The term "high productivity" when used in reference to an enzyme catalyst means that the catalyst can be used to process a large amount of liquid feed per unit weight of catalyst with little loss of activity, in batch or continuous modes of operation.

SUMMARY OF THE INVENTION

The present invention provides a process comprising contacting in a reaction mixture a propylene glycol ether acetate racemate of formula I

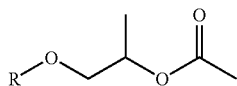

(I)

where R is selected from an alkyl or aryl group, with an effective amount of an enzyme catalyst hydrolase whereby an -enantiomer (R or S) of the racemate is enantioselectively hydrolyzed to a corresponding propylene glycol ether. Non-limiting example of R in formula I above are $CH_3$, $CH_3CH_2$, $CH_3(CH_2)_2$, $CH_3(CH_2)_3$, $CH(CH_3)_2$, $C(CH_3)_3$ and $C_6H_5$. A suitable hydrolase for use in the present invention is selected from the group consisting of a lipase, an esterase, an acylase and a protease. Preferred hydrolases are a lipase and an esterase. Most preferred hydrolase is a lipase; and in particularly preferred lipase is selected from the group consisting of a *Candida antarctica* lipase fraction B, a lipase LP 'S', a *Pseudomonas* sp. lipoprotein lipase, a *Pseudomonas* sp. lipase, and a *Pseudomonas cepacia* lipase. The most preferred lipase is a *Candida antarctica* lipase fraction B. Preferred esterases include E001, E002 and E003 (sold by Thermogen Inc.) and pig liver esterase (PLE). The concentration of the racemate in the reaction mixture is greater than about 10% v/v, preferably greater than about 20% v/v. In some embodiments hydrolysis occurs in an aqueous reaction medium; in alternative embodiments, hydrolysis occurs in a biphasic reaction medium. In further embodiments, about 30% to about 50% of the racemate is hydrolyzed. In yet further embodiments, enantiomer purity of the hydrolyzed racemate is at least about 70% ee. In other embodiments, the process of the present invention further comprises recovering the R-propylene glycol ether from the reaction mixture. In yet other embodiments, the process of the present invention further comprises recovering unreacted S-enantiomeric substrate from the reaction mixture, and converting the S-enantiomeric substrate to obtain a corresponding S-propylene glycol ether by methods such as chemical hydrolysis or transesterification. In yet other embodiments, the process of the present invention further comprises recycling the enzyme catalyst.

In another aspects, the present invention provides a process comprising contacting in a reaction mixture a propylene glycol ether racemate of formula II

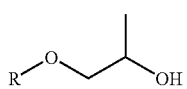

(II)

where R is selected from an alkyl or aryl group, and where the racemate is at a concentration of at least about 5% v/v, where the reaction mixture further comprises an acyl donor, with an effective amount of an enzyme catalyst hydrolase whereby an R-enantiomer of the racemate is enantioselectively transesterified to a corresponding R-acylated propylene glycol ether. Non-limiting examples of R in formula II above are $CH_3$, $CH_3CH_2$, $CH_3(CH_2)_2$, $CH_3(CH_2)_3$, $CH(CH_3)_2$, $C(CH_3)_3$ and $C_6H_5$. The acyl donor can be either a non-activated or an activated acyl donor. The activated acyl donor is selected from an activated ester, an enol ester, and an anhydride. Non-limiting examples of suitable activated acyl donors are vinyl acetate, vinyl propionate, 2,2,2-trichloroethyl acetate, 2,2,2-trifluoroethyl acetate, butyl acetate, ethylphenyl acetate, isopropenyl acetate, ethyl methoxyacetate, 1-ethoxyvinyl acetate, diketene, trifluoroethyl butyrate, acetic acid anhydride, lactide, and succinic acid anhydride. Preferred activated acyl donors are vinyl acetate and isopropenyl acetate. Non-limiting examples of suitable non-activated acyl donors are ethyl acetate and a chiral acyl donor compound such as, for example, racemic 1-methoxy-2-propanol acetate (PMA), propylene glycol ethyl ether acetate (PEA), propylene glycol n-propyl ether acetate (PnPA), ethyl acetate(EA), butyl acetate (BA) and ethyl phenyl acetate (EPA). A suitable hydrolase for use in the present invention is selected from the group consisting of a lipase, an esterase, an acylase and a protease. Preferred hydrolases are a lipase and an esterase. Most preferred hydrolase is a lipase; and in particularly preferred lipase is selected from the group consisting of a *Candida antarctica* lipase fraction B, a lipase LP 'S', a *Pseudomonas* sp. lipoprotein lipase, a *Pseudomonas* sp. lipase, and a *Pseudomonas cepacia* lipase. The most preferred lipase is a *Candida antarctica* lipase fraction B. Preferred esterase is polymer activated-pig liver esterase (PLE). The racemate and the acyl donor can comprise about 100% v/v of the reaction mixture. In some embodiments, the racemate and the acyl donor are present in a ratio which results in about 50% conversion of the racemate to acylated propylene glycol ether. In some embodiments, about 30% to about 50% of the racemate is transesterified and enantiomer purity of the acylated propylene glycol ether is at least about 70% ee. In other embodiments, the process of the present invention furter comprises recovering the R-acylated propylene glycol alkyl ether from the reaction mixture, and converting the R-acylated propylene glycol alkyl ether to obtain a corresponding R-propylene glycol alkyl ether. In yet other embodiments, the process of the present invention further comprises recovering unreacted S-enantiomeric substrate from the reaction mixture. In yet other embodiments, the process of the present invention further comprises recycling the enzyme catalyst.

In another aspect, the present invention provides a method for controlling the extent of substrate conversion in a process for resolving a racemic mixture of propylene glycol ethers by transesterification, where a first substrate, a propylene glycol ether, is transesterified by a second substrate, an acyl donor, where the method comprises (a) determining desired enantiometric yield of converted substrate (typically, from about 30% to about 50%) and desired purities of converted and/or unconverted substrate (typically, conversion of about 30 to about 70%, and purity >90% ee); (b) calculating molar ratios of the first substrate and the second substrate to achieve the desired yield and purities; (c) calculating amounts of the first substrate and the second substrate to theoretically achieve the desired yields and purities based upon the molar ratios; and (d) combining in a reaction mixture a first calculated amount of the first substrate comprising a racemic mixture of a propylene glycol ether of formula II

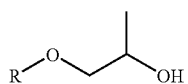

(II)

where R is selected from an alkyl, aryl, aryl-substituted alkyl, allylic or acetal group, and a second calculated amount of the second substrate comprising an-acyl donor selected from the group consisting of an activated ester, a non-activated ester, an enol ester and an anhydride, with an effective amount of an enzyme catalyst hydrolase whereby a first enantiomer of the racemate is enantioselectively transesterified to a corresponding first enantiomeric acylated propylene glycol ether. In some embodiments, the first calculated amount of the first substrate is a first volume and the calculated amount of the second substrate is a second volume. In some embodiments, the first calculated amount of the first substrate and the second calculated amount of the second substrate comprise about 100% of a reaction matrix of the reaction mixture. Suitable acyl donors can be either non-activated or activated acyl donors. Activated acyl donors are selected from the group consisting of an activated ester, an enol ester, and an anhydride. Non-limiting examples of the preferred activated acyl donors are vinyl acetate, vinyl propionate, 2,2,2-trichloroethyl acetate, 2,2,2-trifluoroethyl acetate, butyl acetate, ethylphenyl acetate, isopropenyl acetate, ethyl methoxyacetate, 1-ethoxyvinyl acetate, diketene, trifluoroethyl butyrate, acetic acid anhydride, lactide, and succinic acid anhydride. Preferred activated acyl donors are vinyl acetate and isopropenyl acetate. Non-limiting examples of suitable non-activated acyl donors are ethyl acetate and a chiral acyl donor compound such as, for example, racemic 1-methoxy-2-propanol acetate (PMA), butyl acetate (BA), ethyl phenyl acetate (EPA), ethyl acetate (EtA), and PnPA. Non-limiting examples of R in formula II above are $CH_3$, $CH_3CH_2$, $CH_3(CH_2)_2$, $CH_3(CH_2)_3$, $CH(CH_3)_2$, $C(CH_3)_3$, $C_6H_5$, $C(CH_3)_3$, $C(CH_3)_2C_6H_5$, $C(CH_3)(C_6H_5)_2$, $C(C_6H_5)_3$, $C(CH_3)_2CH_2CH_3$, $CH_2C_6H_5$, $CH_2CH=CH_2$, $CH_2C\equiv CH$, $CH_2OCH_2CH_2OCH_3$, and $CH_2OCH_3$. A suitable hydrolase for use in the present invention is selected from the group consisting of a lipase, an esterase, an acylase and a protease. Preferred hydrolases are a lipase and an esterase. Most preferred hydrolase is a lipase; and in particularly preferred lipase is selected from the group consisting of a *Candida antarctica* lipase fraction B, a lipase LP 'S', a *Pseudomonas* sp. lipoprotein lipase, a *Pseudomonas* sp. lipase, and a *Pseudomonas cepacia* lipase. The most preferred lipase is a *Candida antarctica* lipase fraction B. Preferred esterase is polymer activated pig liver esterase (PLE). In some embodiments, an (R)-enantiomer of the racemate is enantioselectively transesterified to a corresponding (R)-enantiomeric acylated propylene glycol ether. In other embodiments, the method of the present invention further comprises recovering the first enantiomeric acylated propylene glycol alkyl ether product from the reaction mixture, and converting the product to obtain a corresponding first enantiomeric propylene glycol alkyl ether by a suitable method such as hydrolysis or transesterification. In yet other embodiments, the method of the present invention further comprises recovering unreacted second enantiomeric propylene glycol alkyl ether from the reaction mixture. In still other embodiments, the method of the present invention further comprises recycling the enzyme catalyst. In other embodiments, the method of the present invention further comprises monitoring yield of acylated propylene glycol ethers and enantiomer purity of either acylated or non-acylated propylene glycol ethers, and adjusting the ratio of the first substrate to the second substrate to achieve desired yield and purities. In other embodiments, the method of the present invention involving the use of racemic glycol ether acetates as acyl donors further comprises removal of byproduct alcohol from the reaction mixture to increase conversion of the reagent and the generation of up to four chiral compounds in the same reaction.

In another aspects, the present invention provides a process for the preparation of the chiral compound of formula III

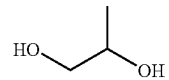

(III)

in the R or S configuration, said process comprising the steps of:

(a) contacting, at the temperature of from about 4° C. to about 80° C., in a reaction mixture a propylene glycol ether racemate of formula II

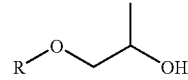

(II)

where R is an alkyl, aryl-substituted alkyl, allylic or acetal group, and where the reaction mixture further comprises an acyl donor selected from the group consisting of an activated ester, a non-activated ester, an enol ester and an anhydride, with an effective amount of an enzyme catalyst hydrolase selected from the group consisting of a lipase, an esterase, an acylase and a protease whereby (S)-1-alkoxy-2-propanol and (R)-1-alkoxy-2-propanol acylate are obtained;

(b) separating (S)-1-alkoxy-2-propanol from (R)-1-alkoxy-2-propanol acylate formed in step (a) using a suitable separation method such as, for example, distillation or extraction;

(c) dealkoxylating (S)-1-alkoxy-2-propanol separated in step b) under mild reaction conditions in the presence of an acid catalyst such as, for example, p-toluene sulfonic acid or a sulfonated ion exchange resin, in an amount from about 5-15, preferably 5-10, wt %, to obtain (S)-1,2-propanediol; and (d) isolating (S)-1,2-propanediol obtained in step (c) by a suitable separation method(s) such as, for example extraction and/or distillation; and, optionally, (e) dealkoxylating (R)-1-alkoxy-2-propanol acylate, separated in step (b), under mild reaction conditions in the presence of an acid catalyst catalyst such as, for example, p-toluene sulfonic acid or a sulfonated ion exchange resin, in an amount from about 5-15, preferably 5-10, wt %, to obtain (R)-1,2-propanediol; and (f) isolating (R)-1,2-propanediol obtained in step (e) by a suitable separation method(s) such as, for example extraction and/or distillation.

Non-limiting examples of R in formula II above are $C(CH_3)_3$, $C(CH_3)_2C_6H_5$, $C(CH_3)(C_6H_5)_2$, $C(C_6H_5)_3$, $C(CH_3)_2CH_2CH_3$, $CH_2C_6H_5$, $CH_2CH=CH_2$, $CH_2C\equiv CH$, $CH_2OCH_2CH_2OCH_3$, and $CH_2OCH_3$. The acyl donor can be either a non-activated or an activated acyl donor. The activated acyl donor is selected from an activated ester, an enol ester, and an anhydride. Non-limiting examples of suitable activated acyl donors are vinyl acetate, vinyl propionate, 2,2,2-trichloroethyl acetate, 2,2,2-trifluoroethyl acetate, butyl acetate, ethyl phenyl acetate, isopropenyl acetate, ethyl methoxyacetate, 1-ethoxyvinyl acetate, diketene, trifluoroethyl butyrate, acetic acid anhydride, lactide, and succinic acid anhydride. Preferred activated acyl donors are vinyl acetate and isopropenyl acetate. Non-limiting examples of suitable non-activated acyl donors are ethyl acetate and a chiral acyl donor compound such as, for example, racemic 1-methoxy-2-propanol acetate (PMA), propylene glycol ethyl ether acetate (PEA), propylene glycol n-propyl ether acetate (PnPA), ethyl acetate (EA), butyl acetate (BA) and ethyl phenyl acetate (EPA). A suitable hydrolase for use in the present invention is selected from the group consisting of a lipase, an esterase, an acylase and a protease. Preferred hydrolases are a lipase and an esterase. Most preferred hydrolase is a lipase; and particularly preferred lipase is selected from the group consisting of a *Candida antarctica* lipase fraction B, a lipase LP 'S', a *Pseudomonas* sp. lipoprotein lipase, a *Pseudomonas* sp. lipase, and a *Pseudomonas cepacia* lipase. The most preferred lipase is a *Candida antarctica* lipase fraction B. Non-limiting examples of suitable dealkoxylation catalysts are p-toluene sulfonic acid (p-TSA), DOWEX DR-2030 ion exchange resin, DOWEX MSC-1H+ ion exchange resin, acid clays, Nafion H+ catalysts, and mineral acids such as, for example sulfuric acid. DOWEX is a trademark of the Dow Chemical Company. Nafion is a trademark of DuPont. The dealkoxylation step is conveniently conducted at the temperature of from about 40° C. to about 130° C., preferably from about 80° C. to about 100° C.

Conventional kinetic resolutions of racemic mixtures as described above have the disadvantage that the theoretical maximum yield of either enantiomeric product is 50%. Complete transformation of a single enantiomer present in the racemic substrate can be achieved through a dynamic kinetic resolution. This strategy combines lipase catalyzed acylation with the ruthenium-catalyzed racemization of the substrate to allow formation of products in high yield and high optical purity. In dynamic kinetic resolution, the unreactive enantiomer of the substrate (that which does not react or reacts only slowly with the lipase) is continuously racemized and the product can be theoretically obtained in optically pure form in 100% yield. Examples of this approach have been demonstrated for secondary alcohols (Larsson, A. L. E. et al. 1997. Angew. Chem., Int Ed. Engl. 36:1211-1212; Kim, M.-J. et al. 2001. J. Org. Chem. 66:4736-4738), diols (Pearson, B. A. et al. 1999. J. Org. Chem. 64:5237-5249), and alpha-hydroxy acid esters (Huerta, F. F et al. 2000. Org. Lett. 2:1037-1040). In fact, the rutheniun- and enzyme-catalysed dynamic kinetic resolution of about 6% (w/v) 1-phenoxy-2-propanol has been demonstrated by CAL-B with 4-chlorophenyl acetate as acyl donor (Persson et al. 1999. J. Am. Chem. Soc. 121:1645-1650.); R-1-phenoxy-2-propanol was reported as the product in a yield of 88% and % ee of >99%—Applying this approach to transesterication based resolution of propylene glycol alkyl (or aryl) ethers could increase yields of desired acylated chiral products or materials derived from them.

DESCRIPTION OF THE INVENTION

The present invention relates to processes for the enzymatic resolution of glycol ethers and of glycol ether acetates, and in particular to enzymatic resolution of propylene glycol alkyl (or aryl) ethers and of propylene glycol alkyl (or aryl) ether acetates.

The present invention provides processes for the enzymatic resolution of glycol ethers and glycol ether acetates, and in particular of propylene glycol alkyl (or aryl) ethers and of propylene glycol alkyl (or aryl) ether acetates.

Exemplary glycol ether acetates have the following chemical structure:

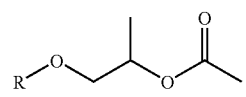

Formula I where R is selected from an alkyl or aryl group. Non-limiting examples of alkyl and aryl groups contemplated by R in formula II above are $CH_3$, $CH_3CH_2$, $CH_3(CH_2)_2$, $CH_3(CH_2)_3$, $CH(CH_3)_2$, $C(CH_3)_3$ and $C_6H_5$.

Exemplary glycol ethers have the following chemical structure:

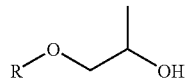

Formula II where R is selected from an alkyl or aryl group. Non limiting examples of alkyl and aryl groups contemplated by R in Formula II above are $CH_3$, $CH_3CH_2$, $CH_3(CH_2)_2$, $CH_3(CH_2)_3$, $CH(CH_3)_2$, $C(CH_3)_3$ and $C_6H_5$.

Figure 1:
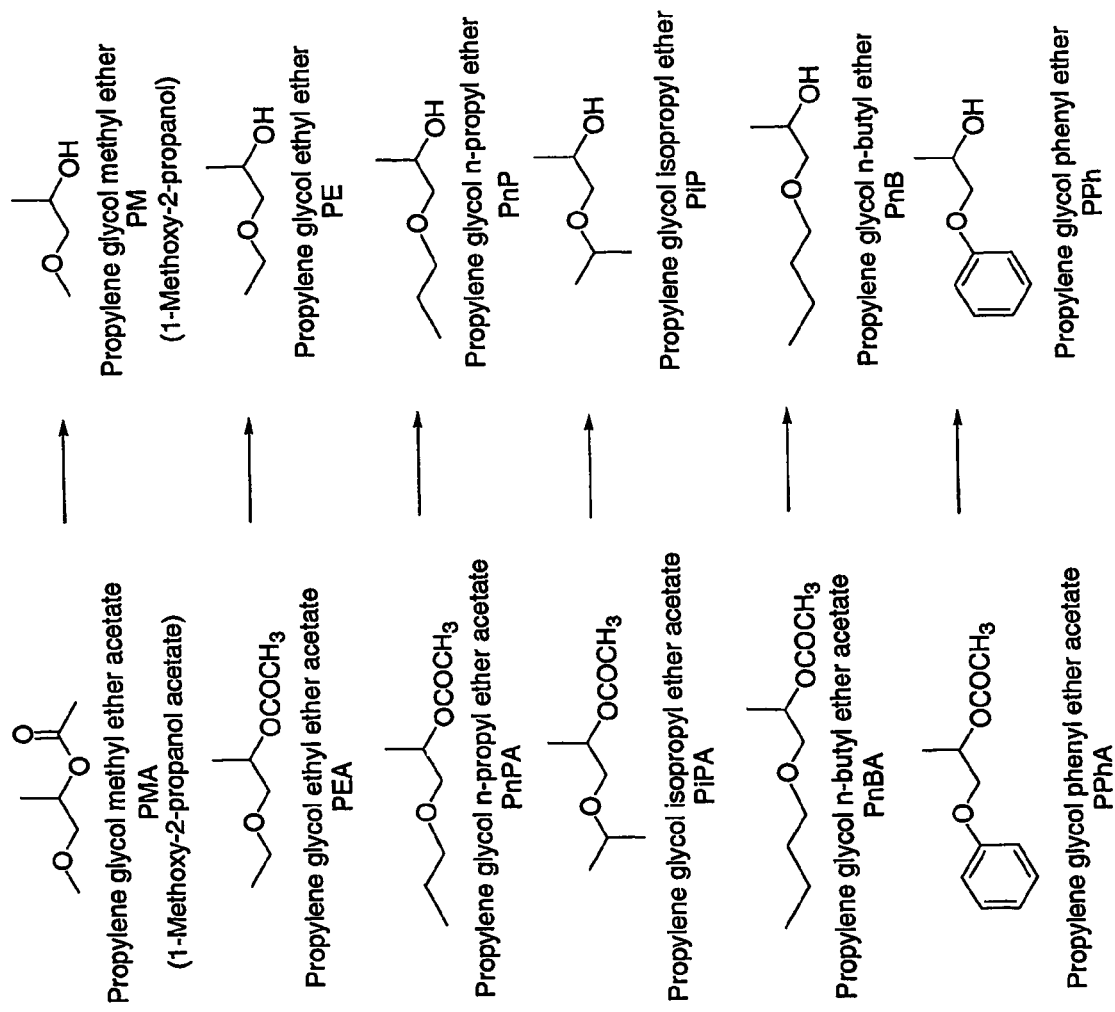
FIG. 1 shows a set of propylene glycol alkyl (or aryl) ethers and their corresponding acetates.

Non-limiting examples of propylene glycol alkyl (or aryl) ether acetates contemplated by Formula I above and propylene glycol alkyl (or aryl) ethers contemplated by Formula II above are illustrated in FIG. 1.

Enzyme catalysts for the enzymatic resolution of racemic propylene glycol alkyl (or aryl) ether acetates are those which hydrolyze the acetate of only one of the two enantiomers present in the racemic mixture with a high degree of enantioselectivity (for example, in some embodiments greater than about 90%, and in other embodiments greater than about 95%, enantiomeric excess (ee) of remaining substrate) at high proportions of conversion of a racemic mixture, (for example, in some embodiments about 40%, and in other embodiments about 50% conversion), such that the remaining propylene glycol alkyl (or aryl) ether acetate mixture is highly resolved (for example, in some embodiments, the mixture comprises greater than about 97.5% of the S-isomer and less than about 2.5% of the R-isomer, in other embodiments, the mixture comprises greater than about 97.5% of the R-isomer and less than about 2.5% of the S-isomer). An advantage of enantioselective hydrolysis of the R-isomer, resulting in resolved (S)-propylene glycol alkyl (or aryl) acetate, is that the (S)-glycol ether acetate is relatively easily chemically converted to the corresponding (S)-glycol ether.

The calculations of ee and enantioselectivity (E) relative to conversion in enzymatic resolutions of racemic mixtures of chiral compounds have been described (U.S. Pat. No. 5,541,080)

During the development of the present invention, more than 110 commercial hydrolases (lipases, esterases, acylases, and proteases) were initially screened for their ability to catalyze enantioselective hydrolysis of a racemic mixture of a test glycol alkyl ether acetate, (±)-PMA [(±)-1-methoxy-2-propanol acetate]. Enzyme screening was conducted under aqueous reaction conditions with 0.5% (v/v) PMA. Chiral capillary gas chromatography with a β-DEX 325 column was used to monitor the enantiomeric composition of the acetate substrate and the formation of the alcohol product, 1-methoxy-2-propanol (PM). One enzyme exhibiting high enantioselectivity during the initial screening was selected for subsequent examination of its performance at different parameters (i.e., high substrate concentrations, biphasic conditions, temperature, etc.) to facilitate the development of an enzymatic bioprocess. The same enzyme was also capable of catalyzing enantioselective hydrolysis of additional related propylene glycol alkyl or aryl ether acetates (see Example 5).

Results based on a screen of over 110 commercial hydrolases indicated that Candida antarctica lipase type B (CAL-B) catalyzed the enantioselective hydrolysis of the (R)-enantiomer of PMA [(±)-1-methoxy-2-propanol acetate] resulting in the resolution of the (S)-enantiomer (greater than 99% ee) of this glycol ether alkyl acetate (see Example 3). The same enzyme, CAL-B, was also shown to catalyze enantioselective acylation (transesterification) of a racemic mixture of PM under aprotic solvent or non-aqueous conditions with an acyl donor to yield enantiomerically enriched (R)-PMA and unreacted (S)-PM (See Example 6). General conditions were then determined for the use of CAL-B or similar lipases to effect resolutions of either optically active PMA or PM in high yields in biocatalytic processes. Both of the resolved optically active species (glycol ether acetate and glycol ether) can be recovered and isolated from the reaction mixture by a number of techniques, which include but are not limited to liquid-liquid extraction, thermally-activated separation, distillation, solid-phase extraction methods, liquid-solid adsorption, or a combination thereof; in preferred embodiments, the resolved optically active species are distilled. Methods such as chemical hydrolysis or transesterification of the recovered optically active glycol ether acetate easily afford the corresponding chiral glycol ether in pure form.

A panel of more than 110 commercial hydrolases was also screened for enantioselective hydrolysis of additional related glycol ether acetates. Exemplary substrates include: (±)-1-ethoxy-2-propanol acetate (PEA), (±)-1-n-propyloxy-2-propanol acetate (PnPA), (±)-1-isopropyloxy-2-propanol acetate (PiPA), (±)-1-n-butyloxy-2-propanol acetate (PnBA), and (±)-1-phenoxy-2-propanol acetate (PPhA) (along with PMA, these substrates are collectively referred to as P-series substrates). For the P-series substrates screened, Candida antarctica lipase B (CAL-B) was the most enantioselective enzyme (examples are shown in Tables 1-5). Other hydrolases, including Pseudomonas sp. lipase (PSL), Candida antarctica lipase A (CAL-A) and Candida rugosa lipase (CRL), also catalyzed enantioselective hydrolysis of some of the substrates.

Moreover, the lipase CAL-B was also used for transesterification-based resolution of PE, PnP, PiP, PnB, PtB and PPh in organic solvent with a variety of acyl donors (for example, including but not limited to ethyl acetate and vinyl acetate). Depending upon the extent of substrate conversion, (R)-enantiomers of the corresponding glycol ether acetates were formed as products in high optical purity; this would also result in the presence of the remaining unconverted (S)-enantiomer at high optical purity.

Thus, the present invention provides processes for the enzymatic resolution of two different types of substrates, propylene glycol alkyl (or aryl) ethers and propylene glycol alkyl (or aryl) ether acetates. The enzymatic catalyst is a hydrolase, and catalyzes, preferably reversibly, hydrolysis of esters. Thus, the enzymatic catalyst hydrolase also catalyzes a transesterification. In different embodiments of the invention, the enzyme catalyzes one of two different reactions, depending upon which racemate is the substrate, and upon the appropriate reaction conditions.

In some embodiments, the reaction catalyzed is hydrolysis, in which a propylene glycol alkyl (or aryl) ether acetate is hydrolyzed to propylene glycol alkyl (or aryl) ethers, liberating the acetate group as acetic acid. In the hydrolysis reaction, the enzyme enantioselectively hydrolyzes one isomer; this results in the enrichment of the hydrolyzed product of this isomer, and in the enrichment of the substrate in the other isomer, which is not as rapidly converted to the product Thus, in particular embodiments, when the enzyme is CAL-B and the substrate a racemate of a propylene glycol alkyl (or aryl) ether acetate, the process of the invention results in the enrichment of the substrate in S-propylene glycol alkyl (or aryl) ether acetate, as primarily the R form is converted to the product, and in the enrichment of the product in R-propylene glycol alkyl (or aryl) ether, as the S form is not as rapidly converted to the product. Thus, in these embodiments, at the end of the hydrolysis reaction, the two primary enantiomers are S-propylene glycol alkyl (or aryl) ether acetate and R-propylene glycol alkyl (or aryl) ether.

In other embodiments, the reaction catalyzed is transesterification, in which a propylene glycol alkyl (or aryl) ether is esterified with an acyl group. In the transesterification reaction, the enzyme also enantioselectively acylates one isomer; this results in the enrichment of the acylated product of this isomer, and in the enrichment of the substrate in the other isomer, which is not as rapidly converted to the product. In particular embodiments, when the enzyme is CAL-B and the substrate a racemate of propylene glycol alkyl (or aryl) ether and an acyl donor, the process of the invention results in the enrichment of the substrate in S-propylene glycol alkyl (or aryl) ether, as primarily the R form is converted to the product, and in the enrichment of the product in R-acyl propylene glycol alkyl (or aryl) ether, as the S form is not as rapidly converted to the product Thus, at the end of the transesterification reaction, the two primary enantiomers are S-propylene glycol alkyl (or aryl) ether and R-acyl propylene glycol alkyl (or aryl) ether.

Thus, in some embodiments, the present invention provides a process for resolving a racemic mixture of propylene glycol alkyl (or aryl) ether acetates comprising contacting in a reaction mixture of a racemate of the propylene glycol alkyl (or aryl) ether acetates an effective amount of the enzyme catalyst hydrolase, whereby one isomer of the racemate is enantioselectively hydrolyzed to the corresponding propylene glycol alkyl (or aryl) ethers. In some embodiments, the enzymatic catalyst is the lipase *Candida antarctica* lipase B (CAL-B). Additional information about particular and preferred embodiments of the process of the present invention for resolving a racemic mixture of propylene glycol alkyl (or aryl) ether acetates by enzymatically catalyzed hydrolysis is provided below.

In other embodiments, the present invention provides a process for resolving a racemic mixture of propylene glycol alkyl (or aryl) ethers comprising contacting in a reaction mixture of a racemate of the propylene glycol alkyl (or aryl) ethers and an acyl donor an effective amount of the enzyme catalyst hydrolase whereby one isomer of the racemate is enantioselectively esterified to the corresponding propylene glycol alkyl (or aryl) ether acylates. The word "acyl donor" is used generically, as the acyl donor can be replaced by other suitably reacting compounds leading to the formation of other esters; as a non-limiting example, transesterification in the presence of vinyl propionate leads to the formation of propionyl esters. In some embodiments, the enzymatic catalyst is the lipase *Candida antarctica* lipase B (CAL-B). Additional information about particular and preferred embodiments of the process of the present invention for resolving a racemic mixture of propylene glycol alkyl (or aryl) ether by enzymatically catalyzed transesterification is provided below In resolving a racemate by either hydrolysis or transesterification as described above and below, the reaction, or conversion of substrate to product, can be monitored by a number of well-known means; preferred methods include analysis of reactants and products by gas-chromatography (GC), of which several different methods are described in the examples (see Example 1). The yield of the product is expressed as the percentage of the substrate converted to product; this percentage is typically expressed on a molar basis, though it can also be expressed on a weight or volume basis. For any one particular enantiomer in an ideal racemic mixture, the theoretical maximum yield is 50% (when expressed on a molar basis); this represents the conversion of all of one enantiomer to product, and none of the other. However, for any particular reaction, the theoretical maximum yield is 100%, which is the conversion of all of the substrate to the product. The purity of the product or of the remaining substrate at a particular point in the reaction is expressed as the enantiomeric excess, or ee. The ee represents the enantiomeric enrichment of the product or of the substrate, and the theoretical maximum is 100%. The reaction conditions are optimized to achieve as close to the theoretical maximal yields and ee for a particular enantiomer while effecting substrate conversion on an efficient and cost-effective basis. Optimal reaction conditions would allow 50% conversion and result in the formation of enantiopure products (greater than 99% ee). Conditions allowing 40-50% conversion and resolution of one or the other products in high enantiopurity are also desirable. Recovered products which are enriched in one or the other enantiomer, but not homochiral, can be utilized as substrate for sequential resolution to give desired enantiopurity.

The following descriptions provides additional information about particular and preferred embodiments of the present invention.

Enzymatic Catalyst

In some embodiments of the present invention, which provide a method for resolving a racemate of propylene glycol alkyl (or aryl) ether acetate, the enzymatic catalyst for the resolution of a racemate of a propylene glycol alkyl (or aryl) ether acetate is a hydrolase which enantioselectively hydrolyses one isomer of the racemate; preferably, enantioselective hydrolysis results in high enantiomeric purity of either the product or the starting material. Typically, high enantiomeric purity of the product is obtained at less than 50% conversion of the substrate to product (or hydrolysis of the acetate), whereas high enantiomeric purity of the substrate is obtained at greater than 50% conversion. Preferably, enantiomeric purity of the glycol ether product is greater than about 55% ee, more preferably it is greater than about 70% ee, even more preferably it is greater than about 80% ee or 85% ee, and most preferably it is greater than about 95% ee or 98% ee. In preferred embodiments, the enzymatic catalyst hydrolyzes the R-isomeric acetate.

The hydrolase is either a lipase or esterase. Both lipases and esterases catalyze the hydrolysis of esters, and in particular carboxylic acid esterases. Exemplary hydrolases are listed in Tables 1-5, and include but are not limited to *Candida antarctica* lipase B, *Pseudomonas* sp. lipoprotein lipase, *Pseudomonas* sp. lipase, *Pseudomonas cepacia* lipase, and esterases. In some preferred embodiments, the hydrolase is a lipase, which preferentially catalyze hydrolysis of water insoluble esters.

In other embodiments of the present invention, which provide a method for resolving a racemate of propylene glycol alkyl (or aryl) ether, the enzymatic catalyst for the resolution of a racemate of a propylene glycol alkyl (or aryl) ether is a hydrolase which enantioselectively transesterified one isomer of the racemate in the presence of an acyl donor, preferably, enantioselective transesterification results in high enantiomeric purity of either the product or the starting material. Typically, high enantiomeric purity of the product is obtained at less than 50% conversion of the substrate to product (or esterification of the glycol ether), whereas high enantiomeric purity of the substrate is obtained at greater than 50% conversion. Preferably, enantiomeric purity of the glycol ether acylate product is greater than about 55% ee, more preferably it is greater than about 70% ee, even more preferably it is greater than about 80% ee or 85% ee, and most preferably it is greater than about 95% ee or 98% ee. In preferred embodiments, the enymatic catalyst transesterifies the R-isomeric ether.

The hydrolase is either a lipase or esterase. Both lipases and esterases catalyze the hydrolysis of esters, and in particular carboxylic acid esterases. Exemplary hydrolases are listed in Tables 1-5, and include but are not limited to *Candida antarctica* lipase B, *Pseudomonas* sp. lipoprotein lipase, *Pseudomonas* sp. lipase, *Pseudomonas cepacia* lipase, and esterases. In some preferred embodiments, the hydrolase is a lipase, which preferentially catalyze hydrolysis of water insoluble esters.

It is not necessary that the same enzyme be utilized in different embodiments of the present invention. Thus, one enzyme can be used for resolution of a racemate of glycol ether acetates by enantioselective hydrolysis, and a different enzyme can be used in resolution of a racemate of glycol ethers by enantioselective transesterification. In some embodiments of the present invention, the enzymatic catalyst is the lipase *Candida antarctica* lipase B (CAL-B). In different embodiments of the present invention, this enzyme is utilized in both hydrolysis and transesterification reactions.

*Candida antarctica* lipase B (CAL-B) can be isolated from *Candida antarctica* cells following published procedures (Patkar et al. (1993) Ind J. Chem., Sect. B 32B:76-80) or can be obtained from commercial sources (e.g., SP 525 from NOVO Nordisk; CHIAZYME.RTM. L-2.lyo from Roche Molecular Biochemicals) and used as catalyst without any pretreatment CAL-B can also be immobilized in a polymer matrix, on a soluble or insoluble organic support (e.g. NOVOZYM.RTM. 435 from Novo Nordisk; Chirazyme L-2, c.-f., lyo, (carrier 1) from Roche; Chirazyme L-2, c.f., C2 (carrier 2) from Roche), or on an insoluble inorganic support which simplifies catalyst recovery for reuse; these immobilization methods have been widely reported and are well-known to those skilled-in-the-art. Membrane separation of the soluble enzyme from the reaction mixture may also be employed.

Lipases with a substrate activity and enantiospecificity similar to that of CAL-B can also be employed in the present invention, including genetically modified CAL-B. In other embodiments, the enzymatic catalyst is obtained from genetically-engineered whole-cell transformants which express CAL-B or other suitable lipases or esterase, or from preparations obtained from such transformants by methods well-known in the art Resolution by Hydrolysis.

Different parameters of a hydrolysis reaction for the resolution of a racemate of a glycol ether, and in particular of a propylene glycol alkyl (or aryl) ether acetate, can be evaluated and optimized (see Examples 3-5). The hydrolysis reaction occurs in a reaction mixture, which is a combination of enzyme catalyst and a racemic substrate in which the enzyme catalyzes an enantioselective hydrolysis reaction converting the substrate to a product; more than one substrate or more than one product may be present. Additional components may also be present in a reaction mixture. Reaction conditions are optimized depending upon the relative importance of the different reaction parameters, and the desired values of the different parameters which are to be achieved during a reaction. Non-limiting examples of different parameters include which enantiomer is to be resolved, and to what yield and degree of purity, how much racemate is to be resolved or how much resolved enantiomer is desired, the desired duration of the reaction, and the amount of enzymatic catalyst to be added. Thus, in some embodiments, optimized or near optimized conditions for enantioselective hydrolysis of a racemate of PMA are used to achieve high substrate loading resulting in high purity of resolved enantiomers using a low concentration of enzyme. By "substrate loading" it is meant the initial amount or concentration of substrate present in a reaction mixture. Typically, conversions are about 30% to about 50%, and enantiomer purity of the hydrolyzed product is at least about 70% ee, preferably at least about 80% ee, more preferably at least about 90% ee, and even more preferably at least about 95% ee. Ideally where CAL-B exhibits high selectivity, desirable conditions allow 50% yield and >99% ee of resolved substrate and product. Frequently, the enantiomer purity of the substrate is also high, but generally not as high as that of the product; higher enantiomeric purity of the substrate is typically obtained at conversions of greater than 50%. Note that under the reaction conditions of the present invention, hydrolysis is not a reversible reaction; that is, the product of hydrolysis does not undergo transesterification under predominantly aqueous reaction conditions (or even under conditions of greater than about 10% water). The remaining propylene glycol alkyl (or aryl) glycol acetate (unconverted substrate) does not serve as an acyl donor for the hydrolyzed glycol ether product.

In some embodiments, the racemates resolved by a hydrolysis reaction are glycol ether acetates, and in particular propylene glycol alkyl (or aryl) ether acetates; exemplary glycol ethers are described by formula I above. Non-limiting examples of propylene glycol alkyl (or aryl) ether acetates are illustrated in FIG. 1. In other embodiments, the racemates resolved are glycol ether butyrates, and in particular propylene glycol alkyl (or aryl) butyrates, and glycol ether propionates, and in particular propylene glycol alkyl (or aryl) propionates.

In different embodiments, the concentration of the substrate racemates vary from about 0.5% to about 50% v/v; preferably, the concentration of the substrates is greater than about 10% v/v. The most effective concentration of any particular acylated propylene glycol alkyl (or aryl) ether (e.g., PGAEA) will vary, depending upon the other conditions of the reaction mixture, and depending upon the desired final conversion and purity of either the product or remaining substrate at the end of the reaction. However, the following concentrations have been found to be effective (expressed as % v/v): PMA, about 25% to about 40%, preferably about 25% in an aqueous reaction, and about 10% in a biphasic reaction; PEA, about 0.5% to about 50%, preferably about 20 to about 25% in an aqueous reaction; PPhA, about 15% to about 50%, preferably about 10 to about 25% in an aqueous reaction; PnPA, PiPA, PnBA, about 0.5% to about 50%, preferably about 10 to about 25% in an aqueous reaction.

The amount of an enzyme catalyst preparation (either unimmobilized or immobilized) in a reaction mixture (mg/ml) is chosen to obtain the desired rate of reaction, and is dependent on the specific activity of the preparation of enzyme catalyst. In some embodiments, the amount of unimmobilized CAL-B (as crude enzyme preparation, not purified protein) in the hydrolysis reactions of the present invention can range from about 0.001 to about 5 mg/ml of reaction mixture, but typically ranges from about 0.5 mg to abut 2 mg of CAL-B per ml of total reaction volume, and is most preferably from about 1 mg to about 2 mg of CAL-B per ml of total reaction volume.

In other embodiments, the amount of immobilized CAL-B (as crude enzyme preparation, not purified protein) in the hydrolysis reactions of the present invention can range from about 0.1 mg to about 1 g per ml of reaction mixture, and typically ranges from about 0.5 mg to about 0.5 g of immobilized CAL-B per ml of reaction mixture, preferably from 1 mg to 200 mg of CAL-B per ml of reaction mixture. In the case of immobilized CAL-B, resolution can be achieved by adding the enzyme to the reaction mixture in a reaction vessel (such as a screw-capped reaction vial or reactor); resolution can also be achieved by passing a reaction mixture containing the racemic substrates through a column containing the immobilized enzyme, or using membrane reactors allowing diffusion of a reaction mixture with retained enzyme. Immobilized enzyme can also be recycled, for use in multiple reactions, as is described further below.

In some embodiments, the reaction medium, or the solution in which an enzyme catalyst and at least one substrate are combined, is aqueous; in other embodiments, the reaction medium is biphasic. An aqueous reaction medium, or the aqueous component of a biphasic medium, is preferably buffered. Maintaining the initial pH of the reaction mixture can be achieved by including an appropriate buffer having a pKa within approximately one pH unit of the desired pH of the reaction mixture and at a sufficient concentration. For a reaction pH of 5.0, 6.0, and 7.0, an acetate, citrate-phosphate and phosphate buffer, respectively, can be employed; the choice of buffer is not limited to these examples. The reaction may also be run in the absence of added buffer, where the pH of the reaction mixture is monitored over the course of the reaction and acid or base added to maintain the pH of the reaction mixture at the desired value. The concentration of the buffer can also vary, although values of about 25 mM to about 200 mM are typical. The pH of the reaction can vary from about 3 to about 8.5; preferably, the pH is about 7.

A biphasic reaction medium includes an aqueous phase (as described above) and a solvent which is immiscible in an aqueous phase and which is present in addition to the substrates (which are themselves solvents). Thus, a biphasic reaction medium comprises two immiscible solvents, which separate into two phases. Although it is not necessary to understand the underlying mechanism of the reaction mixture, and although the invention is not intended to be limited by the following hypothesis, it is thought that although the aqueous phase initially contains the dissolved enzyme, the enzyme is active at the interface between the aqueous phase and an immiscible substrate-containing organic phase. The reaction can also be run in a reaction mixture which consists primarily of an organic solvent to which is added at least the minimal amount of water required for both the hydrolysis reaction and for maintaining enzyme activity. In addition, the reaction can also be run using a single phase aqueous mixture comprising water and a polar organic solvent miscible with water.

Various solvents may be employed for a biphasic reaction; examples include but are not limited to hexane and toluene. The concentrations of these solvents may also vary, as for example from 25% to 65% (v/v). Preferably, the solvents are present at about 40% to about 50% (v/v). Polar organic solvents such as methanol, dioxane or acetone can also be added at lower concentrations (e.g., 0.25% to 10% v/v) to enhance enantioselectivity.

Preferably, the reaction mixture is aqueous. One advantage of an aqueous mixture is that hydrolysis appears to be favored.

In most embodiments, the temperature of the hydrolysis reaction is chosen to optimize the reaction rate, the stability of the enzyme catalyst activity, enantioselectivity of the enzyme and the stability of the substrates. For example, the effect of incubation temperature was examined between 30° C. and 50° C. (in 5° C. increments) in aqueous reaction mixtures containing 25% (v/v) PMA and 1.0 and 0.5 mg/ml CAL-B (Chirazyme L-2 lyo). Under these conditions, PMA hydrolysis was most rapid at 40° C. and final enantiopurity was not affected at this temperature. However, reactions incubated at 35° C. with the lower enzyme concentration showed sustainable catalysis for a longer duration and resulted in higher (S)-PMA enantiopurity than reactions incubated at 40° C. Incubation at 50° C. inactivated the enzyme within 5 hours. Assuming that measured rates were independent of temperature-induced differences in substrate solubility, the results indicate that the temperature optimum for CAL-B (Chirazyme L-2 lyo) was approximately 40° C., but that greater enzyme stability was observed at 35° C. in aqueous reaction mixtures. Thus, the preferred temperature is about 35° C. to 40° C., with a temperature of about 37° C. typically used.

In most embodiments, the reaction mixture is incubated with agitation; means to accomplish such agitation include rotary shaking, mechanical stirring, or impeller driven agitation.

At a given operational temperature, the reaction rate depends upon the amount of lipase present in the reaction. Therefore, the time of the reaction depends upon the amount of lipase added. Thus, for example, reaction mixtures containing CAL-B (Chirazyme L-2 lyo, greater than 120 U/mg lyo.) at concentrations of 1.0, 0.5, 0.1, 0.05, 0.01, 0.001 mg/ml were used to determine the minimum activity Units required to effect enantioselective hydrolysis of 10% (v/v) PMA under biphasic conditions with 50% hexane. After 2 hours, reactions containing enzyme loadings of 1.0 and 0.5 mg/ml had resolved the (S)-enantiomer of PMA to greater than 98% ee in near theoretical yield. By 72 hours, reactions containing enzyme loadings of at least 0.01 mg/ml resolved (S)-PMA in greater than 99.5% ee. However, the extended incubation led to further hydrolysis of the remaining (S)-PMA substrate, which reduced the yield of (S)-PMA in reactions containing enzyme at 0.5 and 1.0 mg/ml to approximately 25% and 10%, respectively (based on maximum theoretical of 50%).

In similar experiments, enantioselective hydrolysis was examined as a function of enzyme concentration in aqueous reaction mixtures containing 25% (v/v) PMA. Results indicated that CAL-B (Chirazyme L-2 lyo.) at concentrations of 2.0, 1.0 and 0.5 mg/ml effected complete resolution of (S)-PMA to greater than 99% ee within 4, 6 and 24 hours, respectively (see Example 4). In contrast, a reaction mixture containing 0.1 mg/ml CAL-B (Chirazyme L-2 lyo.) partially resolved (S)-PMA (<60% ee) within 30 hours.

Therefore, in most embodiments, the time of the reaction varies from about 2 to about 72 hours, but is preferably from about 4 to about 24 hours; for PMA, the reaction time is more preferably from about 4 to about 6 hours, whereas for PEA, the reaction time is more preferably from about 8 to 10 hours.

In some embodiments, the hydrolysis reaction is carried out in a single batch reaction; in other embodiments, the hydrolysis reaction is carried out in a continuous process.

Resolution by Transesterification.

Different parameters of the transesterification or acylation reaction for the resolution of a racemate of a glycol ether, and in particular of a propylene glycol alkyl (or aryl) ether, can be evaluated and optimized (see Examples 6-7 and 11). The transesterification reaction occurs in a reaction mixture, which is a combination of enzyme catalyst and racemic substrate in which the enzyme catalyzes a transesterification reaction converting the substrate to an acylated product; more than one substrate or more than one product may be present. Additional components may also be present in a reaction mixture. Reaction conditions are optimized depending upon the relative importance of the different reaction parameters, and the desired values of the different parameters which are to be achieved during a reaction. Non-limiting examples of different parameters include which enantiomer is to be resolved, and to what yield and degree of purity, how much racemate is to be resolved or how much resolved enantiomer is desired, the desired duration of the reaction, and the amount of enzymatic catalyst added. Typically, yields are about 30% to about 50%, and typically enantiomer purity of the acylated product is greater than about 80% ee, more preferably greater than about 90% ee, and even more preferably greater than about 95% ee. Frequently, the enantiomer purity of the substrate is also high, but generally not as high as that of the product; higher enantiomeric purity of the substrate is typically obtained at conversions of greater than about 50%. However, both the yields and the purity depend upon which enantiomer is resolved, and upon the reaction conditions. This is due in part because of the potential hydrolysis or alcoholysis of the formed product. In other words, the products of transesterification, propylene glycol alkyl (or aryl) ether acetates, can be hydrolyzed or de-esterified by a hydrolase enzymatic catalyst to the corresponding propylene glycol alkyl (or aryl) ethers, which are again substrates for the transesterification reaction (which would, however, be limited by the availability of the substrate). Thus, the reverse reaction degrades the enantiometric purity of the remaining starting material thereby lowering the efficiency of the resolution. The interaction of yield and purity are described in further detail below.

The amount of an enzyme catalyst preparation (either unimmobilized or immobilized) in a reaction mixture (mg/ml) is chosen to obtain the desired rate of reaction, and is chosen to the desired rate of reaction, and is dependent upon the specific activity of the preparation of the enzyme catalyst. In some embodiments, the amount of unimmobilized CAL-B (as crude enzyme preparation, not purified protein) in the transesterification reactions of the present invention can range from about 0.001 to about 50 mg/ml, but typically ranges from about 0.5 mg to abut 2 mg of CAL-B per ml of total reaction volume, and is most preferably from about 1 mg to about 2 mg of CAL-B per ml of total reaction volume. In fact, adjusting enzyme loading was shown to be an effective method of increasing product optical purity through reaction engineering.

In other embodiments, the amount of immobilized CAL-B (as crude enzyme preparation, not purified protein) in the transesterification reactions of the present invention can range from about 0.1 mg to about 1 g, and typically ranges from about 1 mg to about 0.5 g of immobilized CAL-B per ml of reaction mixture, preferably from about 2.5 mg to about 200 mg of CAL-B per ml of reaction mixture. In the case of immobilized CAL-B, resolution can be achieved by running the reaction in batch mode, such as by adding the enzyme to the reaction mixture in a reaction vessel (such as a screw-capped reaction vial or reactor), or by using a membrane to retain the enzyme; resolution can also be achieved in a continuous mode by passing the reaction mixture containing the racemic substrates through a column containing the immobilized enzyme. When used in batch mode, the enzyme can be recycled, as is described further below.

The reaction medium for the transesterification is preferably aprotic, or non-aqueous; thus, in different embodiments, the medium comprises at least one solvent or ionic liquid, and preferably comprises at least one organic solvent which is preferably non-polar, and even more preferably which is an organic solvent. Examples of such solvents include but are not limited to toluene and hexane, and ionic liquids. Further examples of solvents are the substrates propylene glycol alkyl (or aryl) ethers, because they themselves are organic solvents, and the products as they are formed, the corresponding acylated propylene glycol alkyl (or aryl) ethers, which are also organic solvents. The non-substrate and non-product solvents are referred to as co-solvents. Ionic liquids include, as non-limiting examples, 1-ethyl-3-methylimidazolium (e.g., [EMIM]-[BF4]) and, 1-butyl-3-methylimidazolium (e.g., [BMIM]-[PF6]), where BF4 and PF6 serve as counter ions, particularly anion components. (Ki, K.-W., et al. 2001. Biocatalysis in ionic liquids: markedly enhanced enantioselectivity of lipase. Organic Letters, 3:1507-1509) and (Lau, R. M., et al. 2000 Organic Letters, 2:4189)

In other embodiments (see Examples 9-11), (±)-1-methoxy-2-propanol acetate (PMA) is used as an acyl donor for enantioselective acylation in an enzymatic transesterification based resolution process. The use of racemic chiral glycol ethers as acyl donors allows for the simultaneous resolution of acylating agent as well as resolved acetate and alcohol or amine enantiomer substrates. Thus, in addition to the enzymatically resolved substrate, the byproducts of the acyl donor also represent resolved chiral glycol ethers and glycol ether acetate compounds. The usefulness of PMA and other non-activated PGAEA compounds as acyl donors for for enantioselective acylation in an enzymatic transesterification based resolution process has been shown through reaction-stripping experiments with PMA as a non-activated acyl donor.

The substrates resolved by a transesterification reaction are a racemic mixture of glycol ethers, and in particular propylene glycol alkyl (or aryl) ethers and acyl donors; exemplary glycol ether acetates are described by formula I above. Non-limiting examples of propylene glycol alkyl (or aryl) ethers are shown in FIG. 1. Acyl donors include activated acyl donors, such as activated esters (including but not limited to trifluoroethyl butyrate, S-ethyl thio-octanoate, and biacetyl mono-oxime acetate,) enol esters (but not limited to vinyl acetate, isopropenyl acetate, and 1-ethoxyvinyl acetates, and diketene), and anhydrides (acetic acid anhydride, lactide, and succinic acid anhydride). Use of enol esters and acid anhydrides as acyl donors results in practically irreversible acylation. This is particularly useful for the resolution of alcohols because the reverse reaction results in lower enantiomeric purity of the remaining starting material. In some embodiments, acyl donors include but are not limited to vinyl acetate, vinyl propionate, 2,2,2-trichloroethyl acetate, 2,2,2-trifluoroethyl acetate, butyl acetate, ethylphenyl acetate, isopropenyl acetate, ethyl methoxyacetate, 1-ethoxyvinyl acetate, diketene, trifluoroethyl butyrate, acetic acid anhydride, lactide, and succinic acid anhydride. Initial experiments demonstrated that with the first two acyl donors described, conversion of all propylene glycol alkyl (or aryl) ethers examined was most rapid with vinyl acetate as the acyl donor. Although it is not necessary to understand the mechanism to practice the invention, and the present invention is not limited by the underlying mechanism, it is thought that the rapid reaction is because these esterification agents are enol esters, for which, the product alcohol tautomerizes to a carbonyl compound, thereby driving the reaction and eliminating potential product inhibition by alcoholysis. Acyl donors also include non-activated acyl donors, such as ethyl acetate and a racemic chiral compound such as, for example, racemic 1-methoxy-2-propanol acetate (PMA). Additional non-limiting examples of non-activated acyl donors include butyl acetate (BA), ethyl phenyl acetate (EPA), ethyl acetate (EtA), and PnPA In this case, it is advantageous to remove the byproduct alcohol from the reaction mixture to drive the reaction forward and achieve increased conversion of the reagent. We have discovered that unless byproduct alcohol is removed, the reaction can become equilibrated such that forward and back reaction rates are essentially the same, and conversion reaches a limiting value.

Examples of byproducts include ethanol formed from ethyl acetate, and the general class of chiral secondary alcohols formed from their corresponding chiral acetates. The reaction vessel may be operated in a semi-batch mode of operation involving periodic removal of vapor from the reaction vessel to remove the byproduct alcohol. The operation may also involve periodic addition of reagents in order to replace reagent removed in the vapor stream. The invention may also be carried out continuously. This involves continuous removal of vapor from the reaction vessel and continuous addition of reagents. The reaction may also be carried out in combination with a distillation tower. This involves feeding reagents to a reactor to advance conversion and then on to a distillation tower to remove byproduct alcohol and return an alcohol-lean reagent stream to the reactor. The combination of reaction with vapor removal or distillation allows stripping of byproduct alcohol from the reaction mixture to drive the reaction to a higher level of conversion than would be possible without removal of byproduct alcohol.

A non-reactive stripping agent may also be added to the reaction mixture to facilitate the removal of byproduct alcohol. For example, the use of stripping agents such as nitrogen or n-hexane may be benefical to the overall process by allowing removal of vapor at a temperature below the boiling point of the reaction mixture at a given operating pressure. Whether it is beneficial to use a stripping agent and the most appropriate choice of stripping agent will depend upon the composition of the reaction mixture, the volatility of the by-product alcohol, and any constraints on the operating temperature and pressure due to thermal sensitivity of the catalyst or practical limits as to how low in pressure the process equipment may be operated. The general use of stripping agents to facilitate removal of light components from liquid feeds is well known in the art.

In a different embodiment, the concentration of the substrate racemates can vary from about 0.5% to greater than about 85%, v/v; preferably, the substrate concentration is greater than about 5%, and most preferably, the substrate concentration is as high as possible while still accommodating a sufficient amount of acyl donor required to achieve the desired extent of conversion. It has been discovered that the reaction medium can be about 100% (v/v) substrates, which includes the acyl-acceptor (for example, propylene glycol alkyl (or aryl) ether) and the acyl-donor; it is believed that this is because these substrates are themselves organic solvents, and because it is preferred that the reaction medium be aprotic or non-protic. For example, the concentration of the acyl acceptor (a propylene glycol ether alkyl (or aryl) ether) can vary from about 30% (v/v) to about 70% v/v, with the remaining volume to about 100% total reaction mixture volume (or about 70% (v/v) to about 30% (v/v)) comprising the acyl donor (e.g., vinyl acetate). This discovery provides a new approach to conducting a transesterification reaction. This approach also offers several advantages. One is that the reaction can occur at very high substrate concentrations, and produces product at very high concentrations. Another is that the resolved enantiomers (products and substrates) need not be extracted, since they are themselves organic solvents; therefore, following separation of immobilized biocatalyst from the reaction mixture, the resolved enantiomers can be distilled directly from the remaining reaction mixture (or reaction matrix), resulting in more rapid recovery of the resolved enantiomers, which is thus more efficient and less expensive.

The presence of water in the reaction mixture (for example, when added to the mixture from about 1% (v/v) to about 3% v/v) appears to slow the rate of reaction. However, the effect of the water may be a useful way to control the extent of the reaction. On the other hand, the presence of water in the reaction mixture appears to result in the activity of the competing enzymatic reaction, hydrolysis of the acylated products. Thus, the absence of water in the reaction mixture appears to greatly decrease the probability of hydrolysis of the acylated products. Although water is believed to be required for the lipase to function, there appears to be sufficient amounts present in either most commercial organic solvents or most commercial preparations of the enzyme so that adding additional water to the reaction mixture is not usually necessary.

It has also been discovered that it is possible to control product yield and resolved enantiomeric purity by conducting the transesterification reaction in a reaction medium of substrate solvents only, and by controlling the ratios of the two substrates of the reaction, the acyl acceptor or PGAE and the acyl donor. Thus, the present invention also provides a method to control product yield and resolved enantiomeric purity by controlling an enzymatically catalyzed transesterification reaction in a reaction medium of substrate solvents only, and by controlling the ratios of the two substrates of the reaction, the acyl acceptor or PGAE and the acyl donor. The objective is to have as high a starting concentration of an acyl-acceptor (e.g., a PGAE) as possible, without having the concentration of the acyl-donor (e.g., a vinyl acetate) be limiting; meeting this objective would result in the highest amount of resolved acylated product or remaining substrate possible. This control is based upon the following assumptions. Because the substrates are a racemic mixture, the theoretical maximum conversion of either enantiomeric to its corresponding product (an acylated PGAE) is 50%. However, the catalytic hydrolase (preferably a lipase or an esterase) is believed to acylate both enantiomers as substrates, although it preferentially acylates one enantiomer (i.e., it enantioselectively acylates one enantiomer, as for example, CAL-B enantioselectively acylates the R-isomer). Thus, at 50% total substrate conversion, at least some small fraction of the product is likely to be the other isomer, which results in a decreased purity of the first isomeric product. Thus, at a slightly lower substrate conversion (slightly less than 50%, e.g., about 45%), less of the second isomeric product is formed, resulting in a higher purity of the first isomeric product which is nonetheless produced at high yield. Conversely, at 50% total substrate conversion, a small but possibly significant proportion of the first isomeric substrate has not been converted. Thus, at a slightly higher substrate conversion (slightly higher than 50%, e.g. about 55%), less of the first isomeric substrate remains, resulting in a higher purity of the second substrate which is nonetheless present in a high yield. Thus, in some embodiments of the present invention, the extent of conversion of the racemic substrate can be controlled by the ratio of the two substrates, the acyl-acceptor (or the racemic substrate) and the acyl-donor. Thus, a molar ratio of acyl-acceptor (i.e., a PGAE) to an acyl donor (e.g., a vinyl acetate) of 2:1 could theoretically result in a total substrate conversion of about 50%; the ratio of acyl-acceptor to acyl-donor is selected to permit one mole of acyl donor to selectively react with one of the two moles of the acyl-acceptor, or just about half of the racemic substrate. By varying this ratio, it is possible to control the degree of substrate conversion, thus enriching either the product in the first isomer or the remaining substrate in the second isomer to high degrees of purity at high yields. For example, purities of greater than about 90% ee of the desired racemate (either product or remaining substrate) could be achieved with substrate conversions of about 35% to about 65%.

By using the molecular weights and densities of the substrates (glycol ether and acyl donor), it is possible to calculate the volumes required to achieve different molar ratios which are calculated to achieve desired extents of conversion (optimal yields) and enantiopurities, assuming completely selective transesterification; these optimal yields and theoretical enantiomer purities are then the expected values. The calculated volumes of the substrates are then combined with the enzymatic catalyst under standard reaction conditions (as described further below), and the degree of substrate conversion and relative purity of either the first isomeric product or the remaining second isomeric substrate monitored. The experimental or actual observed yields and purities sometimes vary from the expected values. For example, in a reaction of PPh with vinyl acetate in the presence of CAL-B, a 70/30 (v/v) ratio is expected to result in about 75% substrate conversion; however, a conversion of approximately 45% is typically actually observed with (S)-PPh and (R)-PPhA purities of about 80% ee to greater than about 98.5% ee, respectively. A change of the substrate ratio to 76/24 (v/v) is expected to result in about 55% substrate conversion; however, a conversion of about 40% is typically actually observed with (R)-PPhA purity of greater than about 98% and (S)-PPh purity of about 60% ee. In summary, the present invention provides an effective method to control the extent of substrate conversion for the generation of desired products in high % ee by limiting the amount of the acyl-donor.

Thus, in some embodiments, a method of controlling substrate conversion is to first determine optimal yield of converted (or acylated) substrate and enantiometric purity of either converted or unconverted substrate, as assessed by chiral GC or HPLC analysis (as, for example, is described in the Examples), then determine the appropriate molar ratios of the substrates to achieve these yields (for example, providing acyl donor in amounts limiting conversion to 45% or 55%) then calculate the volumes of the substrates to achieve this molar ratio, based on the molecular weights and densities of the substrates, and then combine these calculated substrate volumes with the enzymatic catalyst and incubate the resulting reaction mixture under standard reaction conditions. The product yield and enantiomer purity are monitored, and if necessary, the ratio of the substrates is adjusted, based upon the observed yield and enantiomer purities, to achieve the desired conversion extent (yields) and optimal enantiomer purities.

Therefore, in different embodiments, the concentration of the substrates can vary from about 10% to about 90% (v/v), where the combination of the percentage of the acyl-acceptor and acyl-donor total about 100% (v/v) of the total reaction mixture. Alternatively, in other embodiments, the concentration of the substrates can vary from about 20% to about 80% (v/v), where the combination of the percentage of the acyl-acceptor and acyl-donor total less than about 100% (v/v); in this case, the remaining volume is supplied as an organic solvent.

The temperature of the transesterification reaction is chosen to optimize the reaction rate, the enantioselectivity, the stability of the enzyme catalyst, and the stability of the substrates. For example, reducing the reaction temperature results in increased enantioselectivity of the lipase CAL-B for transesterification-based resolution of PM. Thus, although rates of resolution were slower, lowering reaction temperature was an effective way to increase product optical purity. This effect was demonstrated at temperatures ranging from −20° C. to 30° C. Thus, in different embodiments, the preferred temperature will depend upon the particular substrate; for PPh esterification, the preferred reaction temperature was about 20° C. to 30° C., with a temperature of about 25° C. typically used.

The reaction is conducted with agitation; means to accomplish such agitation include rotary shaking or impeller driven agitation.

The reaction rate depends upon the amount of lipase present in the reaction. Therefore, the time of the reaction depends upon the amount of lipase added. For transesterification, the time of the reaction varies from about 2 to about 96 hours, but is preferably from about 4 to about 72 hours, and is more preferably from about 4 to about 48 hours.

The transesterification reactions may be carried out in a single batch reaction, or in a continuous process. For example, reactors with membranes can be used to effectively retain immobilized enzyme.

There are several advantages to the transesterification reaction described above for glycol ether resolution. One is that with lipase catalyzed acylation, longer chain alkyl- and aryl-substituted glycol ethers and their acetates have limited aqueous solubility under hydrolytic resolution conditions. Moreover, lipase-based acylation in organic solvent/substrate proceeds at extremely high substrate loading, affording high volumetric productivity and eliminating the need for extraction of the reaction material prior to distillation and product isolation.

Recycling of Biocatalyst.

The enzyme catalyst utilized for both the hydrolysis and transesterification reactions can be recycled; this means that the enzyme can be recovered from a mixture in which the catalyzed reaction is complete and added to fresh reaction mix. Recovery and reuse of the enzyme is referred to as enzyme recycling; thus, recycling effects a separation of the biocatalyst from the reactants, the products, and other components of the reaction mix. Recycling the enzyme offers several advantages, including decreasing reaction costs per cycle.

Recycling the enzyme can be achieved by filtering an aqueous reaction mix, whereby the enzyme is retained by the filter. Alternatively or in addition, recycling preferably utilizes an immobilized enzyme. Immobilized enzyme can then be separated from the reaction mixture by a number of means, including but not limited to centrifugation, filtration, or by retaining it in a reactor through gravimetric sedimentation, such as by settling, draining the remaining reaction mixture from the reactor, and then adding new reaction matrix (which is a reaction mixture which does not contain any enzymatic catalyst).

For example, an immobilized form of CAL-B, Chirazyme L-2 c.-f. C2 lyo. (Roche), was capable of resolving each of the propylene glycol ether acetate substrates at up to 25% substrate loading. Immobilized CAL-B was also used to examine enantioselective hydrolysis of PPhA. The enantioselectivity for PPhA was excellent, resulting in resolution of (S)-PPhA and (R)-PPh at greater than 99% ee and approximately 50% substrate conversion at a PPhA loading of 25% v/v. Resolution was demonstrated at up to 50% substrate loading with 45% substrate conversion at 24 hours and (R)-PPh of greater than 99% ee and (S)-PPhA purity of 75% ee. However, immobilized CAL-B. catalyzed efficient resolution of both (S)-PPhA and (R)-PPh at a substrate loading of 25% (v/v) PPhA for multiple cycles of resolution.

Figure 6:
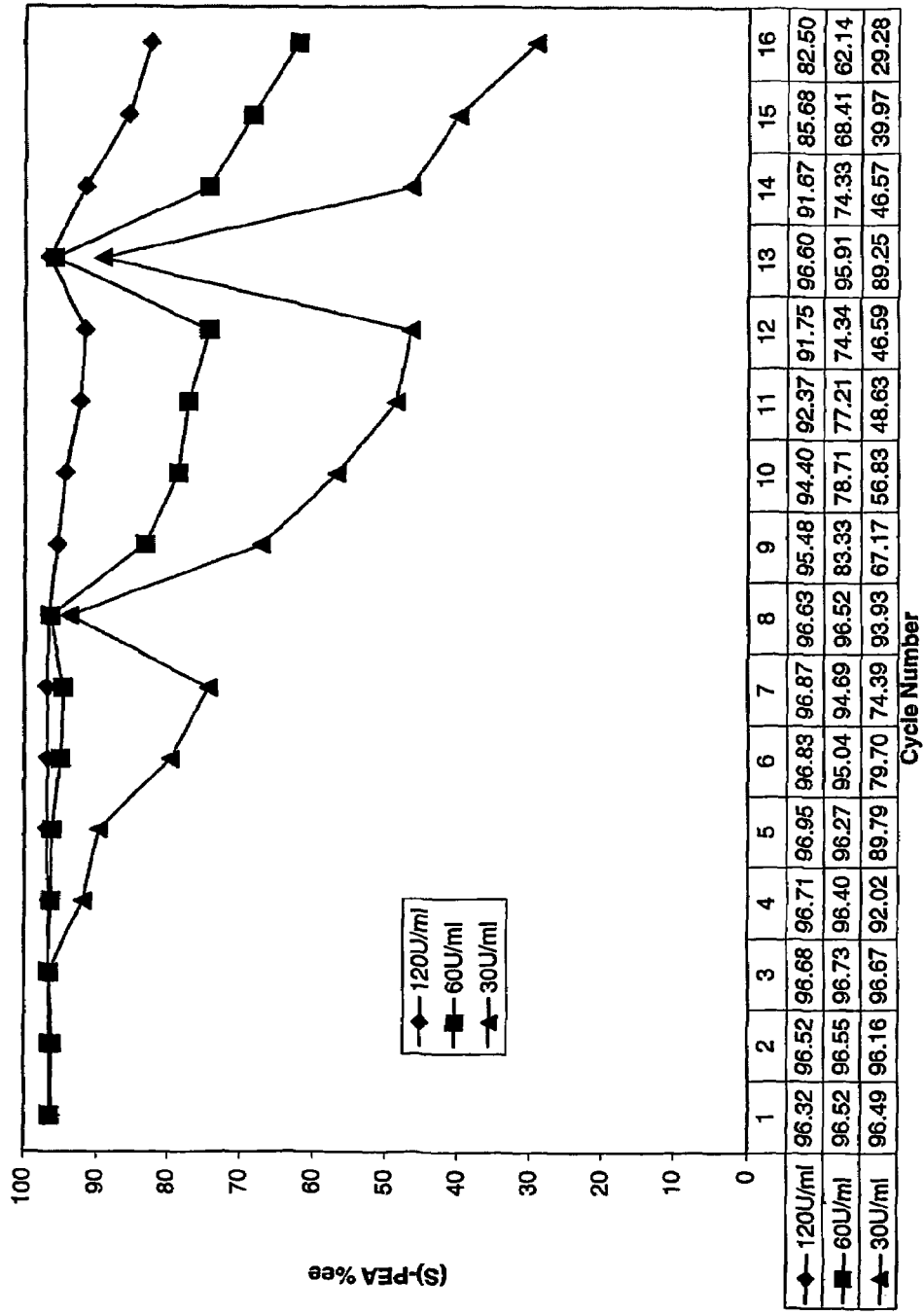
FIG. 6 shows enzyme recycle for PEA hydrolysis. The resolution of PEA (expressed and % ee) is shown as a function of enzyme cycle for three different concentrations of CAL-B; the cycle length was 24 hours, except cycle 3 (48 hours) and cycles 8 and 13 (60 hours).

In another example, the performance of Chirazyine L-2, c.-f. C2 (at enzyme loadings of 30, 60 and 120 U/ml) was examined at an experimental scale for PEA hydrolysis at 20% (v/v) substrate loading; enzyme recycle was demonstrated for more than 15 cycles (see Example 8 and FIG. 6). Resolution performance over multiple cycles was best at an enzyme loading of 120 U/ml. Enzyme recycle was also demonstrated for 30 batches (or cycles) of hydrolysis of 25% PMA using immobilized CAL-B from Roche (Chirazyme L-2, c.-f C2, lyo.) at a concentration of 26.6 mg/ml. The enantiopurity of (S)-PMA was approx. 97% ee over the course of 30 reaction cycles in experiments conducted with 20% or 25% substrate concentration.

In scale-up experiments, immobilized CAL-B (Chirazyme L-2, c.-f. C2; approximately 240 U/ml) was used for 15 recycles of enantioselective hydrolysis of 25% PMA at 1.5 liter scale. Cycle time ranged from 2.5 hours to 6 hours. Reaction parameters included a reaction temperature of 37° C., agitation (impeller speed) 200 rpm, and a pH of about 7 which was maintained by addition of 20% (w/v) sodium hydroxide. In other scale-up experiments, immobilized CAL-B (Chirazyme L-2, c.-f. C2; approximately 240 U/ml) was used for more than 30 cycles of enantioselective hydrolysis with 20% (v/v) PEA as substrate (see Example 8 and FIGS. 7 and 9). A cycle time of about 8 hours allowed resolution of (S)-PEA and (R)-PE in high enantiopurity. Additional enzyme (10% of the original loading) was provided at cycles 8, 10, 16, and 25 to maintain the desired reaction cycle time. Average product purity for 32 reaction cycles was (S)-PEA of grater than 97.9% 55 and (R)-PE of greater than 95% ee. Reaction parameters were as for PMA. Product recovery for these experiments is described below.

Recovery of Resolved Enantiomers.

Both of the resolved optically active species (glycol ether acetate and glycol ether) can be recovered and isolated from the reaction matrix by liquid-liquid extraction, thermal-activated separation, distillation, liquid-solid adsorption methods, or a combination thereof.

For example, in the first set of scale-up experiments described above, liquid-liquid extraction with methylene chloride facilitated recovery of a mixture containing (S)-PMA of greater than 99% ee and (R)-PM of about 85% ee. However, the chiral (R)-PM is water-soluble and proved difficult to recover by extraction of aqueous reaction mixtures.

In another example, in the second set of scale-up experiments described above, extraction of the reaction mixture with methylene chloride yielded a mixture of (S)-PEA and (R)-PE of 98% ee and 95% ee, respectively.

In yet other examples, material from 15 batches of PMA hydrolysis reactions and over 32 batches of PEA hydrolysis reactions are distilled to isolate the chiral glycol ethers and their corresponding antipodal acetates.

Utility of Resolved Enantiomers

The methods of the present invention provide resolved enantiomers which have many applications in the pharmaceutical (Hoff et al. (1996) Tetrahedron: Asymmetry 7:3181-3186) and agricultural industries, as noted above. For example, the resolved compounds are contemplated as possible synthons for pharma, combi-chem, and ferroelectric liquid crystal applications. They are also contemplated to improve selectivity of bioresolution by integration into chemo-enzymatic process to form diastereomeric esters (instead of racemic esters). In other applications, they are contemplated to enhance enzyme performance with respect to increasing selectivity. In other aspects, it is contemplated that these resolved compounds provide economical polar chiral solvents, which are useful as solvents or cosolvents for crystallization based "classical resolutions," as well as cosolvents for biocatalytic reactions or solvents for transesterification. In addition, these solvents might be useful for crystallization-induced dynamic resolutions (CIDR). It is further contemplated that these compounds can be used in selective or partially-selective azeotrophic distillation of chiral materials when co-distilled. In chiral chromatography, the resolved compounds are contemplated to replace simple alcohols in the mobile phase to enhance existing chiral separations, or for use as ligands for attachment to solid phases for chiral separations. Other uses may be the preparation of chiral bases (alkoxides), and the preparation of chiral Lewis acids by reaction with TiCl4. The latter might be used in selective oxidations such as the Sharpless epoxidation of olefins and the oxidation of sulfides to sulfoxides.

EXAMPLES

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (milimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); U (units of enzyme activity; typically expressed as moles of substrate converted ); ° C. (degrees Centigrade); % (percent); (v/v)(volume/volume); % C (% conversion); ee (enantiomeric excess); E (enantioselectivity)

Example 1

Materials and Analytical Methods

Substrates

P-series glycol ethers and acylates were used as substrates. This series included:

Propylene glycol methyl ether (also 1-methoxy-2-propanol, PM).

Propylene glycol methyl ether acetate (also 1-methoxy-2-propanol acetate, PMA).

Propylene glycol ethyl ether (1-ethoxy-2-propanol, PE).

Propylene glycol ethyl ether acetate (1-ethoxy-2-propanol acetate, PEA).

Propylene glycol n-propyl ether (1-n-propyloxy-2-propanol, PnP).

Propylene glycol n-propyl ether acetate (1-n-propyloxy-2-propanol acetate, PnPA).

Propylene glycol isopropyl ether (1-isopropyloxy-2-propanol, PiP).

Propylene glycol isopropyl ether acetate (1-isopropyloxy-2-propanol acetate, PiPA).

Propylene glycol n-butyl ether (1-n-butyloxy-2-propanol, PnB).

Propylene glycol n-butyl ether acetate (1-n-butyloxy-2-propanol acetate, PnBA).

Propylene glycol t-butyl ether (1-tert-butyloxy-2-propanol, PtB).

Propylene glycol t-butyl ether acetate (1-tert-butyloxy-2-propanol acetate, PtBA).

Propylene glycol phenyl ether (1-phenoxy-2-propanol, PPh).

Propylene glycol phenyl ether acetate (1-phenoxy-2propanol acetate, PPhA)

Enzymes

Different lipases, esterases, and proteases were obtained from commercial suppliers and included the ChiroScreen™ EH kit from Altus Biologics Inc. (Cambridge, Mass.), the Chirazyme® Lipases & Esterases Screening Set 2, glutaryl acylase and penicillin G amidase from Roche Molecular Biochemicals (Mannheim, Germany, US distribution via BioCatalytics Inc., Pasadena, Calif.), the ThermoCat™ QuickScreen™ Esterase Kit from Thermogen Inc. (Lemont, Ill.), the Lipase Extension Kit and recombinant *Candida antarctica* lipase type B from Fluka BioChemika AG (Buchs, Switzerland), and industrial enzyme samples from Amano Pharmaceutical Co. (Nagoya, Japan), Novo Nordisk, and Genencor International (Rochester, N.Y.). Enzymes were stored at 4° C. or at −20° C. in accordance with manufacturer's recommendations.

Chemicals and Solutions

Acetonitrile, hexane (HPLC-grade), vinyl acetate, potassium phosphate monobasic ($KH_2PO_4$, 99.0% min.) and sodium phosphate dibasic ($Na_2HPO_4$, ≧99.0%) were obtained from Fisher Scientific. (S)-Propylene oxide was from Chirex (batch T67893, Chirex order no. 607). Sorensen's phosphate buffer was prepared at the concentration specified from 29.6 mole % $KH_2PO_4$ and 70.4 mole % $Na_2HPO_4 \times H_2O$, and pH adjusted from 7.2 as needed.

The following propylene glycol alkyl/aryl ethers and their acetates were obtained from Sigma-Aldrich: PM (99.5%), PMA (99.5%), PEA (95%), PnP (99%), PnB (99%), PtB and PPh (93%, containing up to 7% di(propylene glycol) phenyl ether; DPPh). The PE, PiP, PiPA, PnPA, PnBA, PPhA, and the enantiomeric standards of glycol ethers (see asymmetric synthesis below) were prepared at The Dow Chemical Company. A non-racemic mixture of PtBA enantiomers was prepared by reacting PtB and vinyl acetate (1:2 molar ratio) in the presence of 5 mg/ml Chirazyme L-10 (Roche Molecular Biochemicals).

Asymmetric Enantiomeric Standards

In order to determine which enantiomer of a racemate was hydrolyzed or transesterified in an enzymatically catalyzed reaction, it was necessary to obtain standards of known stereochemistry to use in the analytical methods. Use of these standards then permitted correlation of the GC retention time with a particular known compound. To that end, pure enantiomers of individual members of the P-series glycol ethers and their corresponding acetates were chemically synthesized.

Initially, (S)-PM and (S)-PMA were synthesized (see Example 2), and their GC elution times determined; the relative order of elution times for the two enantiomers was determined by comparing the elution times of (S)-PM and (S)-PMA to the elution times of the corresponding racemates. Under the analytical conditions utilized, (S)-PMA eluted before (R)-PMA (at 4.1 and 4.24 minutes, respectively), and the same relative order of elution was observed for the non-acylated enantiomers, (S)-PM and (R)-PM. This relative order of elution times for the different enantiomers was extended by analogy to the other members of the P-series glycol ethers and their corresponding acetates, and utilized in the analysis of the products and remaining substrates of enzyme catalyzed reactions involving this series. Subsequently, the pure (S)-enantiomers of other members of the P-series glycol ethers and their corresponding acetates were also chemically synthesized (these included (S)-PE and (S)-PEA, (S)-PnP and (S)-PnPA, (S)-PnB and (S)-PnBA, and (S)-PPh and (S)-PPhA), and the relative elution order confirmed as correct (as noted below). Results of GC analysis indicated that the (S)-enantiomers of PE, PEA, PnP, PnPA, PnB, PnBA, PPh and PPhA correspond to the first eluting peak of the corresponding 1-alkoxy-2-propanol (or 1-alkoxy-2-propanol acetate) enantiomers observed in the resolved racemic standards.

Analytical Methods

Gas Chromatographic Methods. A Hewlett-Packard 6890 Gas Chromatograph equipped with standard capillary inlet, flame ionization detector (FID), and LEAP-CTC auto-injector (100 sample tray) was used for analyses. Five GC methods were used for analysis of samples containing different P-series substrates. The different GC methods used the same oven temperature program but contained compound calibration and integration information specific to the substrate used during screening. Briefly, the β-DEX 325 chiral capillary column (30 m×0.25 mm ID 0.25 µm film thickness) from Supelco was used for the separation. The column temperature was programmed from 70° C. to 120° C. at 10° C./min for PM and PMA, and to 150° C. for the others substrates and products. The carrier gas was helium at 18.0 psi (constant pressure). Temperatures of the injection port and detector were 200° C. and 250° C., respectively. Samples diluted 200:1 in acetonitrile or water were injected (1.0 µl) at a split ratio of 25:1. The methods were calibrated using racenic samples from Dow. Chemical or Sigma-Aldrich at concentrations ranging from 0.005 to 0.5% and displayed an $r^2$>0.99 for all the compounds.

Compound retention times, under the above conditions, are listed for the secondary alcohols and their corresponding acetates which represent the major components of the glycol ether products. The absolute stereochemistry of PE, PnP, PiP, PnB, PPh and their corresponding acetates was assigned based on the order of elution of the (S)-enantiomers, synthesized as standards, relative to the resolved racemates. In each case, the (S)-enantiomer of the secondary alcohols and their acetates eluted before the corresponding (R)-enantiomer. In the case of (±)-PM, baseline separation of enantiomers was not achieved. Under the conditions described, retention times for the compounds were: (±)-PM (2.811 min), (S)-PMA(4.104 min), (R)-PMA(4.246 min), (S)-PE (3.203 min), (R)-PE (3.248 min), (S)-PEA (4.774 min), (R)-PEA (4.936 min), (S)-PnP (4.157 min), (R)-PnP (4.224 min), (S)-PnPA (6.0 min), (R)-PnPA (6.145 min), (S)-PiP (3.629 min), (R)-PiP (3.718 min), (S)-PiPA (5.316 min), (R)-PiPA (5.448 min), (S)-PnB (5.394 min), (R)-PnB (5.484 min), (S)-PnBA (7.42 min), (R)-PnBA (7.545 min), (S)-PtB (5.559 min), (R)-PtB (5.908 min), (S)-PtBA (7.529 min) and (R)-PtBA (7.679 min).

The (±)-PM enantiomers could be chromatographically resolved on an α-Dex 120 chiral capillary column (30 m×0.25 mm ID 0.25 μm film thickness) from Supelco with helium as carrier gas at 20.0 psi (constant pressure) and oven temperature programmed from 50° C. to 150° C. at 10° C./min. Temperatures of the injection port and detector were 200° C. and 250° C., respectively and samples diluted 200:1 in acetonitrile or water were injected (1.0 μl) at a split ratio of 25:1. These conditions resolved (S)-PM and (R)-PM at 3.136 min and 3.192 min, respectively.

Liquid Chromatographic Methods. A Perkin-Elmer Series 200 Liquid Chromatograph equipped with quaternary LC pump, diode array detector (DAD), Peltier column oven, and Series 200 autosampler was used for analyses of samples containing DOWANOL® PPh (1-phenoxy-2-propanol; PPh) and its acetate (PPhA). Compounds were separated on a Chiralcel OD-RH column (4.6×150 mm; Chiral Technologies, Inc., Exton, Pa.) using an isocratic 10/40/50 ethanol/acetonitrile/water mobile phase at a flow rate of 0.65 min with the column temperature maintained at 35° C. Under these conditions, retention times for (R)-PPh, (S)-PPh, (R)-PPhA and (S)-PPhA were approximately 6.0 min, 7.3 min, 12.6 min and 13.1 min, respectively. This method was useful for PPh ee determination since it provided base line resolution of PPh enantiomers which were not completely resolved by the GC-method. In addition, PPh and PPhA were sufficiently separated from minor impurities presumed to be di(propylene glycol)phenyl ether (DPPh; present at up to 7% in commercial preparations of PPh) and its acetate, DPPhA.

Example 2

Asymmetric Synthesis of (S)-PM and (S)-PMA (S)-1-Methoxy-2-propanol [(S)-PM]

A 3-neck 100 ml round bottom flask was equipped with cooling water condenser, a thermowell, heating mantle/temperature controller, a magnetic stir bar, and a rubber septum. The flask was then transferred to the heating mantle resting on a stir plate and a nitrogen pad was placed on the reaction setup through the top of the condenser and maintained throughout the reaction. To the flask was loaded methanol (22.99 grams) and potassium hydroxide (0.0322 g) was then added with stirring and the set point adjusted to 45° C. When the solution reached the desired temperature, pre-chilled (S)-propylene oxide [(S)-PO; Chirex Batch T67893, Chirex order No. 607] was added to the reaction flask through the rubber septum using a sylinge in approximately 5 ml increments. A total of 12.19 g of PO was delivered to the reaction flask. GC analysis (see analytical methods below) showed minimal conversion of the methanol and PO to the desired propylene glycol methyl ether (PM glycol ether). An additional 0.0294 g of KOH was added and the reactor was heated at 50° C. for approximately 15 hours. Sampling and GC analysis showed only 0.007% unreacted (S)-PO. The PM glycol ether was flashed away from the catalyst and higher boiling byproducts by increasing the internal temperature to 150° C. The PM glycol ether fraction started to boil at an overhead temperature of 91° C. to 118° C. and approximately 15 ml of liquid was collected. GC analysis of the flashed material showed 95.4% 1-methoxy-2-propanol (PM-2) and 3.2% 2-methoxy-1-propanol (PM-1).

Since the base catalyzed hydrolysis of (S)-PO proceeds with complete inversion at the carbon undergoing nucleophilic substitution (Ege, 1989), the ring-opening reaction yielding PM-2 occurs with retention of configuration at the chiral center and the resulting secondary alcohol is of (S)-configuration. In contrast the minor PM-1 product is formed via substitution at the C2 carbon and the resulting primary alcohol is of (R)-configuration.

(S)-1-Methoxy-2-propanol acetate [(S)-PMA]

To a 25-ml flask was added 4.0 g (0.044 mole) of the (S)-PM-2/(R)-PM-1 mixture with 0.02 g anhydrous zinc chloride. A reflux condenser with drying tube was attached and 4.7 g (0.046 mole) acetic anhydride was added by lifting the drying tube momentarily. The mixture was refluxed at about 118° C. for 2 hours and then allowed to cool. GC-analysis of a 1% solution in water showed a single peak for PMA-2 with retention time matching the first peak observed for commercial PMA-2 enantiomers. These results indicated that the first PMA-2 peak is the (S) enantiomer. A single peak was also observed for the PMA-1 enantiomer. This peak also matched the first peak for PMA-1, present in ~3% in the commercial mixture, indicating that it was (R)-2-methoxy-1-propanol acetate. These results indicate that the (R) and (S) PMA-1 enantiomers exhibit opposite elution order from that observed for the corresponding PMA-2 enantiomers. The mixture was neutralized by adding 2.44 g (0.024 mole) anhydrous sodium carbonate and stirring for approximately 1 hour with $CO_2$ evolution. A short path distillation head was attached and the reaction product was distilled using a heat gun as heat source. About 5.0 g material boiling in the 95-137° C. range was collected. GC analysis showed sample purity to be about 95% (S-PMA-2 92.6% and R-PMA-1 2.7%).

Example 3

Hydrolysis of PMA: Enzyme Screening

A panel of over 110 commercial hydrolases were screened for enantioselective hydrolysis of PMA.

Methods

An initial screening of commercial enzymes for enantioselective hydrolysis of PMA was conducted in 0.2 ml reactions containing 0.5% (v/v) substrate (added from 10% aqueous stock) and 1.0 mg/ml enzyme in 0.065 M $KNaPO_4$ (pH 7.2) Sorensen's phosphate buffer. The reactions were initiated by addition of substrate and were incubated at 30° C. (unless otherwise indicated) in 1.8 ml Teflon-lined screw cap autosampler vials with horizontal shaking at 300 rpm. Control reactions lacking enzyme were used to assess abiotic conversion. Reactions were terminated by addition of 0.8 ml acetonitrile. The resulting solutions were refrigerated for at least 1 hour and then analyzed by GC-FID (see below).

Results

For the initial substrate analyzed, PMA, results based on a screen of over 110 commercial hydrolases indicated that *Candida antarctica* lipase type B (CAL-B) catalyzed enantioselective hydrolysis of the (R)-enantiomer of PMA [(R)-1-methoxy-2-propanol acetate; (R)-PMA], resulting in the resolution of (S)-PMA in greater than 99% ee (as shown in Table 1; this table lists those enzymes which catalyzed an enantioselective hydrolysis of PMA). The highly enantioselective performance of CAL-B was observed in enzyme preparations supplied as Chirazyme L-2, lyo., (Roche), Altus 13 (Altus Biologics, Inc), Lipase SP-435 (Novo Nordisk), and recombinant CAL-B (Fluka BioChemika). The additional studies described with CAL-B in this example were conducted with Chirazyme L-2, lyo. (Roche).

Other enzymes exhibiting similar enantioselectivity but generally resulting in lower enantiopurity (greater than 80% ee) in the screening assays include *Pseudomonas* sp. lipase (Chirazyme L-6, lyo; Roche), *Pseudomonas* sp. lipoprotein lipase (Fluka Biochemika), lipase PS-C1 (Amano), and *Pseudomonas cepacia* lipase (Altus Biologics, Inc) (Table 1). Enzymes exhibiting opposite enantioselectivity to CAL-B include esterases E001, E002 and E003 (Thermogen, Inc.).

TABLE 1

Summary of screening results[1] for commercial hydrolases catalyzing enantioselective hydrolysis of PMA (0.5%, v/v).

| No. | Enzyme | Source (supplier) | (S)-PMA (% v/v) | (R)-PMA (% v/v) | PMA (% ee) |
|---|---|---|---|---|---|
| 1 | Chirazyme L-2, lyo | *Candida antarctica* lipase B (Roche Molecular Biochem.) | 0.0642 | 0.0001 | 99.7% S |
| 33 | Lipase SP-435 | *Candida antarctica* lipase B (Novo Nordisk) | 0.0593 | 0.0001 | 99.7% S |
| 49 | Altus 13 | *Candida antarctica* lipase B (Altus Biologics, Inc) | 0.0775 | 0.0001 | 99.7% S |
| 106 | Lipase B, recombinant | *Candida antarctica* lipase B (Fluka Biochemika) | 0.0732 | 0.0001 | 99.7% S |
| 91 | Lipase LP 'S' | (Amano) | 0.0666 | 0.0001 | 99.7% S |
| 115 | Lipoprotein lipase | *Pseudomonas* sp. lipoprotein lipase (Fluka Biochemika) | 0.0567 | 0.0001 | 99.6% S |
| 5 | Chirazyme L-6 | *Pseudomonas* sp. lipase (Roche Molecular Biochem.) | 0.0594 | 0.0050 | 84.5% S |
| 95 | Lipase PS-C I | *Pseudomonas cepacia* lipase (Amano) | 0.0894 | 0.0157 | 70.1% S |
| 38 | Altus 2 | *Pseudomonas cepacia* lipase (Altus Biologics, Inc) | 0.0707 | 0.0186 | 58.3% S |
| 66 | E001 | Esterase (Thermogen, Inc.) | 0.0043 | 0.0431 | 81.9% R |
| 67 | E002 | Esterase (Thermogen, Inc.) | 0.0001 | 0.0208 | 99.0% R |
| 68 | E003 | Esterase (Thermogen, Inc.) | 0.0082 | 0.0476 | 70.6% R |

[1]Results were determined by GC/FID analysis and reported as % volume/volume (% v/v) for 1:5 dilutions of screening assays containing 0.5% PMA and approximately 1.0 mg/ml enzyme incubated as described in the text for 20 hours.

Example 4

Hydrolysis: Optimization

Experiments were undertaken to determine conditions under which various reaction parameters, including yield or conversion (quantitated as the proportion or amount of substrate hydrolyzed), isomeric purity (determined as % ee), substrate loading (or concentration), enzyme loading, and reaction time, temperature, and medium, could be optimized, for both laboratory scale and reactor scale (or scale up).

Methods

Rates of substrate hydrolysis and enantiomieric excess of resolved substrate were typically evaluated in 0.5 ml reaction mixtures set up in 1.8 ml Teflon-lined screw cap autosampler vials. Unless indicated otherwise, the reaction mixtures were incubated horizontally with rotary shaking (300 rpm), typically at 30° C., and with CAL-B (Chirazyme L-2, lyo., *Candida antarctica* lipase type B, greater than 120 U/mg lyo) as the biocatalyst. Reactions containing at least 10% (v/v) substrate were sampled and diluted 1:100 in acetonitrile prior to analysis. A series of studies were conducted to systematically evaluate the performance of CAL-B as an enzymatic catalyst for hydrolytic resolution of the P-series glycol ether acylates and to identify conditions for an efficient enzymatic resolution bioprocess. The following conditions were examined in independent screening experiments:

Biphasic reaction mixtures with different solvents (phase ratio 0.5)

Increased substrate concentration in different biphasic reaction mixtures

Increased product concentration at different substrate concentrations in aqueous reaction mixtures Increased buffer capacity in aqueous and biphasic reactions Maximal substrate concentrations for complete, enantioselective hydrolysis Different enzyme concentrations in biphasic reactions Endpoint conversion reactions with high enzyme and substrate concentrations Different incubation temperatures in aqueous reactions Results Biphasic Reactions with Toluene and Hexane.

Hydrolysis of substrate (PMA) by the enzymatic catalyst CAL-B (Chirazyme L-2) was examined under biphasic reaction conditions with higher substrate concentrations and different cosolvents. Toluene and hexane were added as cosolvents at a phase ratio of 0.5 (50% v/v) in reactions containing 10% (v/v) PMA. Similar reactions were set up to examine the performance of CAL-B (Chirazyme L-2) with PMA at 10% and 50% (v/v) as both the substrate and solvent. The reactions were incubated for 16 hours at 30° C., and the products analyzed by GC.

The results support the following conclusions. PMA at 50% (v/v) as both substrate and solvent was slightly inhibitory. Toluene at 50% (v/v) was suitable as a cosolvent, but the final yield of resolved (S)-PMA was lower (it is believed that the decreased yield is due to either lower enantioselectivity, or faster catalysis resulting in a longer period to hydrolyze remaining (S)-PMA). Hexane at 50% (v/v) was the best cosolvent based upon high observed yield of (S)-PMA at greater than 99% ee. PMA at 10% (v/v) in aqueous reactions was efficiently hydrolyzed and resulted in (S)-PMA resolution in high yield and greater than 99% ee.

Increased PMA Concentration in Hexane and Toluene Biphasic Reactions.

The effects of increasing substrate concentration was examined in biphasic reactions containing either hexane or toluene as co-solvents.

Increasing PMA loading from 10% to 25% (v/v) with 50% (v/v) hexane as a cosolvent resulted in the final enantiopurity of (S)-PMA decreasing from greater than 99% to greater than 87% ee. Reactions containing 50% PMA with 25% and 40% hexane resulted in final (S)-PMA purity of greater than 83% ee and greater than 66% ee, respectively.

The highest substrate concentration allowing complete enantioselectivity without product inhibition was determined by measuring hydrolysis of 10 to 50% (v/v) PMA in reactions with hexane and toluene as cosolvents (from 25 to 65%, v/v) and a constant aqueous phase concentration of 25% v/v. Endpoint analysis again confirmed hexane as a better cosolvent, and further indicated that 10% (v/v) PMA with hexane as cosolvent resulted in resolution of (S)-PMA in greater than 99% ee. Under the same conditions with 20% (v/v) PMA, the enantiopurity of (S)-PMA was reduced to 93% ee.

Effect of Increased PM Concentrations with 10% & 25% PMA in Aqueous Reactions

In order to determine if CAL-B (Chirazyme L-2) was subject to product inhibition by PM, hydrolysis of PMA was examined under aqueous conditions with increasing concentrations of PM.

The extent of hydrolysis was unaffected in reactions contaning 10% (v/v) PMA in the presence of up to 15% (v/v) added PM; resolution of (S)-PMA to greater than 99.5% ee in maximum theoretical yield was effected by 2 hours. However, slight inhibition was noted in reactions containing 20% (v/v) PM, with (S)-PMA enantiopurity dropping to ~96% ee. This threshold was furter analyzed by examining hydrolysis of 25% (v/v) PMA with increasing concentrations of added PM (0 to 50%). Under these conditions, complete enantioselective hydrolysis of substrate was expected to liberate about 12.5% PM, and the addition of end product did inhibit the extent of conversion and reduce final enantiopurity of (S)-PMA. Thus, these results indicate that the preferred substrate concentration is about 25% (v/v).

The final pH of these reactions ranged from 3.5 to 4.5. Thus, in addition to inhibition by the alcoholic end product, the potential of pH inhibition due to liberation of acetic acid was considered (see below).

It is contemplated that, based on the above results, selective methods for integrated product recovery and removal could allow the reaction to proceed at higher substrate concentration (see, for example, Indlekofer, M. et al. (1996) Biotechnology and Bioengineering, 52:459-471; and Indlekofer, M. et al. (1995) Biotechnology Progress 11:436-442).

Increased Buffer Concentration

The effect of increasing buffer concentration was examined in aqueous and biphasic (25% (v/v) hexane) reactions containing 50% (v/v) PMA and 1 mg/ml CAL-B (Chirazyme L-2 lyo.).

Reactions containing 0, 66 and 200 mM Sorensen's phosphate buffer (pH 7.2) showed no difference in the rate or extent of PMA hydrolysis over a period of 44 hours. The final product enantiopurity reached by 18 h for aqueous and biphasic reactions corresponded to (S)-PMA of greater than 93% ee and greater than 84% ee, respectively. These results suggested that the acetic acid liberated during the course of substrate hydrolysis did not inhibit the progress of the reaction. The final pHs of the reactions conducted in water, 66 mM buffer and 200 mM buffer were in the range of 3.0-3.5, 4.0-4.5 and 4.5, respectively.

Maximum PMA Concentrations Undergoing Complete Enantioselective Hydrolysis in Aqueous and Biphasic Reactions The extent of substrate hydrolysis and its final % ee was measured as a fimction of substrate concentration in order to determine the maximum concentration of PMA resulting in complete enantioselective hydrolysis under aqueous and biphasic conditions (n-hexane in a phase ratio of 0.2). The enzymatic catalyst was CAL-B (Chirazyme L-2 lyo.) at 1 mg/ml.

Complete resolution of (S)-PMA at greater than 99.5% ee was observed in aqueous reactions containing up to 25% (v/v) PMA by 64 hours. Similar reactions containing 30% (v/v) and 40% (v/v) PMA yielded greater than 97.5% ee and greater than 95.5% ee (S)-PMA, respectively. Under biphasic reaction conditions with 20% (v/v) hexane, lower product enantiopurity was observed; PMA loaded at 20% (v/v), 25% (v/v) and 40% (v/v) was resolved within 64 hours to (S)-PMA at greater than 98.5% ee, greater than 97% ee, and 92% ee, respectively.

Figure 2:
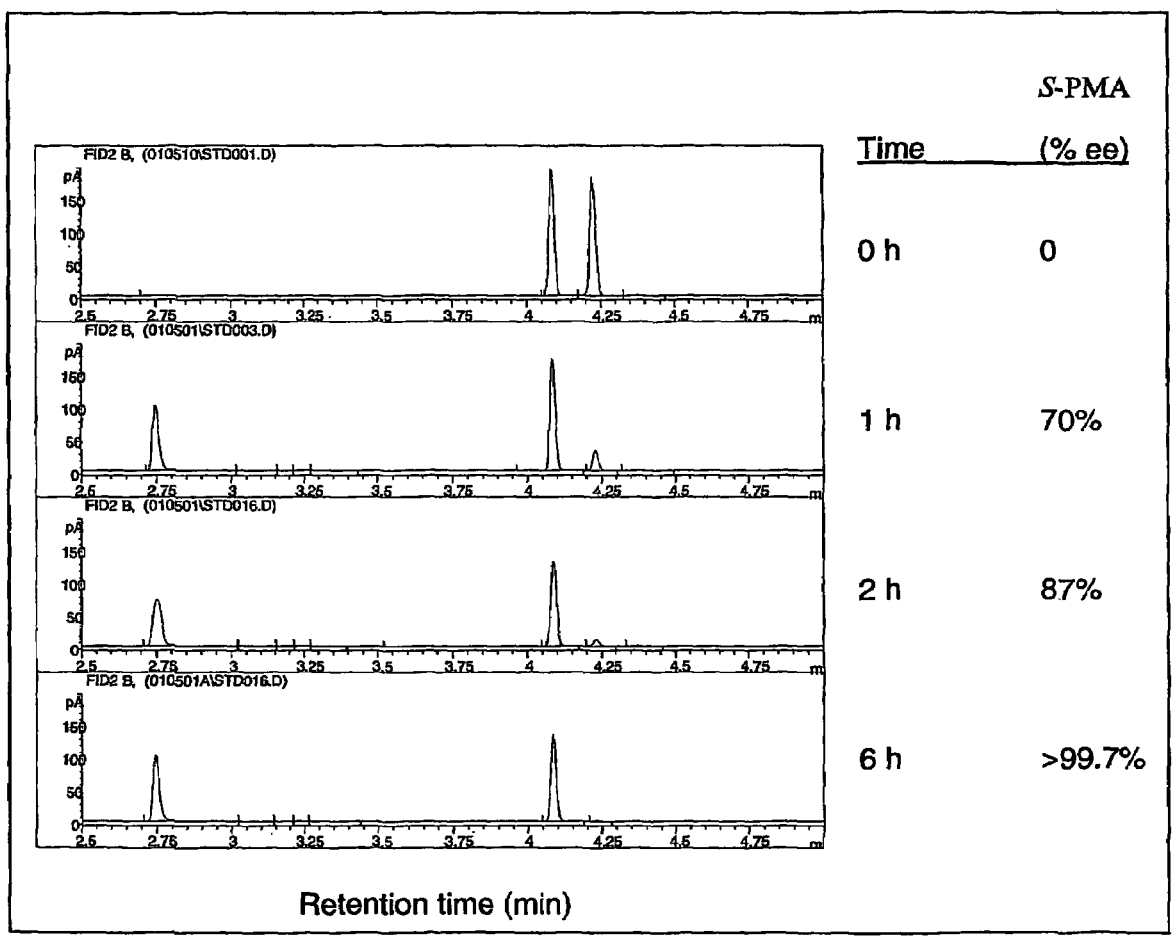
FIG. 2 shows the resolution of (S)-PMA from a reaction mixture analyzed by GC/FID. The reaction mixture contained CAL-B (1.0 mg/ml Chirazyme L-2 lyo.) and 25% (v/v) PMA in an aqueous medium (sodium-phosphate buffer, pH 7.2). Retention times are: racemate PM, 2.81 min; PMA-S, 4.10 min; PMA-R, 4.24 min.

These results indicated that PMA was most efficiently hydrolyzed under aqueous conditions, and that a maximum concentration of 25% (v/v) PMA undergoes complete enantioselective hydrolysis under the experimental conditions employed (as shown in FIG. 2).

Effect of Enzyme Concentration on Hydrolysis of PMA in Aqueous and 50% Hexane Biphasic Reactions Reactions containing CAL-B (Chirazyme L-2 lyo., greater than 120 U/mg) at concentrations of 1.0, 0.5, 0.1, 0.05, 0.01, 0.001 mg/ml were used to determine the minimum activity Units required to effect enantioselective hydrolysis of 10% (v/v) PMA under biphasic conditions with 50% (v/v) hexane.

After 2 hours, reactions containing enzyme loadings of 1.0 and 0.5 mg/ml had resolved the (S-enantiomer of PMA to greater than 98% ee in near theoretical yield. By 72 hours, reactions containing enzyme loadings of $\geq$0.01 mg/ml resolved (S)-PMA in greater than 99.5% ee. However, the extended incubation led to further hydrolysis which reduced the yield of (S)-PMA in reactions containing enzyme at 0.5 and 1.0 mg/ml to approximately 25% and 10%, respectively (based on maximum theoretical yield of 50%).

Figure 3:
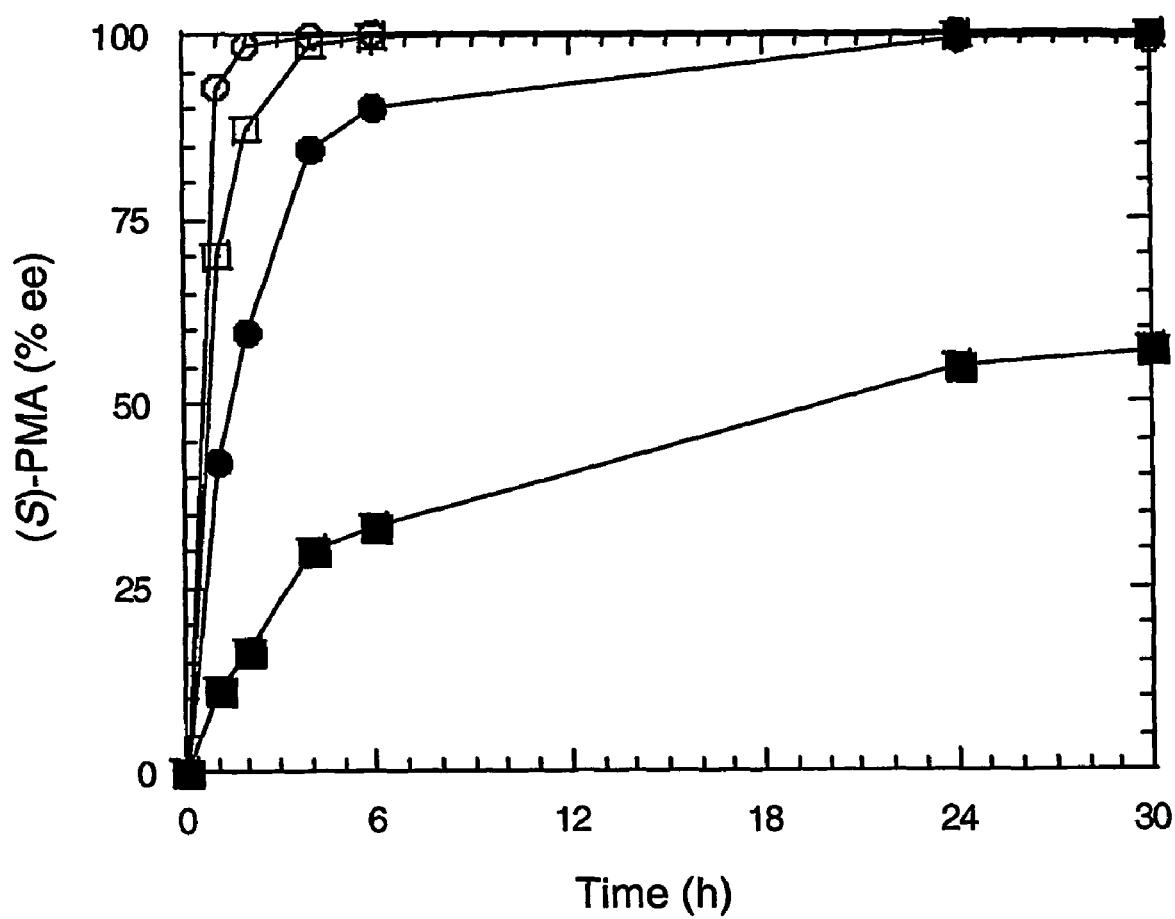
FIG. 3 shows the resolution of (S)-PMA as a function of CAL-B enzyme concentration. Aqueous reaction mixtures contained PMA at 25% (v/v) and Chirazyme L-2 lyo. at 0.1 mg/ml (solid squares), 0.5 mg/ml (solid circles), 1.0 mg/ml (open squares) and 2.0 mg/ml (open circles).

In similar experiments, hydrolysis was examined as a function of enzyme concentration in aqueous reactions containing 25% (v/v) PMA; the results are shown in FIG. 3. The results indicated that CAL-B (Chirazyme L-2 lyo.) at concentrations of 2.0, 1.0 and 0.5 mg/ml effected complete resolution of (S)-PMA to greater than 99% ee within 4, 6 and 24 hours, respectively (FIG. 3). In contrast, a reaction containing 0.1 mg/ml CAL-B (Chirazyme L-2 lyo.) partially resolved (S)-PMA (<60% ee) within 30 hours.

Effect of High Enzyme and PMA Concentrations on Enantioselectivity

Reactions containing CAL-B (Chirazyme L-2 lyo.) at 2.0 and 5.0 mg/ml and PMA concentrations ranging from 25% (v/v) to 50% (v/v) were used to assess enzyme selectivity and the extent of substrate conversion.

Aqueous reactions containing enzyme loadings of 2.0 and 5.0 mg/ml effected resolution of up to 40% (v/v) PMA loading within 6 hours, resulting in (S)-PMA of greater than 95% ee in maximum yield. No significant decrease in Yoee or yield of (S)-PMA was noted after incubation for 30 hours, indicating that the CAL-B preparation was extremely enantioselective for (R)-PMA hydrolysis under the conditions described.

Effect of Temperature on Hydrolysis of PMA in Aqueous Reactions

The effect of incubation temperature between 30° C. and 50° C. (5° C. increments) was examined in aqueous reactions containing PMA 25% (v/v) and 1.0 and 0.5 mg/ml CAL-B (Chirazyme L-2 lyo.) Under these conditions, PMA hydrolysis was most rapid at 40° C., and final enantiopurity was not effected at this temperature. However, reactions incubated at 35° C. with lower enzyme loading showed sustainable catalysis for a longer duration and resulted in higher (S)-PMA enantiopurity than did reactions incubated at 40° C. Incubation at 50° C. inactivated the enzyme within 5 hours.

Assuming that the measured rates of hydrolysis were independent of temperature-induced differences in substrate solubility, the results indicated that the temperature optimum for CALB (Chirazyme L-2 lyo.) is approximately 40° C., but that greater enzyme stability is observed at 35° C.

Example 5

Enantioselective Hydrolysis of Additional P-Series Glycol Ether Acetates

Hydrolysis: Enzyme Screening

The same panel of over 110 commercial hydrolases which were screened for enantioselective hydrolysis of PMA were also screened for enantioselective hydrolysis of additional P-series glycol ether acetates. These enzymes were initially screened as generally described in Example 2, where the substrate concentration was 0.5%, v/v. Two reactions were set up for each substrate and terminated at 4 h and 24 h. The 4 h sampling was conducted to identify selective enzymes catalyzing extremely rapid hydrolysis. Initially, the elution order of PMA enantiomers was used as the basis for the assignment of absolute configuration of the PEA, PnPA, PiPA, and PnBA enantiomers, separated under identical GC conditions, with the earliest eluting enantiomer empirically assigned to be of (S)-configuration; this elution was subsequently confirmed with chemically synthesized enantiomerically pure compounds of known stereochemistry (as described under Example 1).

Several enzymes catalyzing the enantioselective hydrolysis of each substrate were identified; these enzymes are referred to as "hits." The majority of the hits identified hydrolyzed the (R)-enantiomer of the glycol ether acetate substrate resulting in the resolution of the (S)-enantiomer of the acetate in greater than 85% ee. Enzymes exhibiting opposite enantioselectivity also exist and were identified in the initial enzyme screening; these enzymes include esterases E001, E002 and E003 (Thermogen, Inc). But their enantioselectivity observed in these initial screening reactions was not as high as their counterpart enzymes.

The most enantioselective enzymes were rescreened in aqueous 0.5 ml reactions containing ~2 mg/ml enzyme and glycol ether acetate substrates at 0.5%, 10%, 25% (v/v). These secondary screening reactions were used to examine the performance of enantioselective enzymes at higher substrate concentrations. The most enantioselective enzymes for hydrolysis of PEA, PnPA, PiPA and PnBA are listed in Tables 2-5. Among them, *Candida antarctica* lipase type B (CAL-B) was most selective for each of the glycol ether acetate substrates. The selective performance of CAL-B was observed in enzyme preparations supplied as Chirazyme L-2, lyo., (Roche), Altus 13 (Altus Biologics, Inc), Lipase SP-435 (Novo Nordisk), and recombinant CAL-B (Fluka BioChemika). The redundancy in the collection of enzymes screened was considered a benefit, since multiple hits identified the same enzyme from different commercial suppliers.

TABLE 2

Summary of screening results[1] for commercial hydrolases catalyzing enantioselective hydrolysis of PEA.

| Enzyme | Source (supplier) | R-PE % ee (% v/v) | S-PEA % ee (% v/v) | E Value[2] (% C) |
|---|---|---|---|---|
| Lipase B, recombinant | *Candida antarctica* lipase B (Fluka Biochemika) | 91.50% (7.16) | 98.74% (6.52) | 113 (53) |
| Chirazyme L-2, lyo | *Candida antarctica* lipase B (Roche Molecular Biochem.) | 85.19% (8.94) | 98.45% (7.99) | 60 (54) |
| Altus 13 | *Candida antarctica* lipase B (Altus Biologics, Inc) | 88.81% (6.66) | 98.44% (6.01) | 81 (54) |
| Lipase SP-435 | *Candida antarctica* lipase B (Novo Nordisk) | 95.93% (8.46) | 97.11% (6.95) | 205 (55) |
| Lipase | *Pseudomonas fluorescens* (Fluka Biochemika) | 49.92% (6.60) | 97.61% (4.20) | 12 (67) |
| Lipase PS-C II | *Pseudomonas cepacia* lipase (Amano) | 88.98% (8.01) | 91.35% (7.49) | 55 (52) |
| Altus 2 | *Pseudomonas cepacia* lipase (Altus Biologics, Inc) | 90.09% (8.90) | 88.52% (8.26) | 57 (52) |
| Lipase PS | *Pseudomonas cepacia* lipase (Amano) | 90.43% (6.84) | 87.64% (6.64) | 57 (50) |
| Lipoprotein lipase | *Pseudomonas* sp. lipoprotein lipase, type B (Fluka Biochemika) | 92.22% (5.31) | 74.12% (5.68) | 55 (46) |
| Chirazyme L-6 | *Pseudomonas* sp. lipase (Roche Molecular Biochem.) | 93.40% (5.03) | 57.12% (6.19) | 52 (40) |

[1]Results were determined by GC/FID analysis and reported as % (v/v) for 1:10 dilutions of screening assays containing PEA 10% (v/v) and approx. 2.0 mg/ml enzyme incubated as described in the text for 24 hours.
[2]$E = \ln((1 - ee\%PEA)/(1 + ee\%PEA/ee\%PE))/\ln((1 + ee\%PEA)/(1 + ee\%PEA/ee\%PE))$
Percent Conversion, % C estimated based on percentage volume: [(S) PE + (R) PE]/[(S) PEA + (R) PE A + [(S) PE + (R) PE] × 100

TABLE 3

Summary of screening results[1] for commercial hydrolases catalyzing enantioselective hydrolysis of PnPA.

| Enzyme | Source (supplier) | Time (h) | R-PnP % ee (% v/v) | S-PnPA % ee (% v/v) | E Value[2] (% C) |
|---|---|---|---|---|---|
| Chirazyme L-2, lyo | *Candida antarctica* lipase B (Roche Molecular Biochem.) | 4 | 99.07% (12.86) | 95.53% (6.13) | 827 (67) |
| Chirazyme, L-2, c.-f., C2, lyo | *Candida antarctica* lipase B Immobilized | 1 | 98.84% (6.88) | 92.86% (3.24) | 587 (67) |
| | | 4 | 96.33% (6.96) | 91.14% (2.59) | 171 (72) |
| Chirazyme L-6 | *Pseudomonas* sp. lipase (Roche Molecular Biochem.) | 4 | 92.79% (7.22) | 73.16% (4.58) | 59 (59) |
| Lipase LPS | Lipase (Amano) | 1 | 80.46% (7.39) | 94.45% (5.96) | 33 (57) |
| | | 4 | 50.12% (9.36) | 90.42% (2.98) | 9 (80) |

[1]Results were determined by GC/FID analysis and reported as % (v/v) for 1:100 dilutions of screening reactions containing PnPA 10% (v/v) and 2.0 mg/ml enzyme incubated at 30° C. with shaking (300 rpm) for the time specified. The enzyme concentration for 1a was 53.2 mg/ml.
[2]Enantioselectivity or "enantiomeric ratio" (E): $E = \ln((1 - ee\%PnPA)/(1 + ee\%PnPA/ee\%PnP))/\ln((1 + ee\%PnPA)/(1 + ee\%PnPA/ee\%PnP))$
Percent Conversion, % C estimated based on percentage volume: [(S) PnP + (R) PnP]/[(S) PnPA + (R) PnPA + (S) PnP + (R) PnP] × 100

TABLE 4

Summary of screening results[1] for commercial hydrolases catalyzing enantioselective hydrolysis of PiPA.

| Enzyme | Source (supplier) | Time (h) | R-PIP % ee (% v/v) | S-PIPA % ee (% v/v) | E Value[2] (% C) |
|---|---|---|---|---|---|
| Chirazyme L-2, lyo | Candida antarctica lipase B (Roche Molecular Biochem.) | 24 | 94.4% (3.10) | 94.14% (2.32) | 149 (54) |
| Chirazyme, L-2, c.-f., C2, lyo | Candida antarctica lipase B Immobilized (Roche Molecular Biochem.) | 1 | 96.5% (3.39) | 98.76% (1.16) | 287 (60) |
| Chirazyme L-6 | Pseudomonas sp. lipase (Roche Molecular Biochem.) | 24 | 94.86% (3.03) | 84.42% (2.25) | 102 (56) |
| Chirazyme L-10 | Alcaligines sp. lipase (Roche Molecular Biochem) | 24 | 94.8% (2.99) | 79.0% (2.3) | 90 (54) |
| Altus 19 | Pseudomonas cepacia lipase (Altus Biologies) | 1 | 94.46% (3.16) | 95.5% (3.06) | 135 (51) |
| Lipase LP S | Lipase (Amano) | 1 | 95.47% (3.02) | 95.27% (2.89) | 164 (51) |
| Lipase PS | Lipase (Amano) | 24 | 95.64% (3.14) | 94.12% (2.31) | 160 (57) |

[1]Results were determined by GC/FID analysis and reported as % volume/volume for 1:100 dilutions of screening reactions containing PiPA 10% (v/v) and 2.0 mg/ml enzyme incubated at 30° C. with shaking (300 rpm) for the time specified. The enzyme concentration for 1a was 53.2 mg/ml.
[2]Enantioselectivity or "enantiomeric ratio" (E): $E = \ln((1 - ee\%PIPA)/(1 + ee\%PIPA/ee\%PnP))/\ln((1 + ee\%PIPA)/(1 + ee\%PIPA/ee\%PIP))$
Percent Conversion, % C estimated based on percentage volume: $[(S) PIP + (R) PIP]/[(S) PIPA + (R) PIPA + (S) PIP + (R) PIP] \times 100$

TABLE 5

Summary of screening results[1] for commercial hydrolases catalyzing enantioselective hydrolysis of PnBA.

| Enzyme | Source (supplier) | Time (h) | R-PnB % ee (% v/v) | S-PnBA % ee (% v/v) | E Value[2] (% C) |
|---|---|---|---|---|---|
| Chirazyme L-2, lyo | Candida antarctica lipase B (Roche Molecular Biochem.) | 4 | 99.95% (3.10) | 96.5% (2.81) | >500 (52) |
| Chirazyme, L-2, c.-f., C2, lyo | Candida antarctica lipase B Immobilized (Roche Molecular Biochem. | 4 | 99.95% (2.24) | 98.29% (1.16) | >500 (66) |
| Chirazyme L-6 | Pseudomonas sp. lipase (Roche Molecular Biochem.) | 4 | 87.01% (2.88) | 81.19% (2.89) | 36 (49) |
| Chirazyme L-8 | Thermomyces sp. lipase (Roche Molecular Biochem) | 24 | 99.95% (1.8) | 75% (1.05) | >500 (60) |
| Altus 2 | Pseudomonas cepacia lipase (Altus Biologies) | 24 | 91.26% (1.97) | 63.64% (1.17) | 42.1 (59) |

[1]Results were determined by GC/FID analysis and reported as % volume/volume for 1:100 dilutions of screening reactions containing PnBA 10% (v/v) and 2.0 mg/ml enzyme incubated at 30° C. with shaking (300 rpm) for the time specified. The enzyme concentration for 1a was 53.2 mg/ml.
[2]Enantioselectivity or "enantiomeric ratio" (E): $E = \ln((1 - ee\%PnBA)/(1 + ee\%PnBA/ee\%PnP))/\ln((1 + ee\%PnBA)/(1 + ee\%PnBA/ee\%PnB))$
Percent Conversion, % C estimated based on percentage volume: $[(S) PnB + (R) PnB]/[(S) PnBA + (R) PnBA + (S) PnB + (R) PnB] \times 100$ Calculated E values of greater than 500 are reported as >500.

Based on the selective resolution of PEA, PnPA, PiPA and PnBA by CAL-B (as shown in Tables 2-5 above), Chirazyme L-2, lyo and Chirazyme L-2, c.-f., C2, lyo. were used separately to examine enantioselective hydrolysis of PPhA at high substrate concentrations. Aqueous 0.2 ml reactions containing 1.0 mg/ml Chirazyme L-2, lyo. or 26.6 mg/ml Chirazyme L-2, c.-f., C2, lyo and PPhA at 10, 15, 25, 35 and 50% (v/v) were used to assess enzyme selectivity and the extent of PPhA conversion. Analysis of aqueous reactions containing Chirazyme L-2, c.-f., C2, lyo. indicated that both (S)-PPhA and (R)-PPh were resolved in 99% ee (50% yield) at substrate loadings up to 25%. Partial resolution of (S)-PPhA was observed at substrate loadings of 35% (81% ee) and 50% (74% ee). Reactions containing Chirazyme L-2, lyo. effected the complete resolution of (S)-PPhA at a loading of 10% (greater than 99% ee); with substrate loaded at 15%, 25%, 35% and 50% (v/v), (S)-PPhA was resolved to approximately 95% ee, 86% ee, 79% ee and 69% ee.

Enantioselectivity of CAL-B

The enantioselectivity of CAL-B (Chirazyme L-2 lyo.) for different P-series glycol ether acetates was examined in aqueous reactions under various conditions. Several experimental conditions and results are summarized in Table 6 below.

TABLE 6

Hydrolysis of glycol ether acetates using immobilized CALB (Chirazyme L2, c.-f., C2, lyo)

| Substrate | Conc. (v/v %) | Temp. ° C. | Lipase[1] (mg/ml) | Reaction Time(h) | Conv. (%) | (R)- Ether % ee | (S)- Acetate % ee |
|---|---|---|---|---|---|---|---|
| PMA | 20 | 40 | 26.6 | 4 | 37.6 | n.d | >99 |
|  | 20 | 40 | 26.6 | 20 | 48.9 | n.d | >99 |
|  | 25 | 40 | 26.6 | 2 | 35.6 | n.d | >99 |
|  | 25 | 40 | 26.6 | 30 | 54.9 | n.d | 97.0 |
|  | 35 | 40 | 26.6 | 22 | 38.7 | n.d | 95.1 |
|  | 45 | 40 | 26.6 | 22 | 34.2 | n.d | 94.0 |
|  | 50 | 40 | 26.6 | 30 | 33.4 | n.d | 92.2 |
|  | 75 | 40 | 26.6 | 6.5 | 29.3 | n.d | 79.1 |
| PEA | 10 | 40 | 26.6 | 1.5 | 53.2 | 97.3 | 98.7 |
|  | 20 | 40 | 26.6 | 3 | 55.2 | 96.4 | 97.1 |
|  | 25 | 40 | 26.6 | 1.5 | 56.2 | 97.3 | 95.3 |
|  | 30 | 40 | 26.6 | 3 | 51.7 | 96.8 | 94.6 |
|  | 35 | 40 | 26.6 | 5 | 54.4 | 96.9 | 93.3 |
|  | 40 | 40 | 26.6 | 5 | 51.1 | 97.3 | 91.7 |
|  | 50 | 40 | 26.6 | 20 | 43.2 | 97.1 | 88.2 |
| PnPA | 15 | 30 | 26.6 | 4 | 73.2 | >99 | 91.4 |
|  | 25 | 30 | 26.6 | 4 | 59.6 | >99 | 89.7 |
|  | 35 | 30 | 26.6 | 4 | 63.2 | >99 | 86.0 |
|  | 50 | 30 | 26.6 | 24 | 55.6 | >99 | 80.3 |
| PiPA | 15 | 30 | 26.6 | 24 | 66.2 | 95.4 | 90.2 |
|  | 25 | 30 | 26.6 | 24 | 68.1 | 96.4 | 89.2 |
|  | 35 | 30 | 26.6 | 24 | 55.6 | 97.3 | 85.6 |
|  | 50 | 30 | 26.6 | 24 | 42.1 | 97.4 | 79.7 |
| PnBA | 15 | 30 | 26.6 | 4 | 81.7 | 97.9 | 93.6 |
|  | 25 | 30 | 26.6 | 4 | 50.4 | 98.9 | 87.5 |
|  | 35 | 30 | 26.6 | 4 | 48.5 | >99 | 83.5 |
|  | 50 | 30 | 26.6 | 4 | 47.8 | >99 | 76.9 |
| PPhA | 10 | 30 | 26.6 | 4 | 50.0 | >99 | >99 |
|  | 15 | 30 | 26.6 | 4 | 68.6 | >99 | >99 |
|  | 25 | 30 | 26.6 | 4 | 50.6 | >99 | >99 |
|  | 35 | 30 | 26.6 | 24 | 44.8 | >99 | 81.5 |
|  | 50 | 30 | 26.6 | 24 | 41.3 | >99 | 73.7 |

[1]Candida antarctica lipase type B, carrier fixed, available commercially as Chirazyme L-2, c.-f., C2, lyo (~10 U/mg, Roche Molecular Biochemicals).
n.d Not determined.

The results show that CAL-B catalyzes enantioselective hydrolysis of PEA, PnPA, PiPA, PnBA, and PPhA, resulting in high purity of both the (S)-acetate and the (R)-ether. The results also indicate that CAL-B exhibits broad substrate specificity while in most cases retaining high enantioselectivity at all substrate loadings under the conditions examined.

The enantioselective resolution performance of CAL-B at various concentrations of each glycol ether acetate substrate up to high substrate concentrations (50% to 70% v/v) and at various enzyme concentrations is summarized in Table 7. Also shown in Table 7 is a summary of some optimal parameters for enantioselective hydrolysis of glycol ether acetates.

shown in Table 8). Additional experiments indicated that the highest enantioselectivity initially appeared to occur under anhydrous conditions with ethyl acetate at 90% (v/v). However, high initial enantioselectivity with vinyl acetate could not be ruled out, on the hypothesis that a more rapid esterification of the preferred alcohol enantiomer was likely followed by slower acylation of the less favored alcohol enantiomer. This hypothesis was confirmed by temporal analyses of reactions, which showed that 5.0 mg/ml CAL-B (Chirazyme L-2 lyo.) catalyzed enantioselective acylation of

TABLE 7

Summary of screening results for commercial hydrolases catalyzing enantioselective hydrolysis of PMA, PEA, PnPA, PiPA, PnBA and PPhA.

| Substrate | Numbers of Enzyme Screened, Secondary (Primary) | Range of Substrate Conc. With CAL-B (% v/v) | Range of Enzyme Conc. with CAL-B | Optimal Conditions With CAL-B | | |
|---|---|---|---|---|---|---|
| | | | | Substrate conc. (% v/v) | Enzyme Loading | No. Recycle Demonstrated |
| PMA | 4 (>110) | 0.5-70 | 120-180 U/ml | 25 | 120 U/ml | 30 |
| PEA | 12 (>110) | 0.5-50 | 15-120 U/ml | 20 | 120 U/ml | 16 |
| PnPA | 8 (>110) | 0.5-50 | 120-240 U/ml | 10 | 240 U/ml | n.d. |
| PiPA | 7 (>110) | 0.5-50 | 120-240 U/ml | 10 | 240 U/ml | n.d. |
| PnBA | 8 (>110) | 0.5-50 | 120-240 U/ml | 10 | 240 U/ml | n.d. |
| PPhA | 2 | 0.5-50 | 120 U/ml | 15 | 120 U/ml | 5 | n.d. Not determined

Example 6

Transesterification: Initial Evaluation

Transesterification of PM by CAL-B.

The ability of CAL-B to catalyze transesterification of glycol alkyl (or aryl) ethers was initially examined in several different reactions. These reactions of 0.5 ml contained 5.0 mg/ml CAL-B (Chirazyme L-2 lyo.) and 10% (v/v) PM, with either vinyl acetate or ethyl acetate as acyl donors, and either with or without toluene or hexane as a nonpolar cosolvent. The results are shown in Table 8.

TABLE 8

Acylation of PM by CAL-B under different solvent and acyl donor conditions[1].

| Solvent/Acyl donor | Initial PM (% v/v) | PM (% v/v) | (S)-PMA (% v/v) | (R)-PMA (% v/v) | (R)-PMA (% ee) |
|---|---|---|---|---|---|
| Vinyl Acetate | 10% | 1.15 | 9.40 | 12.48 | 14% |
| Toluene/Vinyl Acetate (8:1) | 10% | 0.08 | 11.06 | 12.20 | 5% |
| Hexane/Vinyl Acetate (8:1) | 10% | 0.09 | 8.92 | 9.98 | 6% |
| Toluene/Ethyl Acetate (8:1) | 10% | 6.85 | 0.62 | 3.70 | 71% |
| Ethyl Acetate | 10% | 5.80 | 0.86 | 9.19 | 83% |

[1]Results are based on GC/FID analysis of reactions after 16 hour incubation under conditions described in the text Endpoint analysis conducted at 16 hours demonstrated that CALB catalyzed enantioselective acylation of PM with either vinyl acetate or ethyl acetate as an acyl donor (as up to 50% (v/v) PM with either vinyl acetate or ethyl acetate as acyl donor. In reactions containing 50% (v/v) each of PM and ethyl acetate, the resulting (R)-PMA was formed in greater than 98% ee within 1 hour.

The observation that ethyl acetate, a non-activated ester, can serve as acyl donor for this reaction indicates that optically active P-series glycol ethers can be produced in high yields.

Transesterification of Additional P-Series Glycol Ethers by CAL-B

Transesterification-based resolution of the P-series glycol ethers PM, PE, PnP, PiP, PnB and PPh was examined with the enzymatic catalyst CAL-B, with acyl donors ethyl acetate and vinyl acetate, and with a reaction medium of organic solvent. (R)-Enantiomers of the corresponding glycol ether acetates were formed as products in high optical purity.

Conversion of all glycol ethers examined was initially observed to be most rapid with vinyl acetate as the acyl donor.

Example 7

Transesterification: Optimization

Experiments were undertaken to determine conditions under which various reaction parameters, including yield or conversion (quantitated as the proportion or amount of substrate acylated), isomeric purity (determined as % ee), substrate loading (or concentration), enzyme loading, and reaction time, temperature, and medium, could be optimized, for both laboratory scale and reactor scale (or scale up).

Effect of Enzyme Concentration and Temperature

Adjusting enzyme loading was shown to be an effective method of increasing product optical purity through reaction engineering.

Figure 4A:
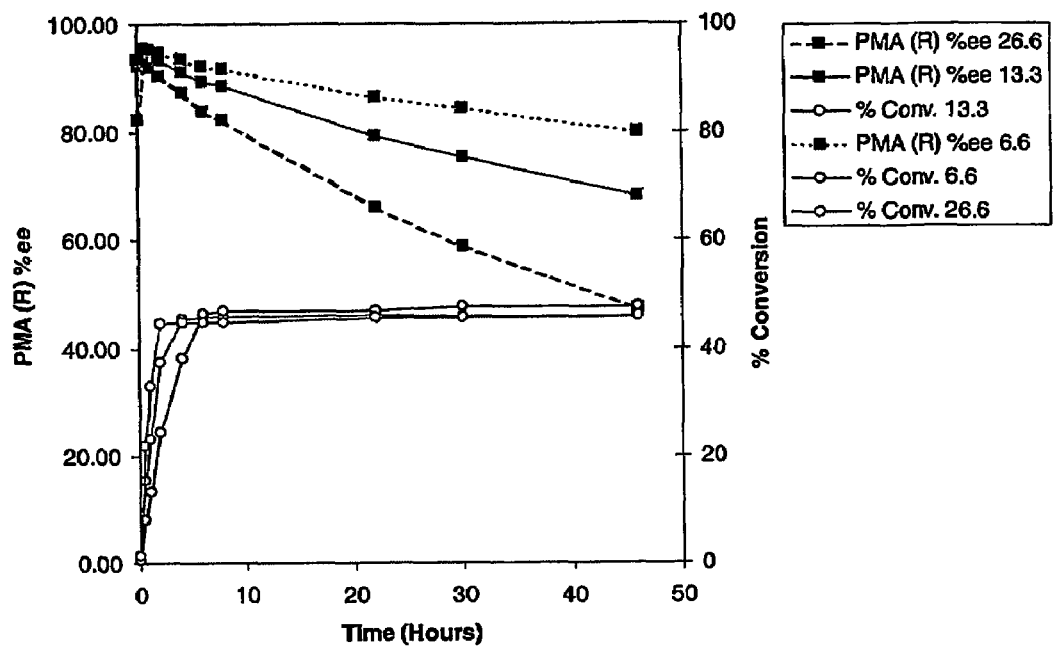
FIG. 4 shows the transesterification of (a) (±)-1-methoxy-2-propanol (PM) and (b) (±)-1-phenoxy-2-propanol (PPh) measured as a function of Chirazyme L-2, c.-f., C2 loading. Enantiomeric excess (% ee) of (R)-PM and (R)-PPhA and % conversion were determined in reaction mixtures containing ratios of PM/VA (75:25,% v/v) and PPh/VA (80:20,% v/v) which limit the theoretical conversions to 35% and 45%, respectively. The numbers in the symbol legends provide the concentration in mg/ml of Chirazyme L-2, c.-f., C2 in reactions.
Figure 4B:
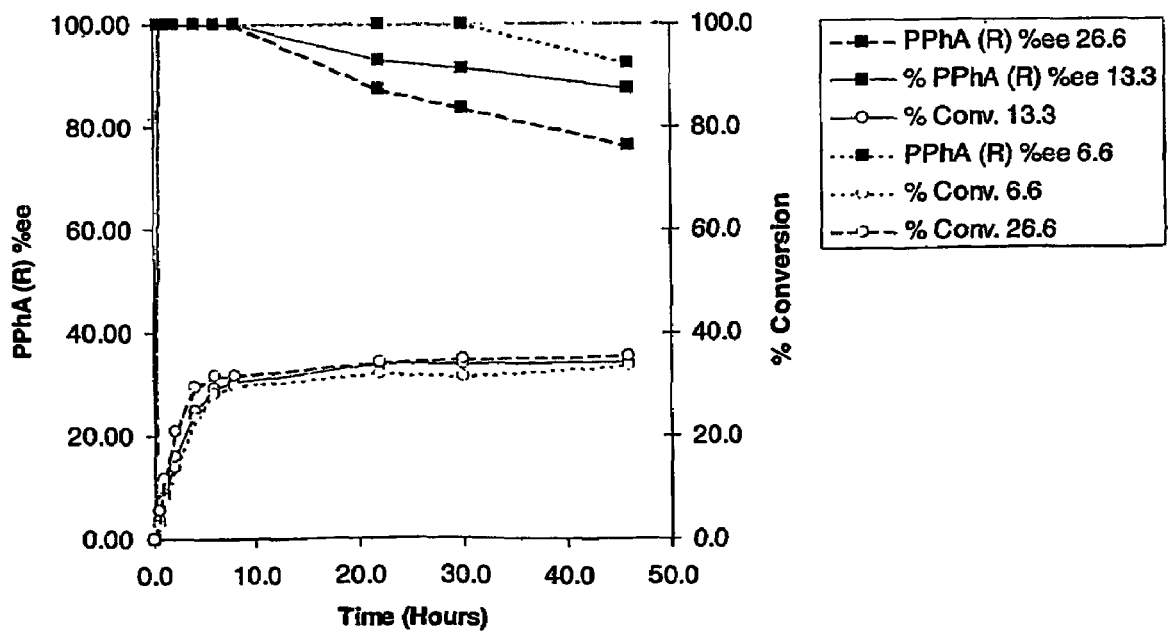

Enantioselective transesterification of PM and PPh, included in 1.0 ml reactions at substrate/acyl donor ratios of 75/25% (v/v) PM/VA and 80/20% (v/v) PPh/VA was examined with carrier-fixed *Candida antarctica* lipase type B (Chirazyme L-2, c.-f., C2, lyo.) at 26.6, 13.3, and 6.7 mg/ml. The results showed the highest % ee for the (R)-enantiomer acetate products of PMA and PPhA correlating to reactions containing decreasing concentrations of enzyme; this correlation was independent of the degree of conversion. The overall conversion for PM was ~10% higher than the calculated theoretical conversion (based on amount of acyl donor) for the three enzyme loadings, while the conversion of PPh was ~10% less than the calculated theoretical conversion. Results of selective acylation to (R)-PMA and (R)-PPhA products are shown in FIG. 4. The results indicate that conditions leading to the highest % ee of (R)-PM and (R)-PPhA products are independent of % conversion and correlate to reactions containing the lowest enzyme loading examined (6.6 mg/ml).

The results of additional experiments in which transesterification of PM with vinyl acetate was examined at different enzyme loadings are shown in Table 9 below.

Reducing the reaction temperature results in increased enantioselectivity of CAL-B for transesterification-based resolution of PM. The rates of resolution were slower, but lowering reaction temperature was an effective way to increase product optical purity. This effect was demonstrated at temperatures ranging from −20° C. to 30° C.

Enantioselective transesterification of PM, included in 1.0 ml reactions at PM/vinyl acetate ratio of 75/25% or 70/30% v/v, was examined with carrier-fixed *Candida antarctica* lipase type B (Chirazyme L-2, c.-f., C2, lyo.) at 26.6, 13.3, 6.7, 3.3, and 1.7 mg/ml incubated at 30, 20, 4, and −20° C. (±2° C.) without shaking. The reactions containing lowest enzyme loading and incubated at the lowest temperature (−20° C.) produced (R)-PMA of highest % ee, but at the slowest rate. However, the results indicate that suitable conditions for desired resolution performance can be identified through the optimizing incubation temperature and enzyme loading. The performance of reactions containing different enzyme loadings incubated at the various temperatures is shown in Table 9.

TABLE 9

Transesterification of (±)-1-methoxy-2-propanol (PM) with vinyl acetate as a function of enzyme concentration and temperature.

| Substrate | Acyl Donor | Sub./Acyl Donor Ratio | Temp. (° C.) | Enzyme Loading (mg/ml)[1] | Time (h) | Conv. (%) | (S)-glycol ether % ee | (R)-Acetate % ee |
|---|---|---|---|---|---|---|---|---|
| PM | VA | 75/25 | 30 | 26.8 | 2 | 44.6 | n.d. | 90.34 |
|  |  |  |  | 26.8 | 8 | 44.8 |  | 82.32 |
| PM | VA | 70/30 | 4 | 26.8 | 4 | 20.7 |  | 95.3 |
|  |  |  |  | 26.8 | 24 | 53.6 |  | 87.6 |
| PM | VA | 70/30 | −20 | 26.8 | 4 | 8.3 |  | 97.6 |
|  |  |  |  | 26.8 | 52 | 45.5 |  | 96.3 |
| PM | VA | 75/25 | 30 | 13.4 | 2 | 37.3 |  | 93.2 |
|  |  |  |  | 13.4 | 8 | 45.9 |  | 88.7 |
| PM | VA | 70/30 | 4 | 13.4 | 4 | 15.3 |  | 96.5 |
|  |  |  |  | 13.4 | 26 | 51.9 |  | 91.7 |
| PM | VA | 70/30 | −20 | 13.4 | 4 | 5.7 |  | 98.0 |
|  |  |  |  | 13.4 | 52 | 35.5 |  | 97.7 |
| PM | VA | 75/25 | 30 | 6.8 | 2 | 24.3 |  | 94.7 |
|  |  |  |  | 6.8 | 8 | 46.9 |  | 91.7 |
| PM | VA |  | 20 | 6.8 | 6 | 24.5 |  | 92.1 |
|  |  |  |  | 6.8 | 22 | 42.4 |  | 87.7 |
| PM | VA |  | 4 | 6.8 | 6 | 20.0 |  | 96.6 |
|  |  |  |  | 6.8 | 48 | 46.0 |  | 93.0 |
| PM | VA |  | −20 | 6.8 | 6 | 5.5 |  | 98.4 |
|  |  |  |  | 6.8 | 48 | 26.3 |  | 97.9 |
| PM | VA | 75/25 | 30 | 3.4 | 2 | 12.1 |  | 94.4 |
|  |  |  |  | 3.4 | 6 | 25.5 |  | 92.5 |
| PM | VA |  | 20 | 3.4 | 6 | 17.8 |  | 93.5 |
|  |  |  |  | 3.4 | 22 | 32.9 |  | 91.3 |
| PM | VA |  | 4 | 3.4 | 6 | 11.4 |  | 97.0 |
|  |  |  |  | 3.4 | 48 | 40.4 |  | 94.6 |
| PM | VA |  | −20 | 3.4 | 6 | 2.6 |  | 98.5 |
|  |  |  |  | 3.4 | 48 | 14.6 |  | 98.3 |
| PM | VA | 75/25 | 30 | 1.7 | 2 | 6.7 |  | 94.8 |
|  |  |  |  | 1.7 | 6 | 23.1 |  | 92.6 |
| PM | VA |  | 20 | 1.7 | 6 | 11.0 |  | 94.6 |
|  |  |  |  | 1.7 | 22 | 30.2 |  | 92.8 |
| PM | VA |  | 4 | 1.7 | 6 | 6.3 |  | 97.3 |
|  |  |  |  | 1.7 | 48 | 30.1 |  | 96.3 |
| PM | VA |  | −20 | 1.7 | 6 | 1.6 |  | 98.3 |
|  |  |  |  | 1.7 | 48 | 9.8 |  | 98.4 |

[1]*Candida antarctica* lipase type B carrier fixed form, available commercially as Chirazyme L-2, c.-f., C2, lyo (~10 U/mg, Roche Molecular Biochemicals).

Effect of Water

The effect of water activity and phosphate buffer (at <3% vol.) on rates of acylation and enantioselectivity was demonstrated with PM and PPh. Water content (water activity) slowed the reaction rate; however, it is contemplated that water content can be used to control reaction progress.

Effect of Substrate Concentration

CAL-B was shown to catalyze enantioselective resolution of glycol ethers PM, PE, PnP, PiP, PnB and PPh at substrate concentrations up to 70% (v/v) and with enantioselectivity (E) values of 50 to greater than 150, as shown in Table 10.

TABLE 10

Enzymatic resolution of (R)-acylates at high substrate concentrations[1]

| Substrate | Time (hrs) | (S)-OH % ee | (R)-OAc % ee | E value |
|---|---|---|---|---|
| PE | 6 hrs | 37% | 96% | 71 |
| PnP | 5 hrs | 95% | 89% | 65 |
| PiP | 6 hrs | 92% | 87% | 49 |
| PnB | 4 hrs | >99% | 82% | 59 |
| PPh | 4 hrs | >99% | 94% | 160 |

[1] The reaction volumes were 0.5 ml; the enzyme concentration was 1. mg/ml; the substrate concentration was 70% (v/v), and the acyl donor was vinyl acetate.

Figure 5:
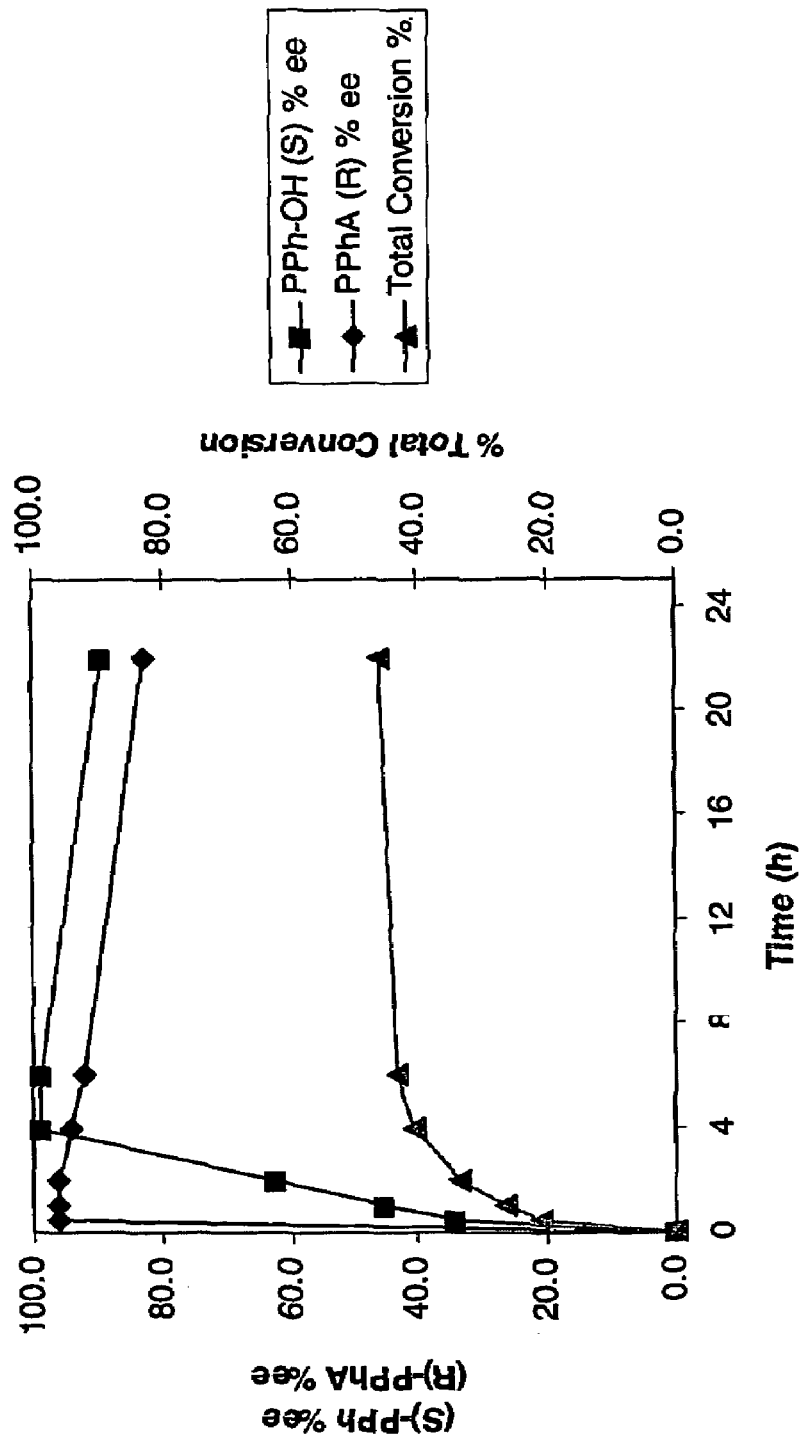
FIG. 5 shows the enantioselective acylation of PPh 70% (v/v) with vinyl acetate 30% (v/v)in reaction mixtures containing CAL-B (1 mg/ml).

The purity of the (R)-esters depends upon the duration of the reaction, or the stage at which the products are analyzed; it also depends upon whether substrate conversion is greater than or less than 50% (results for transesterification of PPh with vinyl acetate catalyzed by CAL-B are shown in FIG. 5). Typically, at less than 50% substrate conversion, the (R)-esters are present at high ee values. Thus, for the (R)-acetates, PEA was greater than about 96% ee, PPhA was greater than about 95% ee, and the remaining (R)-acetates for the P-series glycol ethers were greater than about 80% ee (for example, ee values of about 87%, 89%, and 82% were observed for PnBA).

Acyl Donors

The performance of different potential acyl donors was examined in 1.0 ml reactions containing Chirazyme L-2, c.-f, C2, lyo at 6.6 mg/ml, PE as the substrate or acyl-acceptor, and an amount of acyl donor corresponding to 1.0 molar equivalent. The resulting substrate loading of PE ranged from 35% to 55% (v/v) with the remaining reaction volume being acyl donor. In similar reactions, PnP was provided as the substrate with acyl donor at molar ratios corresponding to 1:1 and 1:2. The resulting substrate loading of PnP ranged from 31% to 59% (v/v) with the remaining reaction volume being acyl donor. Acyl donors examined included butyl acetate (BA), ethyl phenyl acetate (EPA), ethyl acetate (EtA), ethyl trichloroacetate (EtCA), ethyl trifluoroacetate (EtFA), isopropenyl acetate (IPA), vinyl acetate (VA), ethyl methoxy acetate (EMA), 2,2,2-trifluoroethyl butyrate (TfEB), diketene (DK) and vinyl propionate (VP). Reactions were incubated at 30° C. and sampled over a period of 24 h. The % ee of the resolved (S)-substrates and (R)-esters formed, and % conversion are shown in Table 11.

TABLE 11

Transesterification of glycol ethers PE and PnP using different acyl donors

| Substrate | Acyl Donor[1] | Sub./Acyl Donor Ratio (v/v) | Temp. °C. | Lipase[2] (mg/ml) | Time (h) | Conv. (%) | (S)-Glycol Ether ee (%) | (R)-Acetate ee (%) |
|---|---|---|---|---|---|---|---|---|
| PE | BA | 47/53 | 30 | 6.7 | 20 | 16.9 | 11.7 | 94.9 |
|  | BA | 47/53 | 30 | 6.7 | 24 | 17.8 | 9.5 | 94.7 |
|  | EPA | 39/61 | 30 | 6.7 | 20 | 2.1 | −1.5 | 51.0 |
|  | EtA | 54/46 | 30 | 6.7 | 20 | 17.5 | 9.8 | 94.3 |
|  | EtA | 54/46 | 30 | 6.7 | 24 | 18.4 | 3.1 | 96.7 |
|  | ETFA | 42/58 | 30 | 6.7 | 20 | 1.0 | −9.4 | 15.6 |
|  | IPA | 51/49 | 30 | 6.7 | 20 | 51.6 | 72.4 | 95.6 |
|  | IPA | 51/49 | 30 | 6.7 | 24 | 54.5 | 77.5 | 95.3 |
|  | VA | 55/45 | 30 | 6.7 | 20 | 44.7 | 51.8 | 95.2 |
|  | VA | 55/45 | 30 | 6.7 | 24 | 47.4 | 54.9 | 95.0 |
|  | EMA | 47/53 | 30 | 6.7 | 24 | 1.0 | 10.7 | 11.6 |
|  | TFEB | 38/62 | 30 | 6.7 | 20 | 60.6 | 54.5 | 63.9 |
|  | TFEB | 38/62 | 30 | 6.7 | 24 | 63.9 | 58.7 | 65.0 |
|  | VP | 51/49 | 30 | 6.7 | 20 | 62.5 | 73.2 | 67.3 |
|  | VP | 51/49 | 30 | 6.7 | 24 | 65.3 | 77.9 | 67.8 |
| PnP | BA | 50.5/49.5 | 30 | 6.7 | 2 | 7.4 | 5.2 | 98.4 |
|  | BA | 50.5/49.5 | 30 | 6.7 | 20 | 17.2 | 17.4 | 96.1 |
|  | BA | 34/66 | 30 | 6.7 | 6 | 17.1 | 16.4 | 97.6 |
|  | BA | 34/66 | 30 | 6.7 | 24 | 24.1 | 23.9 | 94.9 |
|  | EtA | 58/42 | 30 | 6.7 | 4 | 11.4 | 9.5 | 98.1 |
|  | EtA | 58/42 | 30 | 6.7 | 24 | 18.7 | 17.2 | 95.6 |
|  | EtA | 41/59 | 30 | 6.7 | 4 | 16.0 | 15.3 | 98.0 |
|  | EtA | 41/59 | 30 | 6.7 | 24 | 25.7 | 25.1 | 95.3 |
|  | IPA | 55/45 | 30 | 6.7 | 4 | 33.5 | 38.6 | 97.8 |
|  | IPA | 55/45 | 30 | 6.7 | 20 | 54.9 | 98.7 | 91.8 |
|  | IPA | 38/62 | 30 | 6.7 | 6 | 45.1 | 62.5 | 96.9 |
|  | IPA | 38/62 | 30 | 6.7 | 20 | 58.7 | 98.0 | 88.1 |
|  | VA | 59/41 | 30 | 6.7 | 1 | 32.0 | 35.1 | 97.4 |
|  | VA | 59/41 | 30 | 6.7 | 6 | 52.6 | 85.2 | 93.6 |
|  | VA | 59/41 | 30 | 6.7 | 20 | 60.7 | 98.3 | 74.3 |
|  | VA | 42/58 | 30 | 6.7 | 1 | 39.3 | 47.2 | 96.7 |
|  | VA | 42/58 | 30 | 6.7 | 6 | 56.5 | 95.5 | 90.1 |
|  | VA | 42/58 | 30 | 6.7 | 20 | 66.1 | 97.7 | 66.8 |
|  | TFEB | 47/53 | 30 | 6.7 | 20 | 61.9 | 77.2 | 81.0 |

TABLE 11-continued

Transesterification of glycol ethers PE and PnP using different acyl donors

| Substrate | Acyl Donor[1] | Sub./Acyl Donor Ratio (v/v) | Temp. °C. | Lipase[2] (mg/ml) | Time (h) | Conv. (%) | (S)-Glycol Ether ee (%) | (R)-Acetate ee (%) |
|---|---|---|---|---|---|---|---|---|
| | TFEB | 47/53 | 30 | 6.7 | 24 | 61.6 | 76.1 | 81.0 |
| | TFEB | 31/69 | 30 | 6.7 | 20 | 59.5 | 71.3 | 80.4 |
| | TFEB | 31/69 | 30 | 6.7 | 24 | 62.9 | 80.5 | 81.4 |
| | VP | 55/45 | 30 | 6.7 | 6 | 62.7 | 86.7 | 81.8 |
| | VP | 55/45 | 30 | 6.7 | 24 | 66.8 | 99.2 | 82.6 |
| | VP | 38/62 | 30 | 6.7 | 6 | 61.6 | 93.8 | 82.4 |
| | VP | 38/62 | 30 | 6.7 | 24 | 68.2 | 99.0 | 82.7 |

[1] Acyl donors examined: butyl acetate (BA), ethyl phenyl acetate (EPA), ethyl acetate (EtA), ethyl trifluoroacetate (ETFA), isopropenyl acetate (IPA), vinyl acetate (VA), ethyl methoxy acetate (EMA), 2,2,2-trifluoroethyl butyrate (TFEB), vinyl propionate (VP)
[2] *Candida antarctica* lipase type B, carrier fixed, available commercially as Chirazyme L-2, c.-f., C2, lyo (~10 U/mg, Roche Molecular Biochemicals)

No significant transesterification was detected with ethyltrichloro acetate or diketene as acyl donors. The results indicate that vinyl acetate and isopropenyl acetate are efficient acyl donors affording high selectivity for glycol ether acylation.

Additional considerations guide the selection of appropriate acyl donor; such considerations include the type of product formed during the reaction, and it's characteristics, including it's volatility and toxicity. For example, the use of vinyl acetate as an acyl donor results in the production of vinyl alcohol which is understood to tautomerize to acetaldehyde; acetaldehyde is very flammable (flash point −40° C.), it is a suspected animal carcinogen, and it is difficult to efficiently recover by distillation. Thus, the product represents a safety hazard, a health hazard, and a likely contaminant of a distillation apparatus used to separate the resolved enantiomers. On the other hand, the use of isopropenyl acetate as an acyl donor results in the production of isopropenyl alcohol, which is believed to tautomerize to acetone; acetone has a higher flash point (−17° C.), and is thus not as flammable as acetaldehyde, it is not a suspected carcinogen, and may prove more suitable to distill from the resolved enantiomers. Moreover, additional experiments shown in Table 12 have demonstrated that isopropenyl acetate is an efficient and selective acyl donor for PM, PE, PnP, PnB, and PPh.

TABLE 12

Transesterification of Glycol Ethers using VA and IPA as Acyl Donors

| Substrate | Acyl Donor[1] | Sub./Acyl Donor Ratio(v/v) | Sub./Acyl Donor Molar ratio | Lipase[2] (mg/mL) | Time (h) | Conv. (%) | (S)-Glycol Ether ee (%) | (R)-Glycol Ether Acetate ee (%) |
|---|---|---|---|---|---|---|---|---|
| PE | IPA | 51/49 | 1/1 | 6.7 | 20 | 51.6 | 72.4 | 95.6 |
| | IPA | 51/49 | 1/1 | 6.7 | 24 | 54.5 | 77.5 | 95.3 |
| | VA | 55/45 | 1/1 | 6.7 | 20 | 44.7 | 51.8 | 95.2 |
| | VA | 55/45 | 1/1 | 6.7 | 24 | 47.4 | 54.9 | 95.0 |
| PnP | IPA | 55/45 | 1/1 | 6.7 | 4 | 33.5 | 38.6 | 97.8 |
| | IPA | 55/45 | 1/1 | 6.7 | 20 | 54.9 | 98.7 | 91.8 |
| | IPA | 38/62 | 1/2 | 6.7 | 6 | 45.1 | 62.5 | 96.9 |
| | IPA | 38/62 | 1/2 | 6.7 | 20 | 58.7 | 98.0 | 88.1 |
| | VA | 59/41 | 1/1 | 6.7 | 1 | 32.0 | 35.1 | 97.4 |
| | VA | 59/41 | 1/1 | 6.7 | 6 | 52.6 | 85.2 | 93.6 |
| | VA | 59/41 | 1/1 | 6.7 | 20 | 60.7 | 98.3 | 74.3 |
| | VA | 42/58 | 1/2 | 6.7 | 1 | 39.3 | 47.2 | 96.7 |
| | VA | 42/58 | 1/2 | 6.7 | 6 | 56.5 | 95.5 | 90.1 |
| | VA | 42/58 | 1/2 | 6.7 | 20 | 66.1 | 97.7 | 66.8 |
| PnB | IPA | 57/43 | 1/1 | 6.7 | 4 | 40.1 | 53.3 | 96.7 |
| | IPA | 57/43 | 1/1 | 6.7 | 6 | 44.8 | 61.2 | 95.9 |
| | IPA | 57/43 | 1/1 | 6.7 | 20 | 58.0 | 99.5 | 81.7 |
| | IPA | 40/60 | 1/2 | 6.7 | 6 | 47.6 | 67.4 | 95.4 |
| | IPA | 40/60 | 1/2 | 6.7 | 20 | 58.7 | >99 | 79.2 |
| | IPA | 40/60 | 1/2 | 6.7 | 24 | 60.3 | >99 | 74.4 |
| | VA | 61/39 | 1/1 | 6.7 | 4 | 52.1 | 82.7 | 92.6 |
| | VA | 61/39 | 1/1 | 6.7 | 6 | 54.3 | 86.4 | 89.3 |
| | VA | 61/39 | 1/1 | 6.7 | 20 | 66.5 | >99 | 56.7 |
| | VA | 44/56 | 1/2 | 6.7 | 2 | 38.5 | 51.5 | 95.2 |
| | VA | 44/56 | 1/2 | 6.7 | 6 | 55.9 | >99 | 87.0 |
| | VA | 44/56 | 1/2 | 6.7 | 20 | 68.1 | >99 | 53.5 |
| PPh | IPA | 57/43 | 1/1 | 6.7 | 6 | 29.8 | 51.3 | 96.4 |
| | IPA | 57/43 | 1/1 | 6.7 | 20 | 43.5 | 97.9 | 93.1 |
| | IPA | 57/43 | 1/1 | 6.7 | 24 | 44.1 | 98.2 | 92.0 |
| | IPA | 40/60 | 1/2 | 6.7 | 6 | 35.8 | 62.4 | 95.0 |
| | IPA | 40/60 | 1/2 | 6.7 | 20 | 44.5 | 96.1 | 90.5 |
| | IPA | 40/60 | 1/2 | 6.7 | 24 | 45.0 | 98.1 | 89.5 |

TABLE 12-continued

Transesterification of Glycol Ethers using VA and IPA as Acyl Donors

| Substrate | Acyl Donor[1] | Sub./Acyl Donor Ratio(v/v) | Sub./Acyl Donor Molar ratio | Lipase[2] (mg/mL) | Time (h) | Conv. (%) | (S)-Glycol Ether ee (%) | (R)-Glycol Ether Acetate ee (%) |
|---|---|---|---|---|---|---|---|---|
| | VA | 61/39 | 1/1 | 6.7 | 6 | 38.4 | 73.3 | 95.3 |
| | VA | 61/39 | 1/1 | 6.7 | 20 | 45.8 | 97.6 | 87.5 |
| | VA | 61/39 | 1/1 | 6.7 | 24 | 46.2 | 98.1 | 86.2 |
| | VA | 44/56 | 1/2 | 6.7 | 4 | 39.9 | 73.6 | 93.7 |
| | VA | 44/56 | 1/2 | 6.7 | 6 | 43.1 | >99 | 92.8 |
| | VA | 44/56 | 1/2 | 6.7 | 20 | 47.6 | 98.1 | 81.7 |

[1]Acyl donors examine: isopropenyl acetate (IPA), vinyl acetate (VA).
[2]*Candida antarctica* lipase type B, carrier fixed, available commercially as Chirazyme L-2, c.-f., C2, lyo (~10 U/mg, Roche Molecular Biochemicals)

Ratio of Substrate to Acyl Donor: Controlling Extent of Substrate Conversion

CAL-B catalyzed transesterification of PM and PPh was demonstrated at substrate loadings of up to 80% and 84%, respectively. The remaining volume of the reactions was vinyl acetate (as the acyl donor). Limiting the amount of the acyl donor is an effective method to control the extent of substrate conversion; thus, the amount of the acyl donor is supplied in quantity sufficient to allow for slightly less than or slightly greater than 50% substrate conversion. This concept also emphasizes the use of highest substrate concentration allowable for the desired extent of conversion, thereby maximizing volumetric productivity.

Additional experiments examined the transesterification of glycol ether substrates at various ratios of acyl donor, where vinyl acetate was the acyl donor; the results are shown in Table 13 below.

TABLE 13

Transesterification of glycol ether substrates at various ratios of vinyl acetate as acyl donor

| Substrate | Acyl Donor | Sub./Acyl Donor Ratio | Temp. (° C.) | Enzyme Conc.[1] (mg/ml) | Time (h) | Conv. (%) | (S)-glycol ether ee (%) | (R)-Acetate ee (%) |
|---|---|---|---|---|---|---|---|---|
| PM | VA | 50/50 | 30 | 1.0 | 2 | 59.9 | n.d.[2] | 94.8 |
| | | | | | 22 | 84.3 | n.d. | 56.2 |
| PM | VA | 70/30 | 30 | 1.0 | 2 | 59.6 | n.d. | 94.3 |
| | | | | | 22 | 68.7 | n.d. | 81.6 |
| PnB | VA | 50/50 | 30 | 1.0 | 2 | 51.9 | 75.3 | 86.2 |
| | | | | | 22 | 70.5 | 99.0 | 47.6 |
| PnB | VA | 70/30 | 30 | 1.0 | 2 | 52.4 | 79.0 | 88.1 |
| | | | | | 6 | 59.9 | 99.0 | 76.3 |
| PE | VA | 50/50 | 30 | 1.0 | 4 | 39.6 | 95.7 | 95.7 |
| | | | | | 22 | 52.3 | 77.2 | 94.3 |
| PE | VA | 70/30 | 30 | 1.0 | 4 | 33.8 | 32.9 | 95.9 |
| | | | | | 22 | 39.6 | 45.4 | 95.7 |
| PiP | VA | 50/50 | 30 | 1.0 | 2 | 53.8 | 73.2 | 87.7 |
| | | | | | 22 | 65.4 | 95.1 | 73.2 |
| PiP | VA | 70/30 | 30 | 1.0 | 2 | 43.9 | 50.4 | 91.1 |
| | | | | | 22 | 63.6 | 96.9 | 79.4 |
| PnP | VA | 50/50 | 30 | 1.0 | 2 | 48.7 | 70.3 | 94.4 |
| | | | | | 22 | 67.6 | 99.0 | 59.7 |
| PnP | VA | 70/30 | 30 | 1.0 | 2 | 47.5 | 67.6 | 94.6 |
| | | | | | 5 | 58.4 | 95.4 | 89.0 |
| PPh | VA | 50/50 | 30 | 1.0 | 2 | 38.9 | 74.7 | 94.9 |
| | | | | | 22 | 52.5 | 99.0 | 68.0 |
| PPh | VA | 70/30 | 30 | 1.0 | 2 | 33.3 | 62.1 | 95.9 |
| | | | | | 6 | 46.0 | 99.0 | 92.2 |
| PtB | VA | 73/27 | 30 | 6.7 | 6 | 41.6 | 54.4 | >99 |
| | | | | | 20 | 55.6 | 96.5 | >99 |
| PtB | VA | 76/24 | 30 | 6.7 | 6 | 41.8 | 54.9 | >99 |
| | | | | | 20 | 54.5 | 91.6 | >99 |

[1]*Candida antarctica* lipase type B, available commercially as Chirazyme L-2, lyo (~120 U/mg, Roche Molecular Biochemicals). An immobilized form, as Chirazyme L-2, c.-f., C2, lyo (~10 U/mg, Roche Molecular Biochemicals) was used in reactions containing PtB as substrate.
[2]n.d., not determined.

Example 8

Recycling of Catalyst

The enzyme catalyst for either hydrolysis or transesterification can be recycled. The following experiments were undertaked to evaluate and optimize different parameters for recycling CAL-B when used in enantioselective hydrolysis of propylene glycol ether acetates.

Enzyme recycling was examined in aqueous 0.5 ml reactions containing PMA at a concentration of 25, 35 and 45% (v/v) and 13 mg/ml Chirazyme L-2, c.-f., C2, (approx. 10 U/mg). The reactions were incubated at 40° C. with rotary shaking at 300 rpm. Analysis was conducted over the course of a 24 h cycle, at which time, the reaction solution was removed and new buffer containing substrate was introduced to the original immobilized enzyme to start the next reaction cycle. At substrate concentration of 35% and 45%, the resolution was incomplete by cycle 3 with both enzymes yielding (S)-PMA in purity not higher than 92% ee. In contrast, reactions containing 25% PMA typically resolved (S)-PMA to >96-98% ee through 6 reaction cycles. Additional enzyme recycling studies were conducted at 20 and 25% substrate loading. For Chirazyme L-2, c.-f. C2, the enantiopurity of (S)-PMA was approx. 97% ee over the course of 30 reaction cycles in experiments conducted with 20% or 25% substrate concentration.

Scale-up of PMA resolution was done at 1.5l reaction volume in a BioFlo 3500 Fermentor (New Brunswick Scientific) at a substrate concentration of 25% (v/v) PMA. At the initial enzyme loading of 26.6 mg/ml Chirazyme L-2, c.-f., C2 (approx. 280 U/ml), resolution of 25% PEA was observed for up to 15 cycles with the length of each reaction cycle ranging from about 2 to 5 hours. At the end of each cycle, agitation was stopped and the settled immobilized CAL-B biocatalyst was retained in a reactor while the resolved reaction matrix was removed. Fresh buffer containing racemic PMA was added to the reactor to initiate a next cycle. No additional enzyme was added over the course of 15 cycles of resolution. The average enantiopurities of the (S)-PMA and (R)-PM recovered after methylene chloride extraction for the 15 cycles of resolution were >99.5% ee and >85% ee, respectively.

Immobilized CAL-B (Chirazyme L-2, c.-f. C2; approximately 240 U/ml) was used for several different enzyme recycling experiments with PEA as the substrate; these experiments were both laboratory scale (<5 ml) and at scale of 1.5-L. In one experiment, resolution of 20% (v/v) PEA in a 1 ml reaction volume was observed for three different enzyme loadings and for greater than 15 cycles, where the cycle time was generally about 24 hours. In this experiment, the reaction matrix was removed from immobilized CAL-B at the end of each cycle and analyzed, and fresh reaction matrix was added to the immobilized enzyme to initiate the next cycle. The reaction mixtures were incubated at about 40° C. The results, shown in FIG. 6, indicate that under the experimental conditions utilized, very good resolution of (S)-PEA can be observed for several cycles, and that higher enzyme concentrations result in higher resolution for a greater number of cycles.

Figure 7:
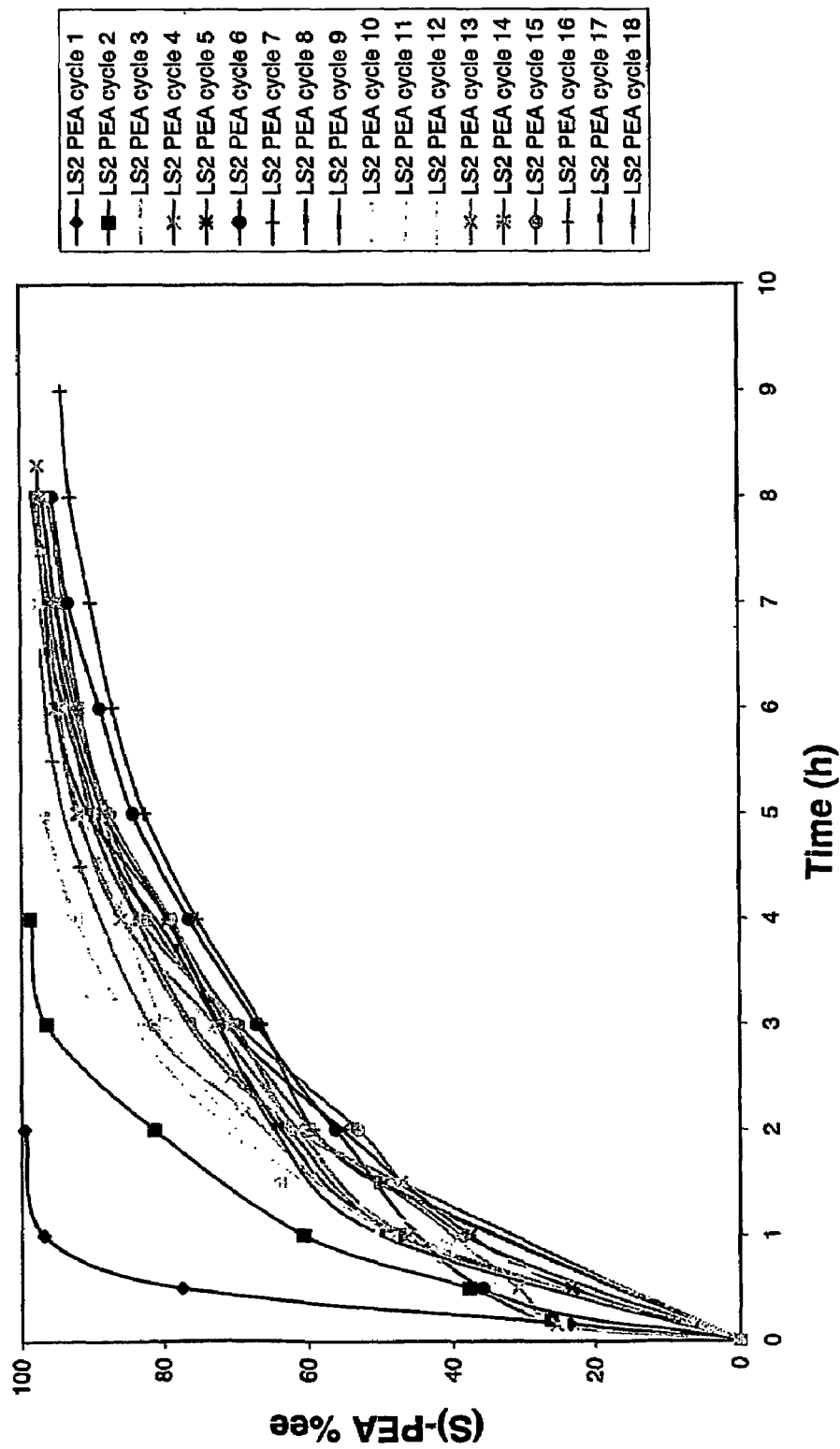
FIG. 7 shows enzyme recycle for PEA hydrolysis under scale-up conditions. The resolution of PEA (expressed as % ee) is shown as a function of incubation time, where each cycle was monitored during the course of the reaction by removing and analyzing samples; the length of each cycle varied from about 2 hours to about 9 hours. The reaction mixture was 1.5 l, PEA was present at 20% v/v, and the enzyme, immobilized CAL-B, was retained in a reactor from which the spent reaction mixture was removed at the end of a cycle, and fresh reaction mixture added to initiate a new cycle. New enzyme (10% of initial loading) was added when the reaction slowed at cycles 8, 10, 16, and 25.
Figure 8:
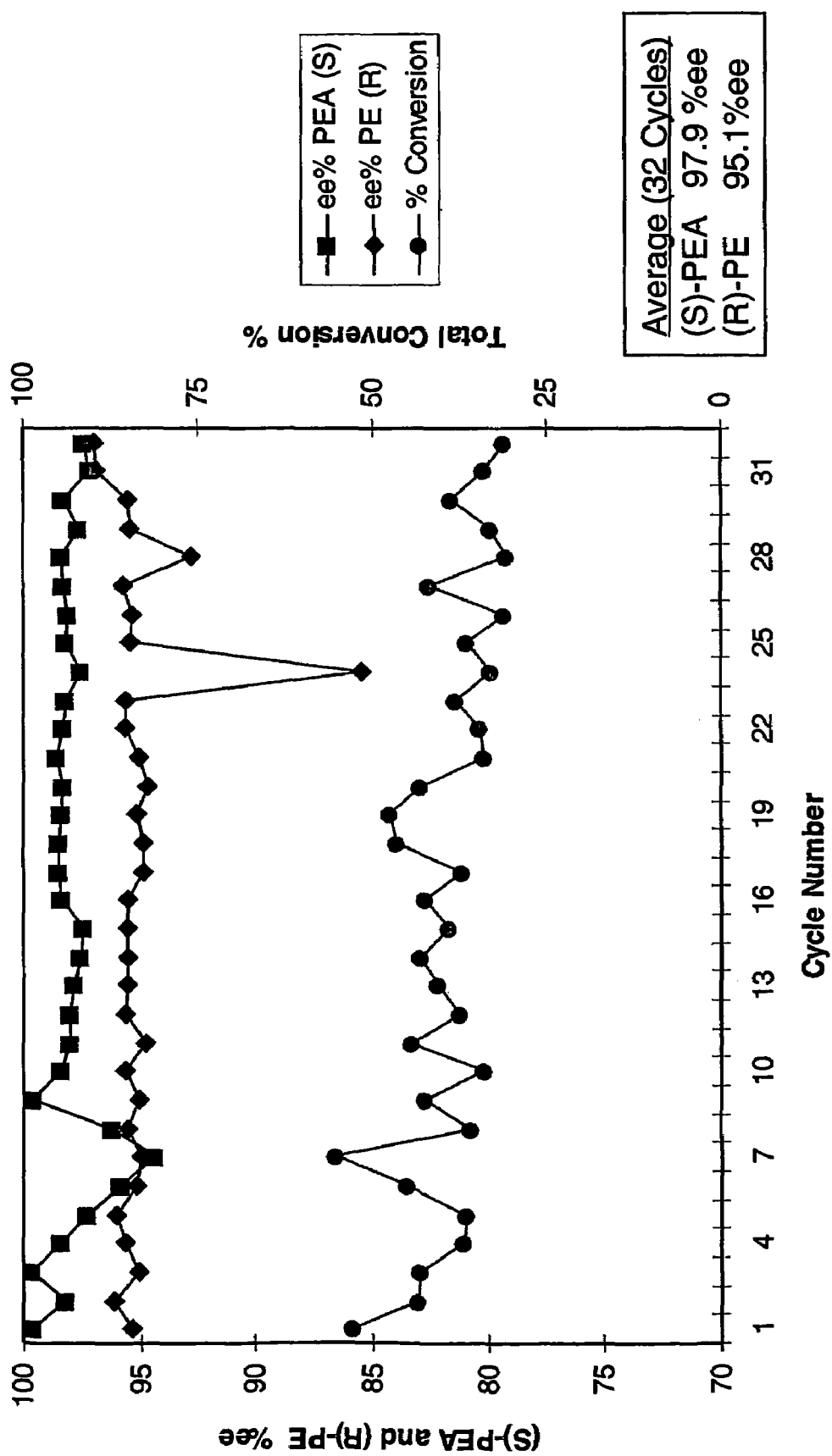
FIG. 8 shows enzyme recycling for PEA hydrolysis under scale-up conditions, for up to 32 cycles. The resolution of both (S)-PEA and (R)-PE (expressed as % ee) and the total conversion (expressed as %) is shown as a finction of cycle number. The reaction mixture was 1.5 l, PEA was present at 20% v/v, and the enzyme, immobilized CAL-B, was retained in a reactor from which the spent or resolved reaction mixture was removed at the end of a cycle, and fresh reaction mixture added to initiate a new cycle. Each cycle was monitored during the course of the reaction (similar to the reactions shown in FIG. 7), and the last sample used to calculate the resolutions and conversion.

In another experiment, the resolution of 20% (v/v) PEA was scaled to a 1.5-L reaction volume in a BioFlo 3500 Fermentor (New Brunswick Scientific). Biocatalyst recycle allowed resolution with CAL-B for over 30 cycles; the length of each cycle varied from about 2 to about 9 hours. In this experiment, the reaction matrix was removed from immobilized CAL-B in a reactor at the end of the cycle and analyzed, and fresh reaction matrix was added to the immobilized enzyme to initiate the next cycle. The reaction mixture was maintained at pH 7.2 (by addition of 20% sodium hydroxide) and incubation wat at 37° C. Enantiopurity of products was monitored by removing and analyzing a sample during the course of each cycle. The results of the first 18 cycles are shown in FIG. 7. As the reaction cycle time required for substrate resolution increased, fresh enzyme (10% of the original loading) was added to the reactor, this occurred at cycles 8, 10, 16, and 25. The performance over 32 cycles of PEA resolution is shown in FIG. 8. The last sample of each cycle was used to calculate the resolution of both (S)-PEA and (R)-PE (expressed as % ee) and the total conversion (expressed as %). The results are shown in FIG. 8, and demonstrate that under scale-up conditions, very good resolution of both (S)-PEA and (R)-PE, as well as high levels of conversion, can be observed over several cycles. Furthermore these experiments demonstrate effective recycle of Chirazyme L-2, c.-f. C2 under scale-up conditions which provided a significant reduction in the enzyme cost contribution per cycle; additional enzyme recycle could provide more favorable process efficiency and overall product economics. Transesterification based resolution of high concentrations of PPh has been demonstrated under the following conditions at 1.0-L scale with Chirazyme L-2, c.-f. C2 (6.6 mg/ml) using vinyl acetate as acyl donor. Reactions converted to <50% are constructed with a PPh/VA ratios of 70/30 to 76/30 and proceed to yield (R)-PPhA in high % ee at room temperature. For reactions where >50% conversion is desired, a PPh/VA ratio of 70/30 has been used and higher enantioselectivity is achieved at 4° C. with typically product enantiopurity for (S)-PPh and (R)-PPhA of >90% ee and >95% ee, respectively. Agitation is provided by magnetic stirring bar and separation of the immobilized enzyme from the reaction volume can be achieved by filtration. Enzyme recycling under these conditions can be achieved for 5-8 cycles.

Additional reactions were conducted under transesterification conditions at 1.0-liter scale with different PGEA substrates to resolve the corresponding (S)-PGAE and (R)-PGAEA in high enantiopurity. The enzyme in these studies was reused for multiple cycles of batch resolution. Conditions and resolution performance are summarized in Table 14.

TABLE 14

| Batch No. | Substrate | Acyl donor | Substrate/ Acyl donors (v/v) | Temp. (° C.) | Theo. Conv. % (observed conv. %) | CAL-B, L-2, C2 (mg/ml) | No. Cycles | (S)-Glycol Ether (ee %) | (R)-Glycol Ether Acetate (ee %) |
|---|---|---|---|---|---|---|---|---|---|
| 1 | PM | VA | 62/38 | 4 | 65 (68) | 10.00 | 10 | 95.47 | 80.02 |
| 2 | PM | IPA | 69/31 | 4 | 40 (~43) | 13.4 | 3 | 27.56 | 95.44 |
| 3 | PnP | VA | 69/31 | 4 | 65 (~63) | 10 | 21 | 98.6 | 88.2 |

TABLE 14-continued

| Batch No. | Substrate | Acyl donor | Substrate/ Acyl donors (v/v) | Temp. (° C.) | Theo. Conv. % (observed conv. %) | CAL-B, L-2, C2 (mg/ml) | No. Cycles | (S)- Glycol Ether (ee %) | (R)-Glycol Ether Acetate (ee %) |
|---|---|---|---|---|---|---|---|---|---|
| 4 | PnP | VA | 78.5/21.5 | 4 | 40 (~44) | 3.3-6.6 | 8 | 47.55 | 97.1 |
| 5 | PnB | IPA | 69/31 | 4 | 61 (~59) | 6.7-18.6 | 7 | 99.9 | 92.1 |
| 6 | PnB | IPA | 73/27 | 4 | 50 (~45) | 6.7 | 8 | 55.7 | 97.7 |
| 7 | PtB | VA | 73/27 | 24 | 60 (~56) | 6.7 | 12 | 95.5 | 99.6 |
| 8 | PPh | VA | 76/24 | 20 | 56 (~45) | 6.7 | 5 | 62.64 | 96.06 |
| 9 | PPh | VA | 70/30 | 4 | 66 (~51) | 6.7 | 2 | 78.9 | 97.08 |

Example 9

Racemic PMA as a Chiral Acyl Donor

Methods:

To 1.8 ml vials were added the following amounts of racemic 1-tert-butoxy-2-propanol (PtB), listed acyl donor and Chirazyme L-2 C2 as biocatalyst (enzyme). The approximate theoretical conversion of the PtB indicated is based on the molar ratio of substrate and acyl donor. Theoretical conversion values of greater than 100% refer to the stoichiometric excess of acyl donor provided.

| Reaction Number | Acyl Donor (% volume) | Enzyme (mg/ml) | Substrate | PtB (uL) | Acyl Donor (uL) | Theo. Conv %. |
|---|---|---|---|---|---|---|
| 1 | PMA 50% | 13.4 | PtB | 500 | 500 | 104 |
| 2 | PMA 70% | 13.4 | PtB | 700 | 300 | 45 |
| 3 | Vinyl Acetate 70% | 13.4 | PtB | 700 | 300 | 70 |
| 4 | Ethyl Acetate 70% | 13.4 | PtB | 700 | 300 | 66 |

The reaction mixtures of 1.0 ml total volume were incubated at 4° C. with shaking. Subsamples were removed periodically over 65 hours and analyzed by chiral GC to monitor the conversion of PtB and the enantiopurity of the resulting acetate product, 1-tert-butoxy-2-propanol acetate (PtBA) as well as PMA and PM.

Results:

The results shown in Table 15 demonstrate that DOW-ANOL PMA can serve as an acyl donor in the enzymatic transesterification of PtB to yield (R)-PtBA in high enantiopurity (>99% ee). In addition to the highly selective acylation of (R)-PtB, enzyme selectivity was also observed in the utilization of the chiral acyl donor, PMA. Reactions 1 and 2 indicate that CAL-B preferentially utilized the (R)-PMA as acyl donor leading to the formation of (R)-PM as by product and partial resolution of (S)-PMA concurrent with PtB acylation. The ratio of glycol ether substrate (e.g., PtB) to the chiral PMA as well as removal of the volatile (R)-PM can, in principle, be used to control the extent of reaction conversion. For example, reactions containing PtB/PMA at volumetric ratios of 50:50 (Reaction 1) and 70:30 (Reaction 2) yielded R-PtBA of 99% ee in at PtB conversions of 31% and 20%, respectively. It should also be noted that enzyme concentration, reaction time and incubation temperature can be used to control reaction rate and enantioselectivity. The results are shown in Table 15.

TABLE 15

| Reaction | Time (h) | (S)-PtB (% ee) | (R)-PtBA (% ee) | PtB Conv. (%)[1] | (R)-PM (% ee) | (S)-PMA (% ee) | PMA Conv. (%) |
|---|---|---|---|---|---|---|---|
| 1 | 0 | 0 | 0 | 0 | 0 | 0 | 0 |
|   | 18 | 22 | >99 | 23 | 93 | 22 | 12 |
|   | 24 | 25 | >99 | 25 | 96 | 24 | 13 |
|   | 47 | 32 | >99 | 30 | 86 | 28 | 16 |
|   | 65 | 34 | >99 | 31 | 84 | 28 | 17 |
| 2 | 0 | 0 | 0 | 0 | 0 | 0 | 0 |
|   | 18 | 13 | >99 | 15 | 94 | 39 | 19 |
|   | 24 | 15 | >99 | 17 | 92 | 43 | 21 |
|   | 47 | 17 | >99 | 19 | 87 | 49 | 24 |
|   | 65 | 18 | >99 | 20 | 84 | 48 | 26 |
| 3 | 0 | 0 | 0 | 0 | —[2] | — | — |
|   | 18 | 73 | >99 | 49 | — | — | — |
|   | 24 | 84 | >99 | 53 | — | — | — |
|   | 47 | 95 | >99 | 56 | — | — | — |
|   | 65 | 94 | >99 | 56 | — | — | — |
| 4 | 0 | 0 | 0 | 0 | — | — | — |
|   | 18 | 11 | >99 | 13 | — | — | — |
|   | 24 | 12 | >99 | 15 | — | — | — |
|   | 47 | 15 | >99 | 17 | — | — | — |
|   | 65 | 15 | >99 | 17 | — | — | — |

[1] PtB conversion is reported according to PtBA formation and is based on GC-FID (peak area) analysis and is defined as [total PtBA/total PtBA + total PtB] × 100.
[2] Acyl donor byproducts were not measured in reactions containing vinyl acetate or ethyl acetate.

Example 10

Racemic PMA as a Chiral Acyl Donor

Methods:

The effects of varying the ratio of glycol ether substrate and acyl donor were further examined. Reaction mixtures containing PtB/PMA volumetric ratios of 30:70, 40:60, 50:50, 60:40 and 70:30 were used to examine the extent of conversion and the resolution obtained for R-PtBA, S-PtB, R-PM and S-PMA. The reactions contained, in 1.8 ml vials, the following amounts of racemic PtB, PMA as acyl donor and Chirazyme L-2 C2 as biocatalyst (enzyme):

| Reaction Number | Substrate/Acyl Donor (Ratio) | Enzyme (mg/ml) | PtB (uL) | PMA (uL) | Theo. Conv (%) |
|---|---|---|---|---|---|
| 1 | PtB/PMA (30:70) | 13.4 | 300 | 700 | 244.09 |
| 2 | PtB/PMA (40:60) | 13.4 | 400 | 600 | 156.91 |

-continued

| Reaction Number | Substrate/Acyl Donor (Ratio) | Enzyme (mg/ml) | PtB (uL) | PMA (uL) | Theo. Conv (%) |
|---|---|---|---|---|---|
| 3 | PtB/PMA (50:50) | 13.4 | 500 | 500 | 104.61 |
| 4 | PtB/PMA (60:40) | 13.4 | 600 | 400 | 69.74 |
| 5 | PtB/PMA (70:30) | 13.4 | 700 | 300 | 44.83 |

Theoretical conversion values of greater than 100% refer to the stoichiometric excess of acyl donor provided. The 1.0 ml reaction mixtures were incubated at 4° C. with shaking. Subsamples were removed over a 48 hour period and analyzed by chiral GC to monitor the conversion of PtB and the enantiopurity of PtB, PtBA, PMA and PM.

Results:

The reactions containing different volumetric ratios of PtB/PMA showed varying extents of PtB conversion resulting in the resolution of R-PtBA in >99% ee and (S)-PtB of varying enantiopurity (see Table 15). The reaction containing PtB/PMA at a 30:70 ratio showed the highest conversion of PtB and resolved it to higher enantiopurity than reactions containing increasing proportions of PtB and lower amounts of acyl donor. In addition, the selective utilization of R-PMA as chiral acyl donor resulted in the effective resolution of R-PM and enrichment in the S-PMA enantiomer. The results are shown in Table 16.

TABLE 16

| Reaction | Time (h) | (S)-PtB (% ee) | (R)-PtBA (% ee) | PtB Conv. (%)[1] | (R)-PM (% ee) | (S)-PMA (% ee) | PMA Conv. (%)[2] |
|---|---|---|---|---|---|---|---|
| 1 | 0 | 1 | 71 | 1 | 91 | 1 | 0 |
|   | 2 | 18 | 98 | 19 | 93 | 8 | 5 |
|   | 5 | 36 | >99 | 32 | 87 | 12 | 7 |
|   | 20.5 | 57 | >99 | 42 | 68 | 12 | 10 |
|   | 51 | 52 | >99 | 40 | 50 | 7 | 11 |
| 2 | 0 | 0 | 34 | 0 | 0 | 0 | 0 |
|   | 2 | 16 | >99 | 17 | 93 | 10 | 6 |
|   | 5 | 30 | >99 | 29 | 88 | 16 | 10 |
|   | 20.5 | 45 | >99 | 38 | 67 | 17 | 14 |
|   | 51 | 50 | >99 | 39 | 39 | 12 | 15 |
| 3 | 0 | 0 | 18 | 0 | 0 | 0 | 0 |
|   | 2 | 12 | >99 | 14 | 94 | 12 | 7 |
|   | 5 | 23 | 98 | 24 | 90 | 21 | 12 |
|   | 20.5 | 36 | >99 | 33 | 72 | 25 | 17 |
|   | 51 | 40 | >99 | 34 | 49 | 19 | 19 |
| 4 | 0 | 0 | 8 | 0 | 0 | 0 | 0 |
|   | 2 | 7 | >99 | 8 | 93 | 10 | 6 |
|   | 5 | 17 | 98 | 19 | 90 | 25 | 14 |
|   | 20.5 | 28 | >99 | 27 | 74 | 34 | 22 |
|   | 51 | 31 | >99 | 29 | 51 | 26 | 24 |
| 5 | 0 | 0 | 6 | 0 | 0 | 0 | 0 |
|   | 2 | 4 | 98 | 6 | 93 | 10 | 6 |
|   | 5 | 11 | 98 | 14 | 91 | 28 | 16 |
|   | 20.5 | 20 | >99 | 21 | 77 | 45 | 26 |
|   | 51 | 22 | >99 | 23 | 56 | 37 | 29 |

[1] PtB conversion is reported according to PtBA formation and is based on GC-FID (peak area) analysis and is defined as [total PtBA/total PtBA + total PtB] × 100. The precision for the calculated conversion is approximately ±10%.
[2] PMA conversion is reported is based on GC-FID (peak area) analysis and is defined as: [total PM/total PM + total PMA] × 100. The precision for the calculated conversion is approximately ±10%.

Example 11

Racemic PMA as a Chiral Acyl Donor

Experiment A.

Methods:

Based on the extent of conversion seen in previous reactions, the effect of stripping PM under reduced pressure was examined for a 100-ml reaction containing PtB/PMA at a volumetric ratio of 60:40. Following removal of PM, the reaction was charged with additional PMA. The batch-wise removal of the R-PM from reaction #1 and subsequent addition of new acyl donor (PMA) was used to demonstrate the concept of a reactive distillation scenario. Control reactions to assess extent of conversion and product enantiopurity without PM stripping received (i) a single addition of PMA (reaction #2) and (ii) batch-wise PMA additions (reaction #3). The reactions contained the following amounts of racemic PtB, PMA as acyl donor and Chirazyme L-2 C2 as biocatalyst (enzyme):

| Reaction Number | Reaction Conditions | Enzyme (mg/ml) | Substrate | Substrate Volume (mL) | Acyl Donor Volume (mL) | Stripping Intervals |
|---|---|---|---|---|---|---|
| 1 | Stripped | 40.2 | PtB | 60 | 40 [1] | 1.5 hr |
| 2 | Control #2 | 40.2 | PtB | 60 | 40 [2] | — |
| 3 | Control #3 | 40.2 | PtB | 60 | 40 [3] | — |

[1] Reaction 1 received 40 ml PMA aliquots to initiate the reaction and following PM-stripping at 1.5, 3.0 and 4.5 hours.
[2] Control reaction 2 received only 40 ml of PMA as acyl donor to initiate the reaction.
[3] Control reaction 3 was not stripped but received 40 ml PMA aliquots to initiate the reaction and after sampling at 1.75, 3.25, and 4.75 hours.

The reaction mixtures were incubated in 250 ml glass vessels at 30° C. with stirring. Stripping of reaction 1 was carried out at 1.5 hour intervals as follows: The liquid phase was decanted from the immobilized enzyme into a round bottom flask and subjected to rotary evaporation under reduced pressure at 74° C. to remove PM. Following PM removal, reaction contents were cooled (30° C.), sampled and additional PMA provided.

Results:

The results shown in Table 17 show the final conversions of PtB to (R)-PtBA obtained in reaction 1 and reaction 3 were 70% and 46%, respectively. This difference is due to the accumulation of acyl donor by-product (PM) in reaction 3 and the unfavorable reaction equilibrium inhibits further conversion. The (R)-PtBA formed in both reactions was >99% ee. However, the higher conversion achieved by stripping the chiral by-product (R)-PM allowed for the resolution of (S)-PtB to >84% ee in reaction 1, while (S)-PtB was resolved to only 65.6% ee in reaction 3. The fact that reaction 1 showed a PtB conversion of 70%, yet still contained (R)-PtBA of >99% ee is due to partial loss of PtB from the reaction during the stripping process. The enantioselective utilization of PMA as acyl donor is evident by analysis of the (R)-PM recovered from reaction 1 which ranged in enantiopurity from 66% ee to 74% ee for material condensed at the 1.5 h, 3.0 h and 4.5 h time points.

While this experiment was conducted in a batch mode with off-line by-product removal the concept is valid and could be extended for continuous product removal in a reactive distillation scenario. The recovered (R)-PM can be upgraded in a second resolution with vinyl acetate as acyl donor to yield (R)-PMA of high enantiopurity.

TABLE 17

Experiment A

| Reaction Number | Time (h) | (S)-PtB (% ee) | (R)-PtBA (% ee) | PtB Conv. (%)[1] | (S)-PMA (% ee) | PMA Conv. (%)[2] | Stripped (R)-PM (% ee)[3] |
|---|---|---|---|---|---|---|---|
| 1 | 0 | 0 | 0 | 0 | 0 | 0 | |
|   | 0.5 | 10 | >99% | 12 | 16 | 9 | |
|   | 1 | 16 | >99% | 18 | 24 | 14 | |
|   | 1.5 | 21 | >99% | 22 | 29 | 16 | 70 |
|   | 1.75 | 22 | >99% | 27 | 7 | 3 | |
|   | 2 | 35 | >99% | 34 | 12 | 7 | |
|   | 2.5 | 40 | >99% | 38 | 14 | 8 | |
|   | 3 | 44 | >99% | 40 | 15 | 9 | 74 |
|   | 3.25 | 46 | >99% | 53 | 6 | —[4] | |
|   | 3.5 | 60 | >99% | 56 | 8 | — | |
|   | 4 | 65 | >99% | 58 | 8 | — | |
|   | 4.5 | 71 | >99% | 59 | 8 | — | 66 |
|   | 4.75 | 68 | >99% | 67 | 4 | — | |
|   | 20.5 | 85 | 99 | 70 | 3 | — | |
| 2 | 0 | 0 | 0 | 0 | 0 | 0 | |
|   | 0.5 | 10 | 99 | 13 | 16 | 9 | |
|   | 1 | 17 | >99% | 19 | 24 | 13 | |
|   | 1.5 | 21 | >99% | 22 | 29 | 16 | |
|   | 1.75 | 22 | >99% | 23 | 29 | 17 | |
|   | 2 | 25 | >99% | 25 | 31 | 18 | |
|   | 2.5 | 26 | >99% | 26 | 32 | 19 | |
|   | 3 | 27 | >99% | 27 | 32 | 20 | |
|   | 3.25 | 28 | >99% | 27 | 32 | 20 | |
|   | 3.5 | 28 | >99% | 27 | 32 | 21 | |
|   | 4 | 29 | >99% | 28 | 32 | 21 | |
|   | 4.5 | 29 | >99% | 28 | 31 | 21 | |
|   | 4.75 | 29 | >99% | 28 | 31 | 21 | |
|   | 20.5 | 36 | 99 | 32 | 15 | 26 | |
| 3 | 0 | 0 | 0 | 0 | 0 | 0 | |
|   | 0.5 | 10 | >99% | 12 | 15 | 8 | |
|   | 1 | 17 | >99% | 18 | 23 | 13 | |
|   | 1.5 | 21 | >99% | 22 | 28 | 16 | |
|   | 1.75 | 22 | >99% | 23 | 12 | 8 | |
|   | 2 | 29 | >99% | 28 | 15 | 9 | |
|   | 2.5 | 33 | >99% | 30 | 17 | 11 | |
|   | 3 | 36 | >99% | 32 | 18 | 12 | |
|   | 3.25 | 37 | >99% | 33 | 11 | 8 | |
|   | 3.5 | 41 | >99% | 35 | 12 | 8 | |
|   | 4 | 44 | >99% | 37 | 13 | 9 | |
|   | 4.5 | 47 | >99% | 38 | 13 | 9 | |
|   | 4.75 | 47 | >99% | 38 | 9 | 7 | |
|   | 20.5 | 66 | 99 | 46 | 6 | 9 | |

[1] PtB conversion is reported according to PtBA formation and is based on GC-FID (peak area) analysis and is defined as [total PtBA/total PtBA + total PtB] × 100. The precision for the calculated conversion is approximately ±10%. The PtB conversions of >50% in reaction 1 (concurrent with (R)-PtBA of >99% ee) are in part due is partial loss of PtB from the reaction during the stripping process.
[2] PMA conversion is reported is based on GC-FID (peak area) analysis and is defined as: [total PM/total PM + total PMA] × 100. The precision for the calculated conversion is approximately ±10%.
[3] Stripped (R)-PM refers to the PM fraction removed from the reaction by rotary evaporation.
[4] nd, Not determined Experiment B.

Methods.

A second experiment was conducted to examine the effect of stripping PM under reduced pressure in 100 ml reaction containing PtB/PMA at a volumetric ratio of 50:50. Experimental conditions were identical to those described in Experiment A except that 50 ml of PMA was provided as acyl donor when specified. The reactions contained the following components:

| Reaction Number | Reaction Conditions | Enzyme (mg/ml) | Substrate | Substrate Volume (mL) | Acyl Donor Volume (mL) | Stripping Intervals |
|---|---|---|---|---|---|---|
| 1 | Stripped | 40.2 | PtB | 50 | 50[1] | 1.5 hr |
| 2 | Control #2 | 40.2 | PtB | 50 | 50[2] | — |
| 3 | Control #3 | 40.2 | PtB | 50 | 50[3] | — |

[1] Reaction 1 received 50 ml PMA aliquots following PM-stripping at 1.5, 3.0 and 4.5 hours.
[2] Control reaction 2 received only 50 ml of PMA as acyl donor to initiate the reaction.
[3] Control reaction 3 was not stripped but received additional 50 ml PMA aliquots scheduled according to those of Reaction 1

Results:

Results of Experiment B (Table 18) confirm the effects shown in Experiment A. The final conversions of PtB to (R)-PtBA obtained in reaction 1 and reaction 3 were 77% and 43%, respectively. Even in the presence of 50% acyl donor, the accumulation of acyl donor by-product (PM) in reaction 3 inhibits conversion beyond levels observed in Experiment A. Again, the (R)-PtBA formed in both reactions reached >99% ee. The higher conversion achieved by stripping the (R)-PM in reaction 1 also allowed for the resolution of (S)-PtB to >80% ee within 5 hours, while (S)-PtB was resolved to only 60% ee in reaction 3. The removal of acyl donor byproduct represents a clear advantage in achieving higher conversion of substrate to products of higher enantiopurity. The enantiopurity of the stripped (R)-PM recovered from reaction 1 in Experiment B ranged from 69% ee to 87% ee. The effect of stripping is evident by comparing the extent of PtB conversion and product enantiopurities of reactions 1 and 3.

TABLE 18

Experiment B

| Reaction Number | Time (h) | (S)-PtB (% ee) | (R)-PtBA (% ee) | PtB Conv. (%)[1] | (S)-PMA (% ee) | PMA Conv. (%)[2] | Stripped (R)-PM (% ee)[3] |
|---|---|---|---|---|---|---|---|
| 1 | 0 | 0 | 0 | 0 | 0 | 0 | |
|   | 0.5 | 11 | 98 | 14 | 12 | 7 | |
|   | 1 | 21 | >99% | 21 | 19 | 11 | |
|   | 1.5 | 27 | >99% | 26 | 23 | 13 | 87 |
|   | 2 | 45 | >99% | 46 | 10 | 4 | |
|   | 2.5 | 55 | >99% | 50 | 11 | 5 | |
|   | 3 | 59 | >99% | 51 | 11 | 5 | 70 |
|   | 4 | 77 | >99% | 69 | 5 | —[4] | |
|   | 4.5 | 79 | >99% | 70 | 5 | — | 69 |
|   | 5 | 80 | >99% | 76 | 3 | — | |
|   | 5.5 | 80 | >99% | 76 | 3 | — | |
|   | 6 | 83 | >99% | 77 | 3 | — | |
| 2 | 0 | 0 | 0 | 0 | 0 | 0 | |
|   | 0.5 | 11 | 98 | 13 | 11 | 6 | |
|   | 1 | 20 | >99% | 21 | 18 | 10 | |
|   | 1.5 | 26 | >99% | 26 | 22 | 13 | |
|   | 2 | 30 | >99% | 29 | 24 | 14 | |
|   | 2.5 | 33 | >99% | 30 | 25 | 15 | |
|   | 3 | 34 | 98 | 31 | 25 | 15 | |
|   | 4 | 37 | >99% | 33 | 24 | 15 | |
|   | 4.5 | 37 | >99% | 33 | 24 | 16 | |
|   | 5 | 38 | >99% | 33 | 23 | 17 | |
|   | 5.5 | 39 | >99% | 34 | 22 | 17 | |
|   | 6 | 39 | >99% | 34 | 22 | 18 | |
| 3 | 0 | 0 | 0 | 0 | 0 | 0 | |
|   | 0.5 | 10 | 98 | 13 | 11 | 6 | |
|   | 1 | 19 | 99% | 20 | 18 | 10 | |
|   | 1.5 | 26 | >99% | 25 | 22 | 12 | |

TABLE 18-continued

Experiment B

| Reaction Number | Time (h) | (S)-PtB (% ee) | (R)-PtBA (% ee) | PtB Conv. (%)[1] | (S)-PMA (% ee) | PMA Conv. (%)[2] | Stripped (R)-PM (% ee)[3] |
|---|---|---|---|---|---|---|---|
| | 2 | 32 | >99% | 30 | 12 | 7 | |
| | 2.5 | 37 | >99% | 33 | 13 | 8 | |
| | 3 | 42 | >99% | 35 | 14 | 9 | |
| | 4 | 51 | >99% | 40 | 10 | 7 | |
| | 4.5 | 54 | >99% | 41 | 10 | 7 | |
| | 5 | 57 | >99% | 43 | 7 | 5 | |
| | 5.5 | 58 | >99% | 43 | 7 | 6 | |
| | 6 | 60 | >99% | 43 | 7 | 6 | |

[1] PtB conversion is reported according to PtBA formation and is based on GC-FID (peak area) analysis and is defined as [total PtBA/total PtBA + total PtB] × 100. The precision for the calculated conversion is approximately ±10%. The PtB conversions of >50% in reaction 1 (concurrent with (R)-PtBA of >99% ee) are in part due to partial loss of PtB from the reaction during the stripping process.
[2] PMA conversion is reported is based on GC-FID (peak area) analysis and is defined as: [total PM/total PM + total PMA] × 100. The precision for the calculated conversion is approximately ±10%.
[3] Stripped (R)-PM refers to the PM fraction removed from the reaction by rotary evaporation.
[4] nd, Not determined Example 12

Preparation of (S)-1,2-Propanediol from (R,S)-1-tert-butoxy-2-propanol

Step (a): Enzymatic Resolution of (R,S)-1-tert-butoxy-2-propanol

To a 1.0-L reaction vessel containing 366 ml (R,S)-1-tert-butoxy-2-propanol (PtB) and 134 ml vinyl acetate was added 3.35 g of immobilized CAL-B as Chirazyme L-2 C2. The 500-ml reaction containing (R,S)-1-tert-butoxy-2-propanol and vinyl acetate at a volumetric ratio of 73:27 (sufficient for approximately 60% conversion of PtB to PtBA) was incubated at 30° C. with stirring. The yields and enantiopurities of products were monitored by chiral GC over the course of a 20-24 h incubation period. Yields of products typically indicated conversion of approximately 50% within 20 h, at which time the solvent phase of the reactions was separated from the immobilized enzyme particles by filtration. The immobilized enzyme was recycled as the acylation catalyst in this manner for over 10 cycles of resolution by introducing additional 500-ml volumes of (R,S)-1-tert-butoxy-2-propanol and vinyl acetate at a volumetric ratio of 73:27.

The results of GC analysis showed the recovered solvent phase of the reactions to contain the resolved products (R)-1-tert-butoxy-2-acetoxy propane (R-PtBA) in >99% ee and (S)-1-tert-butoxy-2-propanol (S-PtB) in >96% ee. Acetaldehyde was obtained as a side product of the enzymatic acylation. The chiral products were subsequently isolated by distillation as described in step (b).

Step (b): Separation of (S)-PtB/(R)-PtBA by Distillation

The chiral products from step (a) were purified in two steps. In the first step, acetaldehyde was removed from the reaction mixture. In a typical run, 3790 g acetaldehyde/(S)-PtB/(R)-PtBA mixture was placed in a 5-L round-bottom flask. The flask was attached to a vacuum distillation apparatus composed of a two-foot glass column packed with ¼" ceramic saddles and a magnetic refluxing condenser head with SR-1 as the coolant (set to −15° C.). The flask was heated to 47° C. at a pressure of 350 mm Hg with a 2/2 reflux/forwarding ratio. Most of the acetaldehyde was removed after 3.5 hours. The acetaldehyde-free (S)-PtB/(R)-PtBA mixture was then distilled in a similar distillation apparatus equipped with a six-foot column packed with ¼" ceramic saddles. In this step, water was used as the coolant. In a typical run, 4,033 g (S)-PtB/(R)-PtBA mixture were placed in the 5-L flask, which was then heated from 74° C. to 89° C. at pressures ranging from 6 to 36 mm Hg with a 2/1 reflux/forwarding ratio. Twenty-four cuts were taken. These cuts were analyzed by capillary GC and those of similar composition were combined. Combination b (Cuts 7-16) weighed 1,265 g and contained 98.4% (S)-PtB. Combination e (Cuts 20-24) weighed 1,990 g and contained 99.5% (R)-PtBA. Analysis of diluted samples of each combination (in water, 200:1 ratio) showed that both (S)-PtB and (R)-PtBA were present in >99.5% ee.

Step (c-1): Dealkoxylation of (S)-PtB to (S)-PG

In a 10-ml two-necked conical bottom flask were placed 5.0032 g (S)-PtB obtained in step (b) and 0.1888 g p-toluene sulfonic acid (p-TSA) catalyst. A condenser with an anhydrous $CaSO_4$ drying tube was attached to one of the necks of the flask. A septum was attached to the other neck of the flask. The flask was placed in a silicon oil bath heated to 100° C. The reaction was allowed to proceed for 13 hours while occasional samples were taken and analyzed by GC. After the reaction was completed, it was shown that 98.6% of the (S)-PtB had reacted, with a selectivity of 81.6% to (S)-PG (see Table 18). The (S)-PG product, diluted in water (200:1 ratio), was analyzed by chiral GC and found to be in >99.5% ee.

Step (c-2): Hydrolysis and Dealkoxylation of (R)-PtBA to (R)-PG

In a 10-ml two-necked conical bottom flask were placed 5.0375 g (R)-PtBA obtained in step (b), 15.0919 g distilled water, and 0.4671 g p-TSA catalyst. A condenser with an anhydrous $CaSO_4$ drying tube was attached to one of the necks of the flask. A septum was attached to the other neck of the flask. The flask was placed in a silicon oil bath heated to 100° C. The reaction was allowed to proceed for 33 hours while occasional samples were taken and analyzed by GC. After the reaction was completed, it was shown that 100% of the (R)-PtBA had reacted, with a selectivity of 86.5% to (R)-PG (see Table 18). The (R)-PG product, diluted in water (200:1 ratio), was analyzed by chiral GC and found to be in >99.5% ee.

Step (d): Isolation of (S)-PG from Dealkoxylation Products

In a 5-ml round-bottom flask was placed the product mixture from step (c-1) and a stir bar. A micro-flash distillation apparatus equipped with thermometer, vacuum connector, and receiver was attached to the flask. A heat gun was used to flash over the product at 84° C. -87° C. and 10 mm Hg. The isolated product was analyzed by GC and found to contain 89% PG. fared spectroscopy confirmed that the major component in the isolated product was PG with some carbonyl impurities, which were later identified by GC-MS as the mono- and di-acetates of propylene glycol. The isolated (S)-PG (diluted in water, 200:1 ratio) was analyzed by chiral GC and found to be in >99.5% ee.

Step (e): Improving Yield by Removing Residual Acetic Acid from (S)-PtB

The propylene glycol acetates described in the previous step were believed to have formed due to the presence of residual acetic acid in the (S)-PtB arising from partial cracking of (R)-PtBA in Step (b). With this in mind, a small amount of (S)-PtB was treated with a small amount of 10 N NaOH and then flashed distilled. The treated (S)-PtB was then used to repeat the experiment in Step (c-1) as shown in Table 19. This time the selectivity to (S)-1,2-propanediol was >95% (99.5% ee). IR analysis of the product after flash distillation as described above showed no acetate peaks. This demonstrated the detrimental effect of free acetic acid in the (S)-PtB. Those skilled in the art will recognize that the formation of acetic acid could be reduced or eliminated by conducting a more careful distillation in step (b).

TABLE 19

Dealkoxylation Results

| Reactant | Conversion % | Selectivity to (R) or (S) PG % | Temperature (° C.) | Reaction Time (Hr) | Catalyst | Wt % Catalyst (Based on reactant wt) | Water (molar excess) |
|---|---|---|---|---|---|---|---|
| (S)-PtB | 65.4 | 68.3 | 40–80 | 5.5 | styrenic bead* | 10.1 | n.a.** |
| (S)-PtB | 81 | 73.6 | 80 | 10.5 | styrenic bead* | 17 | n.a.** |
| (S)-PtB | 96.4 | 82.8 | 100 | 14.5 | styrenic bead* | 14 | n.a.** |
| (S)-PtB | 98.6 | 81.6 | 100 | 13 | p-TSA | 3.8 | n.a.** |
| (S)-PtB (NaOH treated) | 98.8 | 95.9 | 100 | 19 | p-TSA | 7.9 | n.a.** |
| (R)-PtB | 87.7 | 5.1 | 80 | 6.5 | styrenic bead* | 9.8 | n.a.** |
| (R)-PtB | 100 | 31.3 | 100 | 13.5 | p-TSA | 4.1 | 1 |
| (R)-PtB | 100 | 86.5 | 100 | 33 | p-TSA | 3.1 | 29 |

*styrenic bead, functionalized with sulfonic acid groups (acid concentration > 2M) sold by The Dow Chemical Company under the trademark DOWEX DR-2030 ion exchange resin.
**No water used in the reaction.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in material science, chemistry, and molecular biology or related fields are intended to be within the scope of the following claims.

What is claimed is:

1. A process comprising contacting in a reaction mixture a propylene glycol ether racemate of formula II

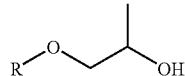

(II)

where R is selected from an alkyl selected from $CH_3$, $CH_3CH_2$, $CH_3(CH_2)_2$, $CH_3(CH_2)_3$ and $C(CH_3)_3$, or aryl group; where the racemate is at a concentration of at least 5% v/v; and where the reaction mixture further comprises an acyl donor which is an activated acyl donor selected from the group consisting of an enol ester; with an effective amount of an enzyme catalyst hydrolase whereby an enantiomer of the racemate is enantioselectively transesterified to a corresponding enantiomer of acylated propylene glycol ether
where the racemate, the acyl donor, and the enzyme catalyst hydrolase comprise 100% v/v of the reaction mixture.

2. The process of claim 1, where the acyl donor is selected from vinyl acetate, vinyl propionate, isopropenyl acetate and 1-ethoxyvinyl acetate.

3. The process of claim 2, where the acyl donor is selected from vinyl acetate and isopropenyl acetate.

4. The process of claim 1, where the hydrolase is a lipase.

5. The process of claim 4, where the lipase is a *Candida antarctica* lipase fraction B.

6. The process of claim 1, where the racemate and the acyl donor are present in a ratio which results in about 50% conversion of the racemate to an acylated propylene glycol ether.

7. The process of claim 1, where about 30% to about 50% of the racemate is transesterified.

8. The process of claim 1, where enantiomer purity of the acylated propylene glycol ether is at least about 70% ee.

9. The process of claim 1, further comprising:
   a) recovering the desired enantiomer of acylated propylene glycol alkyl ether from the reaction mixture; and
   b) converting the recovered acylated propylene glycol alkyl ether enantiomer to obtain a corresponding enantiomer of-propylene glycol alkyl ether.

10. The process of claim 1, further comprising recovering unreacted enantiomeric substrate from the reaction mixture.

11. The process of claim 1, further comprising recycling the enzyme catalyst.

12. The process of claim 1 wherein the racemate comprises at least 10% v/v of the reaction mixture.

13. The process of claim 1 where the racemate comprises at least 20% v/v of the reaction mixture.

14. A process for the preparation of the chiral compound of formula III

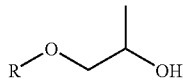
(II)

said process comprising the steps of:
(a) contacting in a reaction mixture a propylene glycol ether racemate of formula II

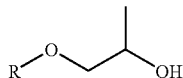
(II)

where R is an alkyl, aryl-substituted alkyl, allylic or acetal group, and where the reaction mixture further comprises an acyl donor selected from the group consisting of an activated ester, an enol ester, and an anhydride, with an effective amount of an enzyme catalyst hydrolase selected from the group consisting of a lipase, an esterase, an acylase and a protease whereby (S)-1-alkoxy-2-propanol and (R)-1-alkoxy-2-propanol acylate are obtained;
(b) separating (S)-1-alkoxy-2-propanol from (R)-1-alkoxy-2-propanol acylate formed in step (a);
(c) dealkoxylating (S)-1-alkoxy-2-propanol separated in step (b) under mild reaction conditions in the presence of an acid catalyst to obtain (S)-1,2-propanediol; and
(d) isolating (S)-1,2-propanediol obtained in step (c).

15. The process of claim 14, further comprising the steps of
(e) dealkoxylating (R)-1-alkoxy-2-propanol acylate, separated in step (b), under mild reaction conditions in the presence of an acid catalyst to obtain (R)-1,2-propanediol; and
(f) isolating (R)-1,2-propanediol obtained in step (e).

16. The process of claim 14 or claim 15, where R is selected from $C(CH_3)_3$, $C(CH_3)_2C_6H_5$, $C(CH_3)(C_6H_5)_2$, $C(C_6H_5)_3$, $C(CH_3)_2CH_2CH_3$, $CH_2C_6H_5$, $CH_2CH\!=\!CH_2$, $CH_2C\!=\!CH$, $CH_2OCH_2CH_2OCH_3$, and $CH_2OCH_3$.

17. The process of claim 16 where the acid catalyst in step (c) is p-toluene sulfonic acid or an ion exchange resin.

18. The process of claim 16, where the hydrolase is lipase or esterase.

19. The process of claim 18, further comprising the step of
(e) dealkoxylating (R)-1-tert-butoxy acetoxy propane, separated in step (b), under mild reaction conditions in the presence of p-toluene sulfonic an acid catalyst to obtain (R)-1,2-propanediol; and
(f) isolating (R)-1,2-propanediol obtained in step (e).

20. The process of claim 18 where the acid catalyst in step (c) is p-toluene sulfonic acid or an ion exchange resin.

21. The process of claim 18, where the hydrolase is *Candida antarctica* lipase fraction B.

22. The process of claim 21 where the acid catalyst in step (c) is p-toluene sulfonic acid or an ion exchange resin.

23. The process of claim 16, where the R is $C(CH_3)_3$.

24. The process of claim 23, where the hydrolase is lipase or esterase.

25. The process of claim 24, where the hydrolase is *Candida antarctica* lipase fraction B.

26. The process of claim 23 where the acid catalyst in step (c) is p-toluene sulfonic acid or an ion exchange resin.

27. The process of any one of claims 14 or 15, where the acid catalyst in step (c) is p-toluene sulfonic acid or an ion exchange resin.

28. The process of claims 14 or 15 where the hydrolase is lipase or esterase.

29. The process of claim 28 where the hydrolase is *Candida antarctica* lipase fraction B.

30. The process of claim 14, said process comprising the steps of:
(a) contacting in a reaction mixture (R,S)-1-tert-butoxy-2-propanol, where the reaction mixture further comprises an vinyl acetate, with an effective amount of *Candida antarctica* lipase fraction B whereby (S)-1-tert-butoxy-2-propanol and (R)-1-tert-butoxy-acetoxy propane are obtained;
(b) separating (S)-1-tert-butoxy-2-propanol from (R)-1-tert-butoxy-acetoxy propane by distillation;
(c) dealkoxylating (S)-1-tert-butoxy-2-propanol separated in step (b) under mild reaction conditions in the presence of p-toluene sulfonic an acid catalyst to obtain (S)-1,2-propanediol; and
(d) isolating (S)-1,2-propanediol obtained in step (c).

* * * * *